(12) United States Patent
Khalaf et al.

(10) Patent No.: US 7,700,765 B2
(45) Date of Patent: Apr. 20, 2010

(54) DNA MINOR GROOVE BINDING COMPOUNDS

(75) Inventors: Abedawn Khalaf, Glasgow (GB); Roger Waigh, Glasgow (GB); Colin Suckling, Glasgow (GB)

(73) Assignee: University of Strathclyde, Glasgow (GB)

( * ) Notice: Subject to any disclaimer, the term of this patent is extended or adjusted under 35 U.S.C. 154(b) by 1201 days.

(21) Appl. No.: 10/500,093

(22) PCT Filed: Dec. 24, 2002

(86) PCT No.: PCT/GB02/05916

§ 371 (c)(1), (2), (4) Date: Nov. 17, 2004

(87) PCT Pub. No.: WO03/059881

PCT Pub. Date: Jul. 24, 2003

(65) Prior Publication Data

US 2007/0117760 A1   May 24, 2007

(30) Foreign Application Priority Data

Dec. 24, 2001  (GB)  .................................. 0130868

(51) Int. Cl.
*C07D 403/02* (2006.01)
*C07D 403/10* (2006.01)
*C07D 403/14* (2006.01)

(52) U.S. Cl. ............................. 540/8; 540/9; 548/146; 548/148; 548/302.7; 548/414; 548/419; 548/421; 548/429; 549/289

(58) Field of Classification Search .................. None
See application file for complete search history.

(56) References Cited

U.S. PATENT DOCUMENTS

| | | | |
|---|---|---|---|
| 4,912,199 A | 3/1990 | Lown et al. | |
| 5,273,991 A | 12/1993 | Lee | |
| 5,637,621 A | 6/1997 | Bolonick et al. | |
| 5,698,674 A | 12/1997 | Bruice et al. | |
| 5,753,629 A | 5/1998 | Beria et al. | |
| 6,090,947 A | 7/2000 | Dervan et al. | |

FOREIGN PATENT DOCUMENTS

| | | |
|---|---|---|
| EP | 0 343 893 A1 | 5/1989 |
| EP | 0 343 893 | 11/1989 |
| WO | WO 97/28123 | 8/1997 |
| WO | WO 97/30975 | 8/1997 |
| WO | WO 98/21202 | 5/1998 |
| WO | WO 01/19792 A1 | 3/2001 |
| WO | WO 01/74898 A2 | 10/2001 |
| WO | WO 02/00650 A2 | 1/2002 |
| WO | WO 02/100832 A1 | 12/2002 |
| WO | WO 02/101007 A2 | 12/2002 |

OTHER PUBLICATIONS

Human Immunodeficiency Virus I from Merck manual, pp. 1-16. Accessed Aug. 27, 2009.*
Respiratory Viruses Introduction from Merck manual, pp. 1-2. Accessed Aug. 27, 2009.*
Severe Acute Respiratory Syndrome from Merck manual, pp. 1-2. Accessed Aug. 27, 2009.*
Acute Viral Hepatitis from Merck manual, pp. 1-8. Accessed Aug. 27, 2009.*
Mosch B, Morawski M, Mittag A, Lenz D, Tarnok A, Arendt T, "Aneuploidy and DNA replication in the Normal Human Brain and Alzheimer's Disease," The Journal of Neuroscience, 2007, 27(26): 6859-6867.*
Dementia from Merck manual, pp. 1-17. Accessed Jul. 29, 2009.*
Mattson MP, "Pathways towards and away from Alzheimer's disease," Nature, Aug. 2004, 430: 631-639.*
Introcution to Cancer from Merck manual, p. 1. Accessed Mar. 5, 2008.*
Clinical Aspects of Cancer from Merck manual, pp. 1-4. Accessed Mar. 5, 2008.*
Auerbach R, Akhtar N, Lewis RL, Shinners BL, "Angiogenesis assays: Problems and pitfalls," Cancer and Metastasis Reviews, 2000, 19: 167-172.*
Gura T, "Systems for Identifying New Drugs Are Often Faulty," Science, 1997, 278: 1041-1042.*
Jain RK, "Barriers to Drug Delivery in Solid Tumors," Scientific American, 1994, 58-65.*
Bloomfield et al. "Electronic and Vibrational Spectroscopy" *Nucleic Acids: Structures, Properties and Functions*, pp. 176-180 and 561-564, (2000).
Abedawn I. Khalaf et al, "The Synthesis of Some Head to Head Linked DNA Minor Groove Binders" *Tetrahedron*, vol. 56: pp. 5225-5239 (2000).
B.S. Praveen Reddy et al, "Synthetic DNA minor groove-binding drugs" *Pharmacology & Therapeutics*, vol. 84: pp. 1-111 (1999).
Bernhard H. Geierstanger et al, "Design of A G·C-Specific DNA Minor Groove-Binding Peptide" *Science*, vol. 266: pp. 646-651 (1994).
Bertrand Plouvier et al, "Antitumor Combilexin. A Thiazole-Containing Analogue of Netropsin Linked to an Acridine Chromophore" *Bioconjugate Chem.*, vol. 5: pp. 475-481 (1994).

(Continued)

*Primary Examiner*—Anish Gupta
*Assistant Examiner*—Julie Ha
(74) *Attorney, Agent, or Firm*—Caesar, Rivise, Bernstein, Cohen & Pokotilow, Ltd.

(57) ABSTRACT

There is provided an oligopeptide compound comprising: (a) at least one nitrogen-containing basic group attached to at least one end of the oligopeptide; and (b) two or more heterocyclic monomers, at least one of which is substituted in the heterocyclic part by a branched, cyclic or part cyclic $C_{3-5}$ alkyl group, or a pharmaceutically acceptable salt or solvate thereof; which compound, salt or solvate binds to the minor groove of DNA.

28 Claims, 9 Drawing Sheets

OTHER PUBLICATIONS

Bertrand Plouvier et al, "Influence of the methyl substituents of a thiazole-containing lexitropsin on the mode of binding to DNA" *Anti-Cancer Drug Design*, vol. 10: pp. 155-166 (1995).

Christian Bailly et al, "Binding Properties and DNA Sequence-Specific Recognition of Two Bithiazole-Linked Netropsin Hybrid Molecules" *Biochemistry*, vol. 31: pp. 8349-8362 (1992).

David E. Wemmer, "Ligands Recognizing the Minor Groove of DNA: Development and Applications" *Biopolymers (Nucleic Acid Sciences)*, vol. 52: pp. 197-211, 2001.

Dmitry V. Bugreev et al, "Inhibition of Human DNA Topoisomerase I by New DNA Minor Groove Ligands: Derivatives of Oligo-1,3-Thiazolecarboxamides" *Antisense & Nuclear Acid Drug Development*, vol. 11: 137-147 (2001).

E.L. Vasyutina et al, "Interaction of the Human Topoisomerase I-DNA Complex with Oligo-1,3-Thiazolecarboxamides and Their Oligonucleotide Conjugates" *Molecular Biology*, vol. 34, No. 34: pp. 356-362 (2000).

Guojian Xie et al, "Bisindolylmaleimides Linked to DNA Minor Groove Binding Lexitropsins: Synthesis, Inhibitory Activity against Topoisomerase I, and Biological Evaluation" *Journal of Medicinal Chemistry*, vol. 39: pp. 1049-1055 (1996).

Jakob Bunkenborg et al, "NMR Characterization of the DNA Binding Properties of a Novel Hoechst 33258 Analogue Peptide Building Block" *Bioconjugate Chem.*, vol. 13: pp. 927-936 (2002).

John W. Trauger et al, "Recognition of 16 Base Pairs in the Minor Groove of DNA by a Pyrrole-Imidazole Polyamide Dimer" *Journal of the American Chemical Society*, vol. 120: pp. 3534-3535 (1998).

K. Ekambareswara Rao et al, "Synthesis of Novel Thiazole-Containing DNA Minor Groove Binding Oligopeptides Related to the Antibiotic Distamycin" *J. Org. Chem.*, vol. 55: pp. 728-737 (1990).

K.E. Rao, et al, "Molecular recognition between oligopeptides and nucleic acids: DNA sequence specificity and binding properties of thiazole-lexitropsins incorporating the concepts of base site acceptance and avoidance" Anti-Cancer Drug Design, vol. 5: pp. 3-20 (1990).

K.F. Tuchin et al, "Ligands Possessing Affinity for Definite Pairs of DNA Bases" *Soviet J. Bioorg. Chem.(Eng. Transl.)*, vol. 4: pp. 780-791 (1978).

Leif Grehn et al, "Synthesis and Antiviral Activity of Distamycin A Analogues: Substitutions on the Different Pyrrole Nitrogens and in the Amidine Function" *Journal of Medicinal Chemistry*, vol. 26: pp. 1042-1049 (1983).

Liliane A. Dickinson et al, "Inhinition of RNA polymerase II transcription in human cells by synthetic DNA-binding ligands" *Proc. Natl. Acad. Sci. USA*, vol. 95: pp. 12890-12895 (1998).

Lu Ding et al, "Synthesis and Antiviral Activity of Three Pyrazole Analogues of Distamycin A" *Acta Chemica Scandinavica*, vol. 48: pp. 498-505 (1994).

Milan Mrksich et al "Antiparallel side-by-side dimeric motif for sequence-specific recognition in the minor groove of DNA by the designed peptide 1-methylimidazole-2-carboxamde netropsin" *Proc. Natl. Acad. Sci. USA*, vol. 89: pp. 7586-7590 (1992).

Moses Lee et al, "GC Base Sequence Recognition by Oligo(imidazolecarboxamide) and C-Terminus-Modified Analogues of Distamycin Deduced from Circular Dichroism, Proton Nuclear Magnetic Resonance, and Methidiumpropylethylenediamineteraacetate-Iron(II) Footprinting Studies" *Biochemistry*, vol. 32: pp. 4237-4245 (1993).

Natalia B. Dyatkina et al, "Minor Groove DNA Binders as Antimicrobial Agents. 1. Pyrrole Tetraamides Are Potent Antibacterials against Vancomycin Resistant *Enteroccoci* and Methicillin Resistant *Staphylococcus aureus*" *Journal of Medicinal Chemistry*, vol. 45: pp. 805-817 (2002).

Nicholas R. Wurtz et al, "Inhibition of DNA Binding by NF-kB with Pyrrole-Imidazole Polyamides" *Biochemistry*, vol. 41: pp. 7604-7609 (2002).

Nouri Neamati et al, "Highly Potent Synthetic Polyamides, Bisdistamycins, and Lexitropsins as Inhibitors of Human Immunodeficiency Virus Type 1 Integrase" *Molecular Pharmacology*, vol. 54: 280-290(1998).

Peter B. Dervan, "Molecular Recognition of DNA by Small Molecules" *Bioorganic & Medicinal Chemistry*, vol. 9: pp. 2215-2235 (2001).

Robert V. Fishleigh et al "DNA Binding, Solubility, and Partitioning Characteristics of Extended Lexitropsins" *Journal of Medicinal Chemistry*, vol. 43: pp. 3257-3266 (2000).

Roland W. Burli et al, "DNA Binding Ligands with Excellent Antibiotic Potency Against Drug-Resistant Gram-Positive Bacteria" *Bioorganic & Medicinal Chemistry Letters*, vol. 12: pp. 2591-2594 (2002).

Rulin Zhao et al, "Synthesis and Biological Evaluation of Hybrid Molecules Containing the Pyrroloquinoline Nucleus and DNA Minor Groove Binders" *Bioorganic & Medicinal Chemistry Letters*, vol. 6, No. 18: pp. 2169-2172 (1996).

S.M. Sondhi et al, "Lexitropsin Conjugates: Action on DNA Targets" *Current Medicinal Chemistry*, vol. 4: pp. 313-358 (1997).

Sanjay K. Sharma et al, "Design and synthesis of new thiazolated cross-linked DNA binding polyamides for altered sequence recognition" *Tetrahedron*, vol. 58: pp. 3417-3421 (2002).

Sanjay K. Sharma et al, "Design and Synthesis of Novel Thiazole-Containing Cross-Linked Polyamides Related to the Antiviral Antibiotic Distamycin" *J. Org. Chem.*, vol. 65: pp. 1102-1107 (2000).

Sanjay K. Sharma et al, "Design, Synthesis, and Intracellular Localization of a Fluorescently Labled DNA Binding Polyamide Related to the Antibiotic Distamycin" *Bioorganic & Medicinal Chemistry Letters*, vol. 11: pp. 769-772 (2001).

Sanjay K. Sharma et al, "Inhibition of Feline Immunodeficiency Virus (FIV) Replication DNA Binding Polyamides" *Bioorganic & Medicinal Chemistry Letters*, vol. 12: pp. 2007-2010 (2002).

Silvana Frau et al, "Binding of a Porphyrin Conjugate of Hoechst 33258 to DNA. II. NMR Spectroscopic Studies Detect Multiple Binding Modes to A 12-MER Nonself-Complementary Duplex DNA" *Nucleosides, Nucleotides & Nucleic Acids*, vol. 20(1&2), 145-156 (2001).

Tammy J. Dwyer et al, "Design and Binding of a Distamycin A Analog to d(CGCAAGTTGGC)•d(GCCAACTTGCG): Synthesis, NMR Studies, and Implications for the Design of Sequence-Specific Minor Groove Binding Oligopeptides" *Journal of the American Chemical Society*, vol. 114, No. 15: pp. 5910-5919 (1992).

Vladimir A. Ryabinin et al, "Synthesis and Evaluation of Oligo-1,3-thiazolecarboxamide Derivatives as HIV-1 Reverse Transcriptase Inhibitors" *Bioorganic & Medicinal Chemistry*, vol. 8: pp. 985-993 (2000).

Xiaogang Han et al, "Sequence Specific Recognition of Ligand-DNA Complexes Studied by NMR" *Current Medicinal Chemistry*, vol. 8: pp. 551-581 (2001).

Yanwu Yang et al, "Studies on Cooperative Binding of an Extended Distamycin A Analogue in the Minor Grove of DNA by NMR Spectroscopy" *Biochemical and Biophysical Research Communications*, vol. 222: pp. 764-769 (1996).

Zhou et al., "Double Activation Preparation of an Acridinyl-Isoxazolyl-Lexitropsin", Bioinorganic and Medicinal Chemistry Letters, vol. 7, pp. 2455-2456 (1997).

\* cited by examiner

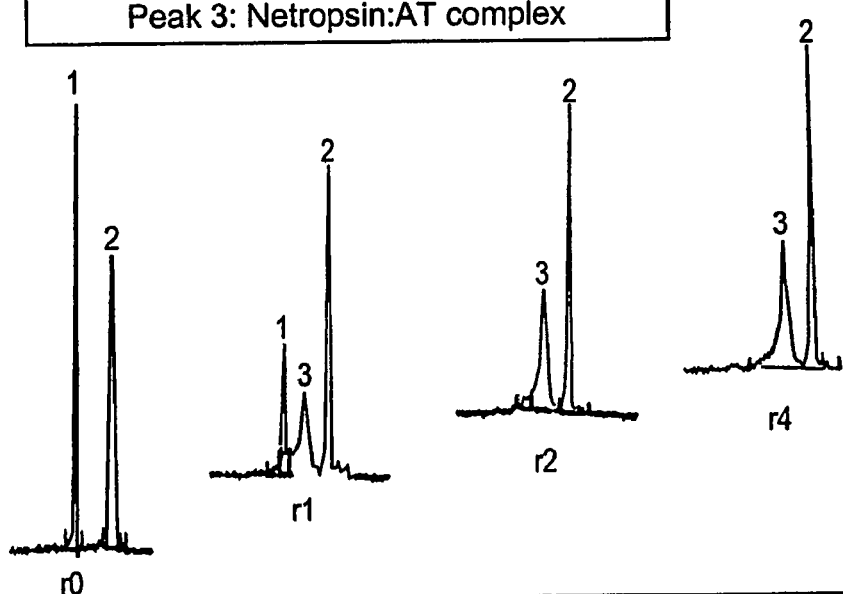
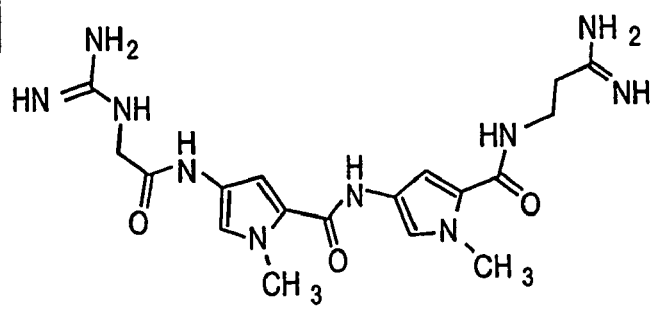
Competitive binding studies with netropsin.
*Fig. 1*

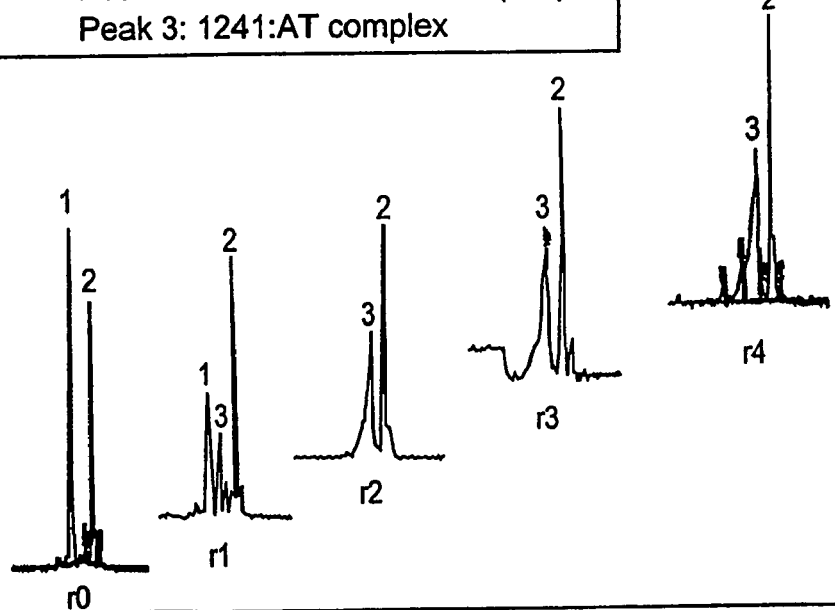
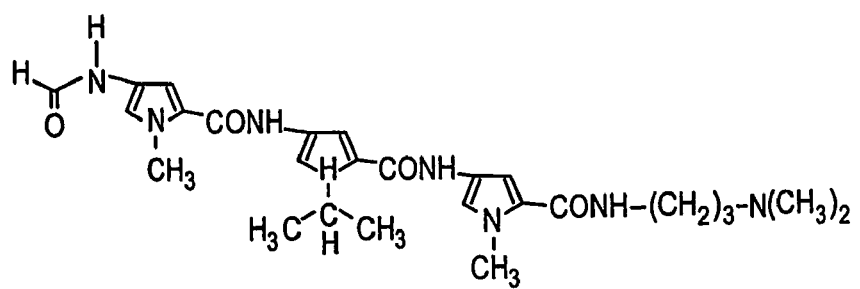
Competitive binding studies with compound 12/41
*Fig.2*

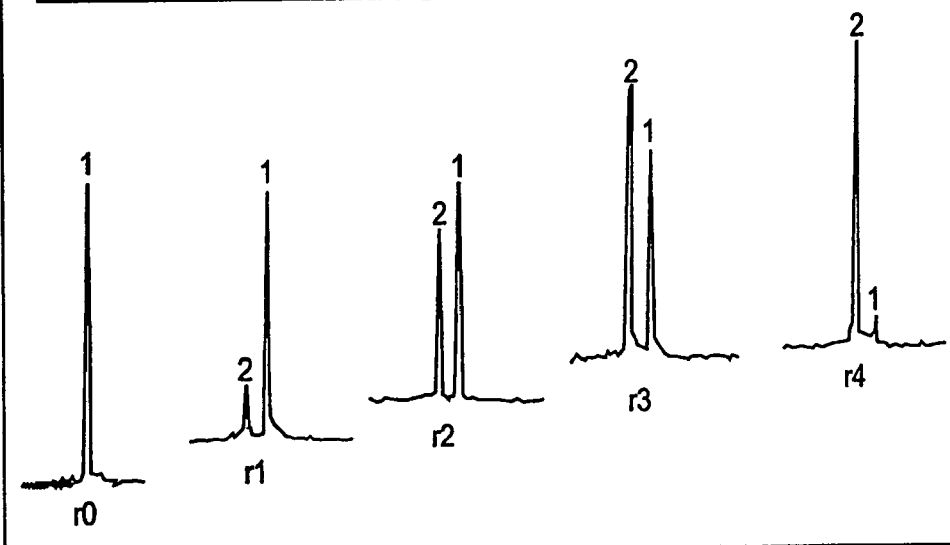
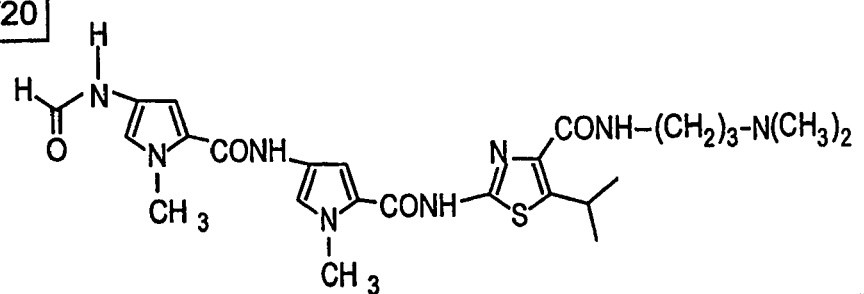
Capillary electrophoresis studies of the interaction between compound 13/20 and DNA decamer CGACTAGTCG.
*Fig.3*

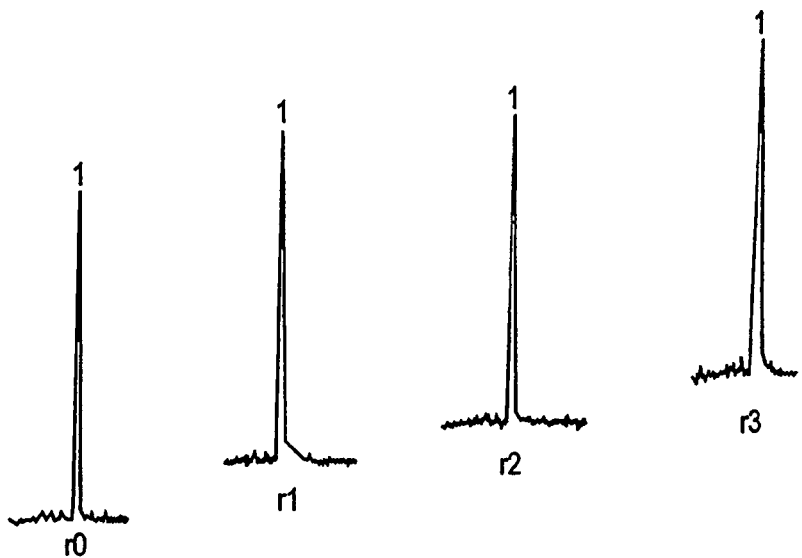
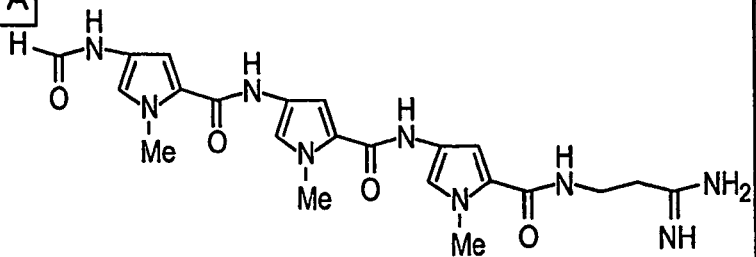
Capillary electrophoresis studies of the interaction between distamycin and DNA decamer CGACTAGTCG.
*Fig. 4*

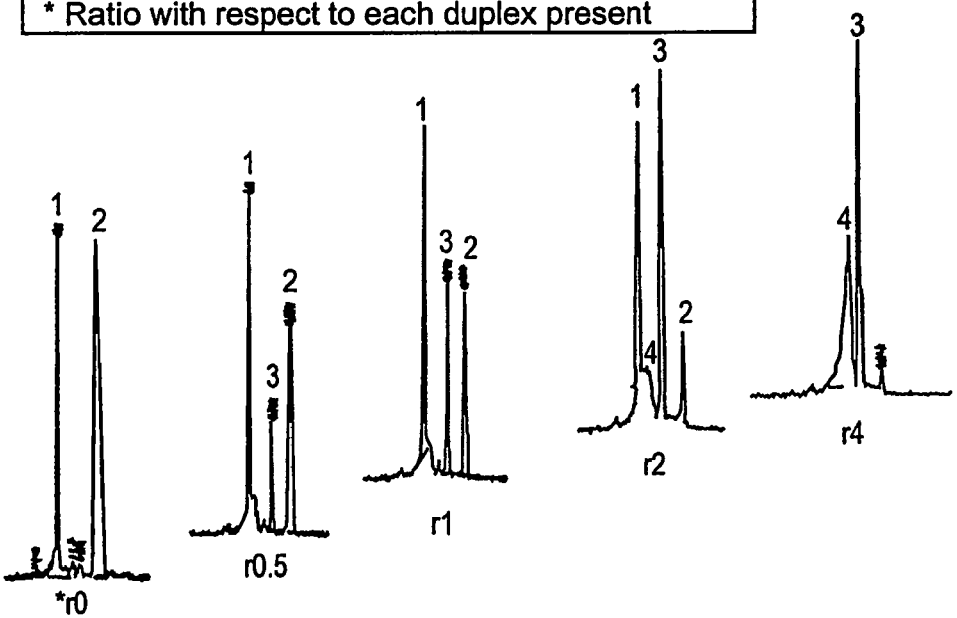
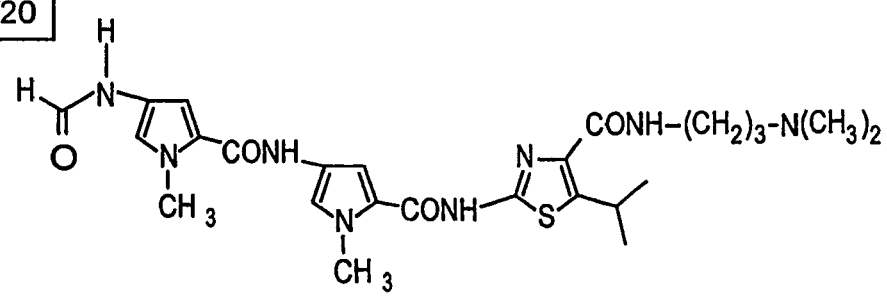
Competitive binding studies with compound 13/20
*Fig 5*

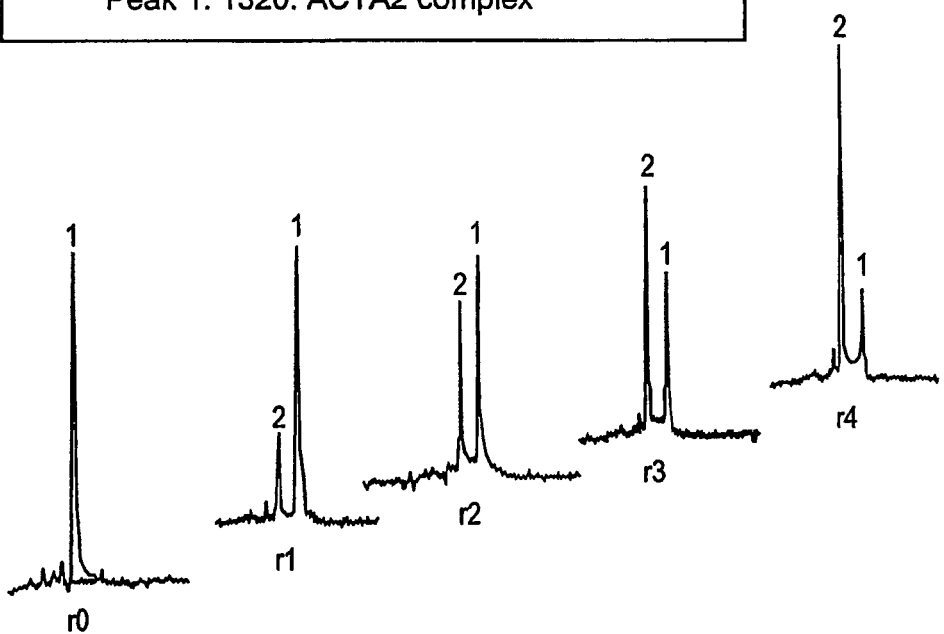
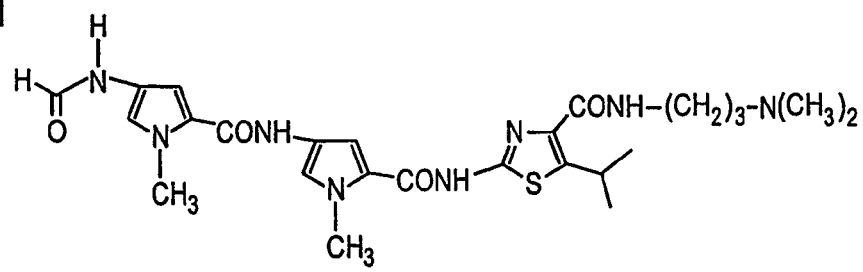
Capillary electrophoresis studies of the interaction between compound 13/20 and DNA decamer CCACTAGTGG
*Fig 6*

Footprinting studies with compound 13/20

13/20

5'-GGATCCATATGCGGCAATACACATGGCCGATTTCCAACTGCACTAGTCGTAGCGCGATCAAGGTTAAGCTCCCGTTCTATCC
           x xxxxxxxxxx
TGGTATAGCAATTAGGGCGTGAAGAGTTATGTAAAGTACGTCCGGTGGGTCGTGTTTGTCATCTCAGCCTCGAATGCGGATC( (Experiment carried out at 0.03 μM of compound 13/20)

Footprinting studies with compound 13/51

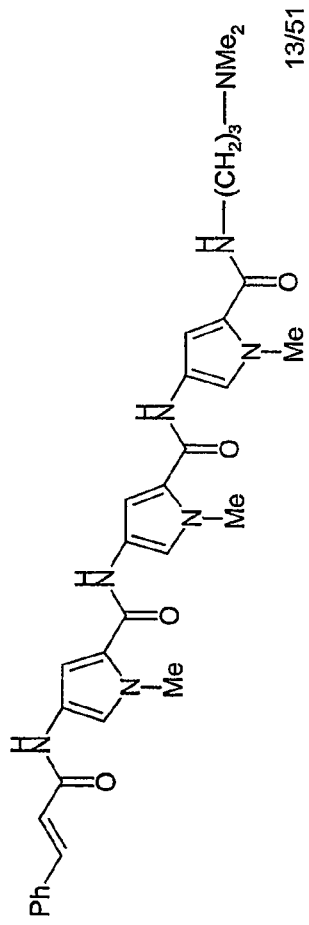

5'-GGATCCATATGGGCAATACACATGCCGATTTCCAACTGCACTAGTCGTAGCGCGATCAAGGTTAAGCTCCCGTTCTATCC
xxxxx(0.1)

TGGTATAGCAATTAGGGCGTGAAGAGTTATGTAAAGTACGTCCGGTGGGTCTGTTTGTCATCTCAGCCTGAATGCGGATC
xxxx(3) xxxxxx(0.1) xxxxx(1)xxxxx(0.01) xxxxx(0.1)

The numbers in brackets refer to the concentration of compound 13/51 (in μM) at which the relevant footprint was observed.

Fig. 8

DNA MINOR GROOVE BINDING COMPOUNDS

FIELD OF THE INVENTION

This invention relates to synthetic compounds that have affinity for nucleic acids, and in particular to compounds that bind to the minor groove of DNA.

BACKGROUND AND PRIOR ART

Because of its fundamental role in molecular biological processes, DNA represents an important target for drug action. Compounds that can recognize defined sequences of DNA have a wide variety of potential uses, such as the modulation of gene expression.

The outer surface of double-helical DNA has two channels, namely the major and minor grooves. Both of these grooves contain chemical information by way of arrangements of hydrogen-bond donors and acceptors, electrostatic charges, dipoles, hydrophobic regions and so on.

The major groove contains approximately twice the information content of the minor groove in terms of the number of potential hydrogen-bonding contacts. In view of this, the major groove is the preferred recognition site for cellular proteins such as control proteins, promoters and repressors.

In contrast, the minor groove is normally (with a few exceptions) relatively unoccupied. The vulnerability of the minor groove makes it a particularly useful target for compounds that bind to DNA. Indeed, perhaps for this very reason, the minor groove is the binding site for certain naturally occurring antibiotics (such as netropsin and distamycin).

Netropsin and distamycin are oligopeptides based on pyrrole amino acid monomers. These compounds both bind to DNA with dissociation constants in the order of $10^{-5}$ M. They also show a preference for AT-rich regions of DNA. Although they have intrinsic biological activity, netropsin and distamycin also have many limitations including toxicity, moderate affinity and limited selectivity. A number of workers have therefore prepared synthetic analogues of netropsin and distamycin, with a view to overcoming these disadvantages. Many of these compounds are reviewed by Sondhi et al. (*Curr. Med. Chem.* 4, 313 (1997)), Reddy et al. (*Pharmacology & Therapeutics* 84, 1 (1999)), Wemmer (*Biopolymers* 52, 197 (2001)) and Dervan (*Bioorg. Med. Chem.* 9, 2215 (2001)).

Compounds designed to bind to DNA regions containing GC base pairs are described in, for example: *Anti-Cancer Drug Design* 5, 3 (1990); *Proc. Natl. Acad. Sci. USA* 89, 7586 (1992); *Biochemistry* 32, 4237 (1993); *Science* 266, 647 (1994); *Anti-Cancer Drug Design* 10, 155 (1995); *Bioorg. Med. Chem.* 8, 985 (2000); and *Mol. Biol.* 34, 357 (2000). Various other netropsin and distamycin analogues are described in: *J. Am. Chem. Soc.* 114(15), 5911 (1992); *Biochemistry* 31, 8349 (1992); *Bioconjugate Chem.* 5, 475 (1994); *Biochem. Biophys. Res. Commun.* 222, 764 (1996); *J. Med. Chem.* 43, 3257 (2000); and *Tetrahedron* 56, 5225 (2000). Further, the use of certain netropsin and distamycin analogues as antimicrobial, antiviral and/or antitumor agents is described in *Molecular Pharmacology* 54, 280 (1998), *Bioorg. Med. Chem. Lett.* 6(18), 2169 (1996), *J. Med. Chem.* 45, 805 (2002), *Bioorg. Med. Chem. Lett.* 12, 2007 (2002), international patent applications WO 97/28123, WO 98/21202, WO 01/74898 and WO 02/00650, as well as in U.S. Pat. Nos. 4,912,199, 5,273,991, 5,637,621, 5,698,674 and 5,753,629. Methods of synthesizing analogues of netropsin and distamycin are described in U.S. Pat. No. 6,090,947.

Cellular uptake of distamycin analogues is described in *Bioorg. Med. Chem. Lett.* 11, 769 (2001).

None of the above-mentioned documents describe oligopeptide analogues of netropsin or distamycin, which analogues comprise at least two heterocyclic monomers, at least one of which is substituted in the heterocyclic part by a branched, cyclic or part cyclic $C_{3-5}$ alkyl group. Surprisingly, we have found that compounds of this type bind with a high affinity and specificity to the minor groove of DNA.

DESCRIPTION OF THE INVENTION

According to the invention there is provided oligopeptide compounds comprising:

(a) at least one nitrogen-containing basic group attached to at least one end of the oligopeptide; and (b) two or more heterocyclic monomers, at least one of which is substituted in the heterocyclic part by a branched, cyclic or part cyclic $C_{3-5}$ alkyl group, or a pharmaceutically acceptable salt or solvate thereof;

which compounds, salts or solvates bind to the minor groove of DNA, and which compounds are referred to hereinafter as "the compounds of the invention".

When used herein, the term "oligopeptide" includes organometallic and, particularly, organic compounds that contain at least one amide (e.g. —C(O)NH—) group that links different parts of the molecule. Preferred oligopeptide compounds are those of low molecular weight (e.g. below 2000, such as below 1500 and, particularly, below 1000 g mol$^{-1}$). Preferred oligopeptide compounds also include those that comprise heterocyclic amino acids (i.e. heterocyclic groups that possess both carboxylic acid and amine functionalities) that are coupled to each other via linkages that include at least one amide bond (e.g. a direct amide bond or a linkage formed by reaction of two heterocyclic amino acids with a compound that possesses two carboxylic acid groups, two amine groups or one acid and one amine group). Suitable compounds possessing two carboxylic acid groups, two amine groups or one acid and one amine group are known to those skilled in the art, for example the "linkers" disclosed in *Curr. Med. Chem.* 4, 313-358 (1997), *Pharmacology & Therapeutics* 84, 1-111 (1999), *J. Med. Chem.* 43, 3257-3266 (2000), *Tetrahedron* 56, 5225-5239 (2000), the disclosures of which documents are hereby incorporated by reference.

When used herein, the term "nitrogen-containing basic group" includes nitrogen-containing compounds that form salts with organic or inorganic acids. As such, the term includes nitrogen-containing groups that, in their neutral state, have a $pK_a$ in water of at least 4 (preferably at least 5, 6 or 7, and particularly in the range of 8 to 12). The term therefore specifically includes amidino, guanidino and, particularly, amino groups, any of which may be cyclic or acyclic. Preferred nitrogen-containing basic groups include —N(H)C(=NH)NH$_2$, —C(=NH)NH$_2$ and, particularly, amino groups such as —NH$_2$, alkylamino (e.g. —N(H)CH$_3$) and dialkylamino (e.g. —N(CH$_3$)$_2$) groups and saturated aza-heterocyclic groups such as pyrrolidinyl and piperazinyl. Particularly preferred nitrogen-containing basic groups include —N(CH$_3$)$_2$. For the avoidance of doubt, the nitrogen-containing basic group is a separate moiety from the two or more heterocyclic groups mentioned at point (b) above.

When used herein, the term "heterocyclic group" includes 4- to 12-membered (e.g. 5- to 10-membered) heterocyclic groups containing one or more heteroatoms selected from N, O and S. The term therefore includes such groups that are mono- or bicyclic, and which may be saturated, part-unsaturated, aromatic or, where appropriate, part-aromatic. Preferred heterocyclic groups include aromatic or part-aromatic groups such as pyrrolyl, imidazolyl, thiazolyl, oxazolyl, benzoxazolyl, furanyl, thienyl, pyridyl and coumarinyl. Particularly preferred heterocyclic groups include pyrrolyl, imidazolyl, thiazolyl and oxazolyl.

By "substituted in the heterocyclic part", we mean that each of the essential branched, cyclic or part cyclic $C_{3-5}$ alkyl groups is a direct substituent on the heterocyclic ring (whether attached to the ring via a heteroatom or otherwise) of each heterocyclic monomer bearing such a group.

In one embodiment of the invention, at least one heterocyclic group that is present (e.g. an imidazolyl, a thienyl or, particularly, a thiazolyl group) is substituted at a ring C-atom by the branched, cyclic or part cyclic $C_{3-5}$ alkyl group.

In another embodiment of the invention, at least one heterocyclic group that is present is a thiazolyl group (e.g. a 1,3-thiazolyl group that is substituted in the 5-position by the branched, cyclic or part cyclic $C_{3-5}$ allyl group).

The compounds of the invention may be provided in a form rendering them bioavailable. When used herein, the term "bioavailable" includes compounds that, following administration, are in a form in which they can interact with a biological system, thereby providing a measurable therapeutic response. The term may thus be understood to include compounds that are provided to DNA in a form and/or level that is sufficient to provide a measurable desired or required therapeutic response.

Bioavailability of a compound may be predicted by a number of means known to those skilled in the art including a measurement of a partition coefficient of the compound between water (for example at a pH of between 5 and 9) and an organic, water-immiscible solvent (e.g. octanol), which measurement can be used to predict the behavior in body tissues of the compound in question (for a discussion of which see *J. Med. Chem.* 43, 3257-3266 (2000)).

Bioavailability may be achieved by providing compounds of the invention in a form (e.g. a pharmaceutical formulation) in which they are presented to DNA at an appropriate concentration to provide a measurable therapeutic response. Bioavailability may alternatively be achieved by changing the physicochemical properties of the active species, for example by improving water solubility by using techniques known to those skilled in the art (e.g. by the introduction of additional basic groups, such as described in *J. Med. Chem.* 43, 3257-3266 (2000)).

The compounds of the invention may have a high affinity for at least one DNA sequence. When used herein, the term "high affinity for at least one DNA sequence" includes compounds that, when bound to a minor groove of at least one DNA oligomer or polymer, have a dissociation constant of less than $10^{-5}$ M, preferably less than $10^{-6}$ M (such as $10^{-7}$ M) and particularly less than $10^{-8}$ M. In this respect, dissociation constants may be measured under conditions know to those skilled in the art, for example in water at room temperature (e.g. at or around 20° C.) in the presence of a buffer (e.g. a buffer that stabilizes the pH at 7.5, such as a borate (e.g. at 0.02M) or Tris/HCl (e.g. at 0.01 M) buffer) and at a DNA concentration of between 10 and 30 μM (e.g. 20 μM). Alternatively, dissociation constants may be estimated by a comparison of the binding affinity of a compound to a set DNA sequence with the binding affinity of a well-known compound (e.g. distamycin) to that same sequence.

Unless otherwise specified, the term "DNA" refers to double-stranded DNA. Further, when used herein, the term "DNA sequence" includes any part of (or the whole of) a DNA oligomer or polymer spanning three or more base pairs.

Preferred compounds of the invention also include those in which each essential branched, cyclic or part cyclic $C_{3-5}$ alkyl substituent on a heterocyclic monomer is:
other than cyclopropyl;
a branched $C_{3-5}$ alkyl group such as cyclopropylmethyl, cyclopentyl, isopentyl or isopropyl (e.g. isopentyl and, particularly, isopropyl).

According to a further aspect of the invention, there is provided compounds of formula I,

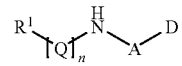

I wherein
$R^1$ represents Het$^1$, $R^{1a}C(O)$— or D-A-N(H)-[Q]$_n$-C(O)-E-C(O)—;
$R^{1a}$ represents
H,
aryl (which latter group is optionally substituted by one or more substituents selected from OH, halo, cyano, nitro, $N(R^{3a})R^{3b}$, $C_{1-4}$ alkyl and $C_{1-4}$ alkoxy),
aromatic or part-aromatic $C_{13-14}$ tricyclic carbocyclyl (which latter group is optionally substituted by one or more substituents selected from OH, halo, cyano, nitro, $N(R^{3a})R^{3b}$, $C_{1-4}$ alkyl and $C_{1-4}$ alkoxy, and which latter group, if part-aromatic, is optionally substituted in the non-aromatic part by one or two oxo groups) or
$C_{1-12}$ alkyl (which latter group is optionally substituted and/or terminated by one or more substituents selected from halo and aryl (which latter group is optionally substituted by one or more substituents selected from OH, halo, cyano, nitro, $N(R^{3a})R^{3b}$, $C_{1-4}$ alkyl and $C_{1-4}$ alkoxy));
A represents, at each occurrence when used herein, $C_{2-6}$ alkylene or $A^1$-C(O)N(H)-$A^2$, wherein $A^2$ is attached to the group D;
$A^1$ represents $C_{1-4}$ alkylene;
$A^2$ represents $C_{2-5}$ alkylene;
D represents, at each occurrence when used herein, —N($R^{2a}$)$R^{2b}$, —C(=N$R^{2c}$)N($R^{2d}$)$R^{2e}$ or —N($R^{2f}$)C(=N$R^{2g}$)N(H)$R^{2h}$;
$R^{2a}$ and $R^{2b}$ independently represent H, $C_{1-16}$ alkyl, Het$^2$ or $R^{2a}$ and $R^{2b}$ together represent (CH$_2$)$_{3-6}$, which alkylene group is optionally interrupted by NR$^4$ and/or is optionally substituted by one or more $C_{1-4}$ alkyl groups;
$R^4$ represents H, $C_{1-6}$ alkyl or Het$^3$;
$R^{2c}$ to $R^{2h}$ independently represent H or $C_{1-6}$ alkyl;
E represents -E$^1$-Het$^4$-, E$^{2a}$, —(CH$_2$)$_{0-3}$N(H)C(O)-E$^{2b}$-C(O)N(H)(CH$_2$)$_{0-3}$— or a structural fragment of the formula wherein E$^3$ represents (CH$_2$)$_{1-2}$, CH=CH, CH=N, CH$_2$—N(R$^a$), (CH$_2$)$_{0-1}$C(O), (CH$_2$)$_{0-1}$O or (CH$_2$)$_{0-1}$S;
$R^a$ represents H or $C_{1-6}$ alkyl;
E$^1$ represents (CH$_2$)$_{0-2}$ or CH=CH;
E$^{2a}$ and E$^{2b}$ independently represent $C_{2-4}$ alkenylene, $C_{3-6}$ cycloalkylene, phenylene or naphthylene;

Het¹ to Het⁴ independently represent four- to twelve-membered heterocyclic groups containing one or more heteroatoms selected from N, O and S, which heterocyclic groups are optionally substituted by one or more substituents selected from =O, OH, halo, cyano, nitro, $N(R^{3a})R^{3b}$, $C_{1-4}$ alkyl and $C_{1-4}$ alkoxy;

$R^{3a}$ and $R^{3b}$ independently represent, at each occurrence when used herein, H or $C_{1-4}$ alkyl, or $R^{3a}$ represents —C(O)R⁵;

$R^5$ represents H or $C_{1-4}$ alkyl;

n represents, at each occurrence when used herein, 2, 3, 4 or 5;

each individual Q independently represents a structural fragment of formula Ia, Ib, Ic, Id, Ie or If

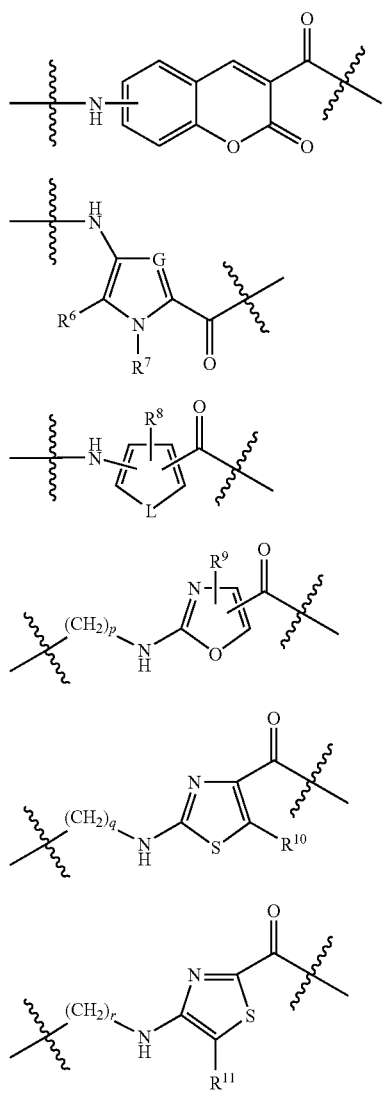

wherein
$R^6$ represents H or $C_{1-6}$ alkyl;
$R^7$ represents $C_{1-12}$ alkyl;
$R^8, R^9, R^{10}$ and $R^{11}$ independently represent H or $C_{1-12}$ alkyl;
G represents CH or N;
L represents O or S;
p, q and r independently represent 0, 1, 2 or 3; and provided that the compound comprises at least one structural fragment of formula Ib, Ic, Id, Ie or If in which $R^6$ or $R^7$, $R^8$, $R^9$, $R^{10}$ or $R^{11}$, respectively, represents branched, cyclic or part cyclic $C_{3-5}$ alkyl;

or a pharmaceutically acceptable derivative thereof, which compounds are also referred to hereinafter as "the compounds of the invention".

Unless otherwise specified, alkyl groups and alkoxy groups as defined herein may be straight-chain or, when there is a sufficient number (i.e. a minimum of three) of carbon atoms, be branched-chain and/or cyclic. Further, when there is a sufficient number (i.e. a minimum of four) of carbon atoms, such alkyl and alkoxy groups may also be part cyclic/acyclic. Such alkyl and alkoxy groups may also be saturated or, when there is a sufficient number (i.e. a minimum of two) of carbon atoms, be unsaturated and/or interrupted by one or more oxygen and/or sulfur atoms. Unless otherwise specified, alkyl and alkoxy groups may also be substituted by one or more halo, and especially fluoro, atoms.

Unless otherwise specified, alkylene groups as defined herein may be straight-chain or, when there is a sufficient number (i.e. a minimum of two) of carbon atoms, be branched-chain. Such alkylene chains may also be saturated or, when there is a sufficient number (i.e. a minimum of two) of carbon atoms, be unsaturated and/or interrupted by one or more oxygen and/or sulfur atoms. Unless otherwise specified, alkylene groups may also be substituted by one or more halo atoms.

The term "aryl", when used herein, includes $C_{6-10}$ aryl groups such as phenyl, naphthyl and the like. When substituted, aryl groups are preferably substituted by between one and three substituents.

The term "aromatic or part-aromatic $C_{13-14}$ tricyclic carbocyclyl", when used herein includes fluorenyl, anthracenyl, 9,10-dihydroanthracenyl, phenanthrenyl, 9,10-dihydrophenanthrenyl and the like.

The term "halo", when used herein, includes fluoro, chloro, bromo and iodo.

Het (Het¹ to Het⁴) groups that may be mentioned include those containing 1 to 4 heteroatoms (selected from the group oxygen, nitrogen and/or sulfur) and in which the total number of atoms in the ring system are between five and twelve. Het (Het¹ to Het⁴) groups may be fully saturated, partly unsaturated, wholly aromatic, partly aromatic and/or bicyclic in character. Heterocyclic groups that may be mentioned include benzodioxanyl, benzodioxepanyl, benzodioxolyl, benzofuranyl, benzofurazanyl, benzimidazolyl, benzomorpholinyl, benzothiazolyl, benzothiophenyl, benzoxazolyl, chromanyl, cinnolinyl, coumarinyl, dioxanyl, furanyl, hydantoinyl, imidazolyl, imidazo[1,2-α]pyridinyl, indolyl, isoquinolinyl, isoxazolyl, maleimido, morpholinyl, oxazolyl, phthalazinyl, piperazinyl, piperidinyl, purinyl, pyranyl, pyrazinyl, pyrazolyl, pyridinyl, pyrimindinyl, pyrrolidinonyl, pyrrolidinyl, pyrrolinyl, pyrrolyl, quinazolinyl, quinolinyl, 3-sulfolenyl, tetrahydropyranyl, tetrahydrofuranyl, thiazolyl, thienyl, thiochromanyl, triazolyl and the like. Values of Het¹, Het² and Het³ that may be mentioned include benzoxazolyl. Values of Het⁴ that may be mentioned include indolyl.

Pharmaceutically acceptable derivatives include salts and solvates. Salts which may be mentioned include acid addition salts.

Compounds of formula I may exhibit tautomerism. All tautomeric forms and mixtures thereof are included within the scope of the invention.

Compounds of formula I may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemization or epimerization, or by derivatization, for example with a homochiral acid followed by separation of the diastereomeric esters by conventional means (e.g. HPLC, chromatography over silica). All stereoisomers are included within the scope of the invention.

Compounds of formula I that may be mentioned include those in which:

$R^{1a}$ represents H or $C_{1-12}$ alkyl, which latter group is optionally substituted and/or terminated by one or more substituents selected from halo and aryl, which latter group is optionally substituted by one or more substituents selected from OH, halo, cyano, nitro, $N(R^{3a})R^{3b}$, $C_{1-4}$ alkyl and $C_{1-4}$ alkoxy;

the compound comprises at least one structural fragment of formula Ib, Ic, Id, Ie or If in which $R^7$, $R^8$, $R^9$, $R^{10}$ or $R^{11}$, respectively, represents branched, cyclic or part cyclic $C_{3-5}$ alkyl.

Branched, cyclic or part cyclic $C_{3-5}$ alkyl groups that may be mentioned include isopropyl, cyclopropylmethyl, isopentyl and cyclopentyl.

Preferred compounds of formula I include those in which:
$R^{1a}$ represents
H,
phenyl, anthracenyl (which latter two groups are optionally substituted by one to three substituents selected from OH, halo, $C_{1-4}$ alkyl and $C_{1-4}$ alkoxy),
9,10-dihydroanthracenyl (which latter group is optionally substituted by one or two oxo groups and/or one to three substituents selected from OH, halo, $C_{1-4}$ alkyl and $C_{1-4}$ alkoxy) or
optionally unsaturated $C_{1-8}$ alkyl, which latter group is substituted by one or more halo groups and/or terminated by phenyl, which latter group is optionally substituted by one or more substituents selected from OH, halo, cyano, nitro, $N(R^{3a})R^{3b}$, $C_{1-2}$ alkyl and $C_{1-2}$ alkoxy;

A represents optionally unsaturated $C_{2-5}$ alkylene or $A^1$-C(O)N(H)-$A^2$;
$A^1$ represents saturated $C_{1-3}$ alkylene;
$A^2$ represents saturated $C_{2-4}$ alkylene;
$R^{2a}$ and $R^{2b}$ independently represent H, $C_{1-4}$ alkyl, Het$^2$ or $R^{2a}$ and $R^{2b}$ together represent $(CH_2)_{3-6}$, which alkylene group is optionally interrupted by NR$^4$ and/or is optionally substituted by a $C_{1-2}$ alkyl group;
$R^4$ represents $C_{1-4}$ alkyl or Het$^3$;
$R^{2c}$ to $R^{2h}$ independently represent H;
E represents -$E^1$-Het$^4$-, cis- or trans-ethenylene, cyclopropylene, 1,3- or 1-4-phenylene, —(CH$_2$)$_{1-2}$N(H)C(O)-phenylene-C(O)N(H)(CH$_2$)$_{1-2}$— or a structural fragment of the formula

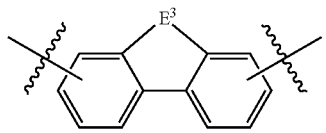

wherein $E^3$ represents $(CH_2)_2$, CH=CH, C(O) or S;

Het$^1$ to Het$^3$ independently represent six- to ten-membered heterocyclic groups containing one or more heteroatoms selected from N, O and S, which heterocyclic groups are optionally substituted by one or more substituents selected from =O, OH, halo, cyano, nitro, $N(R^{3a})R^{3b}$, $C_{1-2}$ alkyl and $C_{1-2}$ alkoxy;

Het$^4$ represents an unsubstituted nine- or ten-membered aromatic heterocyclic group containing one or two N-atoms (e.g. indolyl, such as 2,5- or 2,6-indolyl);

$R^{3a}$ and $R^{3b}$ independently represent, at each occurrence when used herein, H or $C_{1-2}$ alkyl, or $R^{3a}$ represents —C(O)R$^5$;

$R^5$ represents H or $C_{1-2}$ alkyl;
$R^6$ represents H or $C_{1-2}$ alkyl or, when G represents N, $R^6$ may also represent branched, cyclic or part cyclic $C_{3-5}$ alkyl;
$R^7$ represents $C_{1-8}$ alkyl;
$R^8$, $R^9$, $R^{10}$ and $R^{11}$ independently represent H or $C_{1-8}$ alkyl;
p, q and r independently represent 0, 1 or 2;
n represents 3, 4 or 5 or, when $R^1$ represents methyl, Het$^1$ or D-A-N(H)-[Q]$_n$—C(O)-E-C(O)—, then n may also represent 2;
the compound comprises at least one structural fragment of formula Ib, Ic, Id, Ie or If in which $R^7$, $R^8$, $R^9$, $R^{10}$ or $R^{11}$, respectively, represents branched $C_{3-5}$ alkyl.

More preferred compounds of formula I include those in which:
$R^{1a}$ represents
H
phenyl (which latter group is optionally substituted by $C_{1-2}$ alkoxy), 9,10-dioxo-9,10-dihydroanthracenyl (which latter group is optionally substituted by $C_{1-2}$ alkoxy),
saturated, optionally branched $C_{1-6}$ alkyl or
saturated $C_{1-3}$ n-alkyl, which latter group is terminated by phenyl (which latter group is optionally substituted by $C_{1-2}$ alkoxy);

A represents saturated $C_{2-4}$ alkylene or $A^1$-C(O)N(H)-$A^2$;
$A^1$ represents $(CH_2)_{1-3}$;
$A^2$ represents $(CH_2)_{2-4}$;
D represents —N(R$^{2a}$)R$^{2b}$;
$R^{2a}$ and $R^{2b}$ independently represent $C_{1-3}$ alkyl or Het$^2$, or $R^{2a}$ and $R^{2b}$ together represent $(CH_2)_{3-5}$, which alkylene group is optionally interrupted by NR$^4$;
$R^4$ represents $C_{1-3}$ alkyl or Het$^3$;
E represents -(2,5-indolyl)-, —(CH$_2$)$_{0-2}$-(2,6-indolyl)-, —CH=CH-(2,6-indolyl)-, trans-ethenylene, trans-cyclopropylene, 1,3- or 1-4-phenylene, —CH$_2$N(H)C(O)-(1,3- or 1,4-phenylene)-C(O)N(H)CH$_2$— or one of the following structural fragments

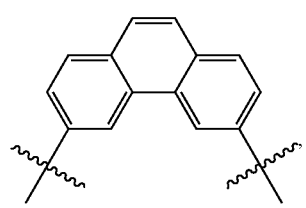

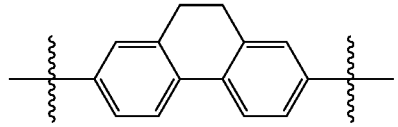

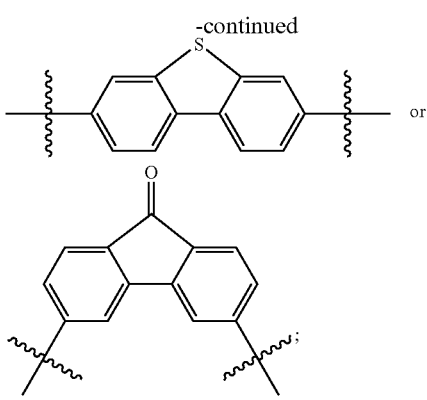

Het¹, Het² and/or Het³ independently represent nine- or ten-membered aromatic heterocycles containing one to three heteroatoms selected from N, O and S;

R⁶ represents H or, when G represents N, R⁶ may also represent branched, cyclic or part cyclic $C_{3-5}$ alkyl;

R⁷, R⁸, R⁹, R¹⁰ and R¹¹ independently represent saturated, optionally branched $C_{1-6}$ alkyl or R⁸ represents H;

p, q and r independently represent 0 or 1;

n represents 3 or 4, or, when R¹ represents methyl or D-A-N(H)-[Q], —C(O)-E-C(O)—, then n may also represent 2;

the compound comprises at least one structural fragment of formula Ib, Ic, Id, Ie or If in which R⁷, R⁸, R⁹, R¹⁰ or R¹¹, respectively, represents iso- or sec-butyl, isopentyl or, particularly, isopropyl;

the compound comprises at least one structural fragment of formula Ib, Ic, Id, Ie or If in which R⁷, R⁸, R⁹, R¹⁰ or R¹¹, respectively, represents ethyl or, particularly, methyl.

Compounds of formula I that are more preferred still include those in which:

R¹ᵃ represents
  H
  methoxyphenyl (e.g. p- or, particularly, m-methoxyphenyl), 9,10-dioxo-9,10-dihydroanthracenyl,
  saturated $C_{1-3}$ alkyl (e.g. methyl) or
  methoxyphenylacetyl (e.g. m- or, particularly, p-methoxyphenyl);

Het¹ represents a nine-membered aromatic heterocycle containing two heteroatoms selected from N, O and S (e.g. 1,3-benzoxazol-2-yl);

A represents saturated $C_{2-4}$ n-alkylene (e.g. n-propylene) or A¹-C(O)N(H)-A²;

A¹ represents $(CH_2)_2$;

A² represents $(CH_2)_3$;

R²ᵃ and R²ᵇ both represent methyl;

E represents —$CH_2$N(H)C(O)-(1,3-phenylene)-C(O)N(H)$CH_2$—;

the —NH— group in the structural fragment of formula Ia is attached in the 6-position of the coumarin ring system;

R⁷ represent saturated, optionally branched $C_{1-3}$ alkyl (e.g. methyl, ethyl or isopropyl);

R⁸ represents isopropyl or, particularly, H;

R⁸ represents methyl;

the —NH— and —C(O)— groups in the structural fragment of formula Ic are attached in the 2- and 5-positions, respectively, of the furan or thiophene ring;

R⁹, R¹⁰ and R¹¹ independently represent saturated, optionally branched $C_{1-3}$ alkyl (e.g. isopropyl);

p represents 1;

q and r represent 0;

the —C(O)— group in the structural fragment of formula Id is attached in the 4-position of the oxazole ring;

n represents 3 or, when R¹ represents methyl, n represents 2 or 3, or, when

R¹ represents D-A-N(H)-[Q]ₙ—C(O)-E-C(O)—, then n represents 2;

the compound comprises at least one structural fragment of formula Ib, Ic, Id, Ie or If in which R⁷, R⁸, R⁹, R¹⁰ or R¹¹, respectively, represents isopropyl.

Particularly preferred compounds of formula I include those in which:

each Q independently represents a structural fragment of formula Ib, Id, Ie or If (such as a structural fragment of formula Ib or Ie);

G represents CH;

R⁷ represents methyl or isopropyl.

Compounds of formula I that may be mentioned include those in which each Q does not represent a structural fragment of formula Id.

According to a further aspect of the invention, there is provided compounds of formula I which are compounds of formula II, $$R^1—Q^1—Q^2—Q^3—N(H)—A—N(R^{2a})(R^{2b})$$

II wherein

R¹ represents Het¹, R¹ᵃC(O)— or D-A-N(H)-Q³-Q²-Q¹-C(O)-E-C(O)—;

Q¹ is absent or represents a structural fragment of formula Ia, Ib, Ic, Id, Ie or If;

Q² represents a structural fragment of formula Ib, Ie or If;

Q³ represents a structural fragment of formula Ib, Id, Ie or If; and

Het¹, R¹ᵃ, D, A, E, R²ᵃ, R²ᵇ, A and the structural fragments of formulae Ia, Ib, Ic, Id, Ie and If are as hereinbefore defined;

provided that:

(a) at least one of Q¹, Q² and Q³ represents a structural fragment of formula Id, Ie or If; and (b) at least one of R⁶ or R⁷, R⁸, R⁹, R¹⁰ and R¹¹ (whichever is/are present) represents branched, cyclic or part cyclic $C_{3-5}$ alkyl.

or a pharmaceutically acceptable derivative thereof, which compounds are also referred to hereinafter as "the compounds of the invention".

Compounds of formula II that may be mentioned include those in which at least one of R⁷, R⁸, R⁹, R¹⁰ and R¹¹ (whichever is/are present) represents branched, cyclic or part cyclic $C_{3-5}$ alkyl.

Preferred compounds of formula II include those in which:

Q¹ represents a structural fragment of formula Ic, or, particularly, a is structural fragment of formula Ib, Ie or If, or, when R¹ represents methyl or D-A-N(H)-Q³-Q²-Q¹-C(O)-E-C(O)—, then Q¹ may also be absent;

Q² represents a structural fragment of formula Ib in which G represents CH, or a structural fragment of formula Ie in which q represents 0;

Q³ represents a structural fragment of formula Id, Ie or If;

at least one of R⁷, R⁸, R⁹, R¹⁰ and R¹¹ (whichever is/are present) represents branched $C_{3-5}$ alkyl.

More preferred compounds of formula II include those in which:

$Q^1$ represents a structural fragment of formula Ie or, particularly, a structural fragment of formula Ib in which G represents CH, or, when $R^1$ represents methyl, then $Q^1$ may also be absent, or, when $R^1$ represents D-A-N(H)-$Q^3$-$Q^2$-$Q^1$-C(O)-E-C(O)—, then $Q^1$ is absent;

$Q^3$ represents a structural fragment of formula Ie.

at least one of $R^7$, $R^8$, $R^9$, $R^{10}$ and $R^{11}$ (whichever is/are present) represents isopropyl or isopentyl;

at least one of $R^7$, $R^8$, $R^9$, $R^{10}$ and $R^{11}$ (whichever is/are present) represents ethyl or, particularly, methyl.

Other preferred compounds of formula II include those in which:

$Q^1$ and $Q^3$ represent a structural fragment of formula Ib in which $R^6$ represents H and $R^7$ represents methyl; and $Q^2$ represents a structural fragment of formula Ib in which $R^6$ represents H and $R^7$ represents branched, cyclic or part cyclic $C_{3-5}$ alkyl (e.g. cyclopropylmethyl, cyclopentyl or, particularly, isopentyl or isopropyl).

In one embodiment of the invention, the compound of formula I or formula II may be one which comprises:

(a) at least one structural fragment of formula Ib in which G represents N and $R^6$ represents branched, cyclic or part cyclic $C_{3-5}$ alkyl (e.g. cyclopropylmethyl, isopentyl, cyclopentyl or, particularly, isopropyl);

(b) at least one structural fragment of formula Id in which p represents 0 and $R^9$ represents branched, cyclic or part cyclic $C_{3-5}$ alkyl (e.g. cyclopropylmethyl, isopentyl, cyclopentyl or, particularly, isopropyl); and/or, particularly (c) at least one structural fragment of formula Ie in which q represents 0 and $R^{10}$ represents branched, cyclic or part cyclic $C_{3-5}$ alkyl (e.g. cyclopropylmethyl, isopentyl, cyclopentyl or, particularly, isopropyl).

In this embodiment of the invention, the compound of formula I or formula II may particularly be one which comprises at least one structural fragment of formula Ie in which q represents 0 and $R^{10}$ represents isopropyl.

Compounds of formulae I and II that may be mentioned include those in which p, q and r, in whichever of structural fragments Id, Ie and If, respectively, are present, represent 0.

Preferred compounds of formulae I and II include those that bind to the minor groove of DNA.

Preferred compounds of the invention include those that have different binding affinities at different minor groove binding sites in double-stranded DNA molecules having more than one minor groove binding site.

When used herein, the term "different minor groove binding sites" includes references to minor grooves that differ with respect to sequences of base pairs that they contain (where the sequences may comprise AT base pairs, GC base pairs or mixtures thereof). However, the term also includes references to minor grooves that, although they may contain the same sequence of base pairs, or very similar sequences (e.g. sequences, such as those comprising solely AT base pairs, differing only with respect to the is order of the base pairs), they differ with respect to:

(a) the position of the sequence in the minor groove;
(b) the sequences of base pairs that are at one or both ends of the sequence correlating to the binding site;
(c) the pitch angle of base pairs in the minor groove;
(d) the width of the minor groove.

Compounds of the invention that may be mentioned include those that bind to and/or have specificity for DNA sequences that contain at least one GC base pairing.

When used herein, the term "bind to DNA sequences that contain at least one GC base pairing" refers to compounds that, although they bind to DNA minor grooves that contain AT base pairs only, they also bind to DNA minor grooves that contain at least one GC base pairing (i.e. the binding of the compounds to DNA is "tolerant" of the replacement of AT base pairs with GC base pairs).

When used herein, the term "specificity for DNA sequences that contain at least one GC base pairing" refers to compounds that bind with a measurably greater affinity to DNA minor grooves that contain at least one GC base pairing than they do to DNA minor grooves that contain AT base pairs only.

In relation to the above, affinity to DNA may be measured by techniques known to those skilled in the art, such as capillary electrophoresis, for example as described hereinafter. Furthermore, affinity to certain sections of DNA may be determined by techniques known to those skilled in the art, such as DNA footprinting, for example as described hereinafter.

In this respect, preferred compounds of the invention include:

(i) compounds of formula I, as hereinbefore defined, provided that the compound comprises at least one structural fragment of formula Id, Ie or If;

(ii) compounds of formula II, as hereinbefore defined.

Preferred compounds of the invention include the compounds of the Examples disclosed hereinafter.

Preparation

Compounds of the invention may be prepared using techniques (e.g. peptide synthesis) known to those skilled in the art, using starting materials that are either commercially available, are known in the literature, or may be obtained either by analogy with the processes described hereinafter, or by conventional synthetic procedures, in accordance with standard techniques; and appropriate reagents and reaction conditions.

According to the invention there is also provided a process for the preparation of compounds of formula I which comprises:

(a) reaction of a compound of formula III,

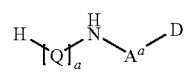

III wherein $A^a$ represents A or, when a represents 0, then $A^a$ may also represent $A^2$ and Q, D, A and $A^2$ are as hereinbefore defined and a is as defined below, with a compound of formula IV,

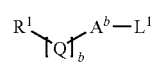

IV wherein $A^b$ represents a direct bond or -$A^1$-C(O)—, as appropriate, $L^1$ represents a suitable leaving group (e.g. halo, such as chloro, $C_{1-6}$ alkoxy, such as ethoxy, trichloromethyl, hydroxy or an alkoxy group (e.g. a benzyl alkoxy group) that is a functional group of a functionalized polymer (e.g. BALa-PAM resin, or derivatives thereof)), a and b both represent integers from 0 to 5, the sum of the two being 2, 3, 4 or 5, and $R^1$ and Q are as hereinbefore defined, for example under conditions known to those skilled in the art (for example: (i) when $L^1$ represents ethoxy, by reaction at between room and reflux temperature in the presence of ethanol; (ii) when $L^1$ represents halo, by reaction at between −10° C. and room temperature in the presence of a suitable base such as diisopropylamine and an appropriate solvent such as dichloromethane; (iii) when L¹ represents hydroxy, by reaction at around room temperature in the presence of an appropriate coupling agent such as HBTU (or a combination of a carbodiimide, such as diisopropylcarbodiimide, and HOBT), a suitable solvent such as DMF, and optionally in the presence of a tertiary amine base such as NMM; and (iv) when L¹ represents a benzyl alkoxy group derived from a BALa-PAM resin, by reaction at between room and reflux temperature (e.g. 55° C.) in the presence of a suitable solvent, such as THF); or (b) for compounds of formula I in which R¹ represents D-A-N(H)-[Q], —C(O)-E-C(O)—, reaction of two equivalents of a compound of formula V,

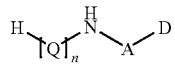

V wherein Q, n, A and D are as hereinbefore defined, with a compound of formula VI,

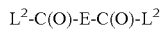

VI wherein L² represents a suitable leaving group (e.g. halo or, particularly, hydroxy), the two L² groups being the same or different, and E is as hereinbefore defined, for example under conditions known to those skilled in the art (e.g. as described in respect of process (a) above).

Compounds of formulae III, IV, V and VI, and derivatives thereof, are either commercially available, are known in the literature, or may be obtained either by analogy with the processes described herein, or by conventional synthetic procedures, in accordance with standard techniques, from readily available starting materials using appropriate reagents and reaction conditions.

Substituents on the aryl (e.g. phenyl), and heterocyclic, group(s) in compounds defined herein may be converted to other claimed substituents using techniques well known to those skilled in the art. For example, hydroxy may be converted to alkoxy, phenyl may be halogenated to give halophenyl, nitro may be reduced to give amino, halo may be displaced by cyano, etc.

The skilled person will also appreciate that various standard substituent or functional group interconversions and transformations within certain compounds of formula I will provide other compounds of formula I. For example, alkenylene may be reduced to alkylene, carbonyl may be reduced to hydroxy or methylene, etc.

The compounds of the invention may be isolated from their reaction mixtures using conventional techniques.

It will be appreciated by those skilled in the art that, in the process described above, the functional groups of intermediate compounds may be, or may need to be, protected by protecting groups.

Functional groups which it is desirable to protect include hydroxy, amino and carboxylic acid. Suitable protecting groups for hydroxy include trialkylsilyl and diarylalkylsilyl groups (e.g. tert-butytdimethylsilyl, tert-butyldiphenylsilyl or trimethylsilyl), tetrahydropyranyl and alkylcarbonyl groups (e.g. methyl- and ethylcarbonyl groups). Suitable protecting groups for amino include benzyl, tert-butyloxycarbonyl, 9-fluorenylmethoxycarbonyl or benzyloxy-carbonyl. Suitable protecting groups for carboxylic acid include $C_{1-6}$ alkyl or benzyl esters.

The protection and deprotection of functional groups may take place before or after any of the reaction steps described hereinbefore.

Protecting groups may be removed in accordance with techniques which are well known to those skilled in the art and as described hereinafter.

The use of protecting groups is fully described in "Protective Groups in Organic Chemistry", edited by J. W. F. McOmie, Plenum Press (1973), and "Protective Groups in Organic Synthesis", 3$^{rd}$ edition, T. W. Greene & P. G. M. Wutz, Wiley-Interscience (1999).

Persons skilled in the art will appreciate that, in order to obtain compounds of the invention in an alternative, and, on some occasions, more convenient, manner, the individual process steps mentioned herein may be performed in a different order, and/or the individual reactions may be performed at a different stage in the overall route (i.e. substituents may be added to and/or chemical transformations performed upon, different intermediates to those associated hereinbefore with a particular reaction). This will depend inter alia on factors such as the nature of other functional groups present in a particular substrate, the availability of key intermediates and the protecting group strategy (if any) to be adopted. Clearly, the type of chemistry involved will influence the choice of reagent that is used in the said synthetic steps, the need, and type, of protecting groups that are employed, and the sequence for accomplishing the synthesis.

Some of the intermediates referred to hereinbefore are novel. According to a further aspect of the invention there is thus provided a compound of formula V, or a protected derivative thereof.

Uses and Pharmaceutical Preparations

Compounds of the invention are useful because they possess pharmacological activity. They are therefore indicated as pharmaceuticals.

Thus, according to a further aspect of the invention there is provided the compounds of the invention for use as pharmaceuticals.

In particular, compounds of the invention bind to DNA, thereby inhibiting the binding to that DNA of an enzyme necessary for replication, with the effect that DNA replication is inhibited.

Thus, according to a further aspect of the invention there is provided a method of inhibiting DNA replication, which method comprises contacting the DNA with an inhibitory amount of a compound of the invention.

Due to their ability to inhibit DNA replication (e.g. by inhibiting transcription by blocking the binding or displacement of regulatory proteins or DNA-enzyme complexes, such as with reverse transcriptase or topoisomerases), compounds of the invention have utility in the treatment of diseases that rely upon DNA replication for their propagation. Such diseases include cancers and those involving viruses, bacteria, fungi or other microorganisms (e.g. diseases involving parasites, such as malaria).

Thus, according to a further aspect of the invention, there is provided a method of treatment of a disease that relies upon DNA replication for its propagation (e.g. cancer or a viral, bacterial, fungal or other microbial infection), which method comprises administration of a therapeutically effective amount of a compound of the invention to a person suffering from that disease. Such treatment may be particularly useful where the person suffering from that disease is immunocomprorised.

Because they have a different mode of action to many conventional anti-viral, anti-bacterial, anti-fungal or other anti-microbial (e.g. anti-parasitic) agents, compounds of the invention may be particularly useful in the treatment of viral, bacterial, fungal or other microbial (e.g. parasitic) infections where the infective agent is resistant to one or more anti-viral, anti-bacterial, anti-fungal or other anti-microbial (e.g. anti-parasitic) agents having a different mode of action. In this respect, according to a further aspect of the invention there is provided a method of treating a viral, bacterial, fungal or other microbial (e.g. parasitic) infection, where the viral, bacterial, fungal or other microbial (e.g. parasitic) infective agent is resistant to one or more anti-viral, anti-bacterial, anti-fungal or other anti-microbial (e.g. anti-parasitic) agents, respectively, that do not act by inhibiting DNA replication, which method comprises administration of a therapeutically effective amount of a compound of the invention to a person having that infection.

As well as having utility on their own in the treatment of diseases that rely upon DNA replication for their propagation, the compounds of the invention may be used in combination with one or more other compounds or treatment regimes that are used to treat such a disease. Thus, according to a further aspect of the invention, there is provided a method of treatment of a disease that relies upon DNA replication for its propagation (e.g. cancer or a viral, bacterial, fungal or other microbial infection), which method comprises administration, to a person suffering from that disease, of a therapeutically effective amount of a compound of the invention in combination with one or more other agents that are known to be effective in treating that disease.

When used herein, the term "in combination with" includes administration of the other agent(s) that is(are) known to be effective in treating the disease, before, during and/or following administration a compound of the invention. When more than one other agent is administered, the term also includes administration of the different other agents at different times relative to the time of administration of a compound of the invention.

Agents that are known to be effective in treating diseases that rely upon DNA replication for their propagation (e.g. anti-cancer, anti-viral, anti-bacterial, anti-fungal or other anti-microbial (e.g. anti-parasitic) agents) include those listed under the relevant headings in "*Martindale: The Complete Drug Reference*", 32$^{nd}$ Edition, the Pharmaceutical Press, London (1999), the disclosures of which document are hereby incorporated by reference.

Anti-cancer agents also include non-chemical agents such as ionizing radiation (e.g. subatomic particle radiation such as α-particles, β-particles, neutrons, protons, mesons and heavy ions or electromagnetic radiation such as high-frequency X-rays or gamma rays). Chemical anti-cancer agents that may be mentioned include:

(a) Alkylating agents including:
  (i) nitrogen mustards such as mechlorethamine ($HN_2$), cyclophosphamide, ifosfamide, melphalan (L-sarcolysin) and chlorambucil;
  (ii) ethylenimines and methylmelamines such as hexamethylmelamine, thiotepa;
  (iii) alkyl sulfonates and thiosulfonates such as busulfan, methyl methanesulfonate WS) and methyl methanethiosulfonate;
  (iv) nitrosoureas and nitrosoguanidines such as carmustine (BCNU), lomustine (CCNU), semustine (methyl-CCNU), streptozocin (streptozotocin) and N-methyl-N'-nitro-N-nitrosoguanidine (MNNG); and
  (v) triazenes such as dacarbazine (DTIC; dimethyltriazenoimidazole-carboxamide).

(b) Antimetabolites including:
  (i) folic acid analogues such as methotrexate (amethopterin);
  (ii) pyrimidine analogues such as fluorouracil (5-fluorouracil; 5-FU), floxuridine (fluorodeoxyuridine; FUdR) and cytarabine (cytosine arabinoside); and
  (iii) purine analogues and related inhibitors such as mercaptopurine (6-mercaptopurine; 6-MP), thioguanine (6-thioguanine; TG) and pentostatin (2'-deoxycoformycin).

(c) Natural Products including:
  (i) vinca alkaloids such as vinblastine (VLB) and vincristine;
  (ii) epipodophyllotoxins such as etoposide and teniposide;
  (iii) antibiotics such as dactinomycin (actinomycin A, C, D or F), daunorubicin (daunomycin; rubidomycin), doxorubicin, bleomycin, plicamycin (mithramycin) and mitomycin (mitomycin A, B or C);
  (iv) enzymes such as L-asparaginase; and
  (v) biological response modifiers such as interferon alphenomes.

(d) Miscellaneous agents including:
  (i) platinum coordination complexes such as cisplatin (cis-DDP) and carboplatin;
  (ii) anthracenedione such as mitoxantrone and anthracycline;
  (iii) substituted urea such as hydroxyurea;
  (iv) methyl hydrazine derivatives such as procarbazine (N-methylhydrazine, MIH);
  (v) adrenocortical suppressants such as mitotane (o,p'-DDD) and amlinoglutethimide;
  (vi) taxol and analogues/derivatives;
  (vii) hormone agonists/antagonists such as flutamide and tamoxifen;
  (viii) photoactivatable compounds (e.g. psoralens);
  (ix) DNA topoisomerase inhibitors (e.g. m-amsacrine and camptothecin);
  (x) anti-angiogenesis agents (e.g. SU6668, SU5416, combretastatin A4, angiostatin and endostatin); and
  (xi) immunotherapeutic agents (e.g. radiolabelled antibodies such as Bexxar™ and Theragyn™ (Pemtumomab™)).

Anti-viral agents that may be mentioned include acyclovir, gancyclovir, AZT, ddI, amantadine hydrochloride, inosine pranobex, vidarabine, and the like.

Anti-bacterial agents that may be mentioned include natural and synthetic penicillins and cephalosporins, sulphonamides, erythromycin, kanomycin, tetracycline, chloramphenicol, rifampicin and including gentamicin, ampicillin, benzypenicillin, benethamine penicillin, benzathine penicillin, phenethicillin, phenoxy-methyl penicillin, procaine penicillin, cloxacillin, flucloxacillin, methicillin sodium, amoxicillin, bacampicillin hydrochloride, ciclacillin, mezlocillin, pivampicillin, talampicillin hydrochloride, carfecillin sodium, piperacillin, ticarcillin, mecillinam, pirmecillinan, cefaclor, cefadroxil, cefotaxime, cefoxitin, cefsulodin sodium, ceftazidime, ceftizoxime, cefuroxime, cephalexin, cephalothin, cephamandole, cephazolin, cephradine, latamoxef disodium, aztreonam, chlortetracycline hydrochloride, clomocycline sodium, demeclocydine hydrochloride, doxycycline, lymecycline, minocycline, oxytetracycline, amikacin, framycetin sulphate, neomycin sulphate, netilmicin, tobramycin, colistin, sodium fusidate, polymyxin B sulphate, spectinomycin, vancomycin, calcium sulphaloxate, sulfametopyrazine, sulphadiazine, sulphadimidine, sulphaguanidine, sulphaurea, capreomycin, metronidazole, timidazole, cinoxacin, ciprofloxacin, nitrofurantoin, hexamine, streptomycin, carbenicillin, colistimethate, polymyxin B, furazolidone, nalidixic acid, trimethoprim-sulfamethoxazole, clindamycin, lincomycin, cycloserine, isoniazid, ethambutol, ethionamide, pyrazinamide and the like.

Anti-fungal agents that may be mentioned include miconazole, ketoconazole, itraconazole, fluconazole, fusidic acid, amphotericin, flucytosine, griseofulvin, natamycin, nystatin, and the like.

Anti-parasitic agents (e.g. anti-malarial agents) that may be mentioned include pyrimethamine, proguanil, chloroquine, primaquine, mefloquine, quinine, tetracycline, atovaquone, artemisinin, dihydroartemisinin, artemether, arteether, artesunic acid and its salts, and sulfonamides.

When a compound of the invention is administered to a patient in combination with one or more other agents that are known to be effective in treating diseases that rely upon DNA replication for their propagation, the compound of the invention and the other agent(s) may be administered separately or, conveniently, as a single composition. Thus, according to a further aspect of the invention, there is provided a combination product comprising components:

(A) a formulation comprising a compound of the invention; and
(B) a formulation comprising one or more other chemical agents that are known to be effective in treating diseases that rely upon DNA replication for their propagation.

The combination product according to this aspect of the invention provides for the administration of a compound of the invention in conjunction with one or more other chemical agents that are known to be effective in treating diseases that rely upon DNA replication for their propagation, and may thus be presented either as separate components (i.e. (A) and (B) separately), or may be presented (i.e. formulated) as a combined preparation (i.e. presented as a single formulation including a compound of the invention and one or more other chemical agents that are known to be effective in treating diseases that rely upon DNA replication for their propagation). When components (A) and (B) are presented as separate components, the combination product may alternatively be termed "a kit-of-parts".

In this aspect of the invention, other chemical agents that are known to be effective in treating diseases that rely upon DNA replication for their propagation include those referred to or mentioned hereinbefore. Thus, in a preferred embodiment of this aspect of the invention, the other chemical agents that are known to be effective in treating diseases that rely upon DNA replication for their propagation are one or more chemical anti-cancer, anti-viral, anti-bacterial, anti-fungal and/or anti-parasitic agents (e.g. the agents referred to or mentioned hereinbefore).

In a further preferred embodiment of this aspect of the invention, each of components (A) and (B) is formulated in admixture with a pharmaceutically-acceptable adjuvant, diluent or carrier.

The compounds of the invention will normally be administered orally, subcutaneously, intravenously, intraarterially, transdermally, intranasally, by inhalation, or by any other parenteral route, in the form of pharmaceutical preparations comprising the active ingredient either as a free base or a non-toxic organic or inorganic acid addition salt, in a pharmaceutically acceptable dosage form. Depending upon the disorder and patient to be treated, as well as the route of administration, the compositions may be administered at varying doses.

According to a further aspect of the invention there is thus provided a pharmaceutical formulation including a compound of the invention in admixture with a pharmaceutically acceptable adjuvant, diluent or carrier. Such formulations may be used for the treatment of diseases that rely upon DNA replication for their propagation. Thus, in one embodiment of this aspect of the invention there is provided a pharmaceutical formulation including, in admixture with a pharmaceutically acceptable adjuvant, diluent or carrier, a compound of the invention and one or more other chemical agents that are known to be effective in treating diseases that rely upon DNA replication for their propagation (e.g. one or more chemical anti-cancer, anti-viral, anti-bacterial, anti-fungal and/or anti-parasitic agents, such as the agents referred to or mentioned hereinbefore).

Suitable daily doses of the compounds of the invention in therapeutic treatment of humans are about 1 to 2000 mg/m$^2$.

The most effective mode of administration and dosage regimen for the compounds of the invention depends on several factors, including the particular condition being treated, the extent and localisation of that condition in the patient being treated, as well as the patient's state of health and their reaction to the compound being administered. Accordingly, the dosages of the compounds of the invention should be adjusted to suit the individual patient. Methods for determining the appropriate dose for an individual patient will be known to those skilled in the art.

As well as having utility in the treatment of diseases, compounds of the invention are also useful in various assay methods based upon DNA binding. For example, it is known that compounds that bind to the minor groove of DNA have the ability to stabilise DNA duplexes, as well as to stabilise a fully matched (in terms of base pairs) DNA duplex to a greater extent than a mismatched DNA duplex, thereby enabling easier discrimination between the fully matched and mismatched duplexes (e.g. in terms of the melting temperatures of the duplexes).

Thus, according to a further aspect of the invention, there is provided a method of stabilizing a DNA duplex formed between first and second single strands of DNA, which method comprises contacting that DNA duplex with a compound of the invention.

Further, there is also provided a method of enhancing the difference in melting temperatures between first and second DNA duplexes, wherein each DNA duplex is formed from a first single strand of DNA that is the same in each duplex and a second single strand of DNA that is different in each duplex, which method comprises contacting each DNA duplex with a compound of the invention. In a preferred embodiment, the first DNA duplex has a greater degree of base-pair matching (e.g. it is fully matched) than the second DNA duplex, which has at least one base-pair mismatch.

Compounds that stabilise fully matched DNA duplexes to a greater extent than mismatched DNA duplexes may be used to reduce levels of "false positive" results in DNA hybridization assay techniques, for example as described in U.S. Pat. No. 6,221,589, the disclosures of which are hereby incorporated by reference. The reduction in "false positive" results may be achieved through the use of more stringent conditions (e.g. higher wash temperatures) following a hybridization reaction in the presence of a duplex-stabilizing compound than is possible following a reaction in the absence of such a compound. Thus, there is further provided a method of increasing the maximum temperature of a wash following a DNA hybridization reaction, the method comprising the provision of a compound of the invention to the hybridization reaction mixture. When used herein, the term "maximum temperature of a wash following a DNA hybridization reaction" refers to the highest possible wash temperature that does not result in a substantial loss of the "true positive" results (i.e. the fully or most highly matched DNA duplexes).

When used herein in relation to the above-mentioned methods involving DNA duplexes, the term "contacting" includes admixing of a compound of the invention with a DNA duplex. However, the term also includes attaching (e.g. covalently bonding) a compound of the invention (e.g. a compound of the invention bearing a haloalkyl group), or a derivative thereof (e.g. a compound of formula V) that bears a functional group (e.g. a hydroxy, amino or carboxylic acid group) that may be used to form a suitable attachment, to one or both of the single strands of DNA that form the duplex. Such "labelled" single strands of DNA may be used as primers, capture probes, or in a number of different assays (e.g. capture-detection assays, 5'-nuclease assays and Beacon assays).

Compounds of the invention have the advantage that, compared to corresponding compounds that, in place of the essential branched, cyclic or part cyclic $C_{3-5}$ alkyl groups of the compounds of the invention, bear methyl substituents (for example compounds known in the prior art), they have a greater affinity and/or selectivity for any given DNA sequence. For example, compared to compounds known in the prior art, compounds of the invention have the advantage that they bind to DNA minor grooves that contain certain DNA sequences (e.g. sequences comprising AT base pairs only) with a measurably greater affinity and/or selectivity.

Compounds of the invention have the advantage in that they can bind to DNA sequences containing AT base pairs only, GC base pairs only, or mixtures of AT and GC base pairs. However, for pharmaceutical applications compounds of the invention (e.g. compounds of formula I comprising at least one structural fragment of formula Id, If or, particularly, Ie, or compounds of formula II) have the further advantage that, compared to corresponding compounds known in the prior art, they bind to DNA minor grooves that contain at least one GC base pairing with a measurably greater affinity and/or selectivity.

Compounds of the invention may also have the advantage that they may be more efficacious than, be less toxic than, have a broader range of activity than, be more potent than, be longer acting than, produce fewer side effects than, be more easily absorbed than, or that they may have other useful pharmacological properties over, compounds known in the prior art.

DESCRIPTION OF THE FIGURES

FIGS. 1 to 6

Capillary electrophoresis was used to study of ligand-DNA binding (see: (i) Hamdan, I. I.; Skellern, G. G.; and Waigh, R. D. "Separation of pd(GC)12 from pd(AT)12 by free solution capillary electrophoresis", *J. Cromatogr. A*. 806, 165-168 (1998); (ii) Hamdan, I. I.; Skellern, G. G.; and Waigh, R. D. "Use of capillary electrophoresis in the study of ligand-DNA interactions", *Nucleic Acids Research* 26, 3053-3058 (1998); (iii) Hamdan, I. I.; Skellern, G. G.; and Waigh, R. D. "Ligand binding to oligonucleotides" *Methods in Molecular Biology*, Vol. 163, "Capillary Electrophoresis of Nucleic acids", Vol 2, pages 379-391, K. R. Mitchelson and J. Cheng Eds., Humana Press, New Jersey, (2000)).

Typically, ligand binding results in a change in migration time of the DNA and sometimes a change in peak shape.

The following are shown in FIGS. 1-6:
(a) the experimental conditions, including the DNA sequence (s);
(b) the result of sequential addition of ligand; and
(c) the structure of the ligand being investigated.

Key to FIGS. 1 to 6:
r0=electropherogram in the absence of drug
rX=(where X is 0.5, 1, 2, 3 or 4) electropherogram in the presence of drug, where the drug:DNA ratio (in terms of concentration) is X:1

As can be seen from the figures, the disappearance of a peak corresponding to uncomplexed DNA relates to a measured ratio (rX) of drug to DNA.

This ratio corresponds to the binding ratio.

Double-stranded DNA oligonucleotides having, on one strand, nucleotide sequences AAATTATATTAT (SEQ ID NO:1) (peak 1) and GGGCCGCGCCGC (SEQ ID NO:2) (peak 2) are incubated in the presence of netropsin, a well-documented AT-selective binder. At r0, the two strands are present without any of the drug. At r1, the presence of netropsin (20 µM) causes a new peak (the complex of netropsin and the AT dodecamer) to appear in the trace. Increasing the amount of netropsin in the mixture to 40 µM (r2) causes complete conversion of the free AT dodecamer to its complex with netropsin.

From the traces shown in FIG. 1, it can be determined that:
(i) netropsin is AT selective; and
(ii) it has a binding ratio of 2:1 (drug:DNA) with AAAT-TATATTAT (SEQ ID NO:1) (1 drug molecule to each available binding site).

FIG. 2: Binding studies with 12/41 (the compound of Example 2) Compound 12/41 shows, with AAATTATATTAT (SEQ ID NO:1), the same 2:1 binding ratio as netropsin (as well as similar AT-selectivity).

FIG. 3: Binding studies with 13/20 (the compound of Example 3)

Figure 7:
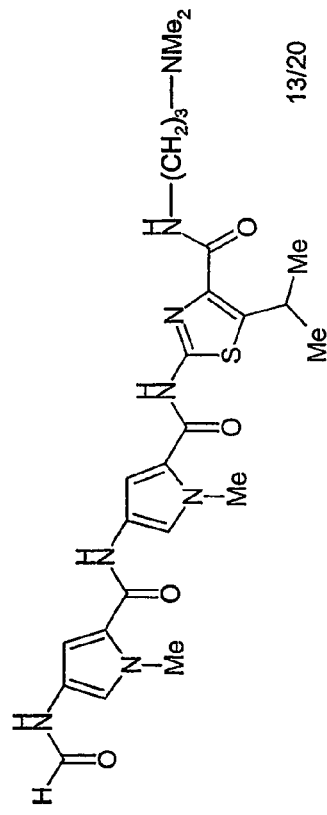

FIG. 3 presents the binding electropherograms of 13/20 in the presence of a double-stranded DNA decamer having, on one strand, the nucleotide sequence CGACTAGTCG (SEQ ID NO:3) the central part of which was indicated to be a high affinity binding site from footprinting studies (see FIG. 7). Here we see that the binding ratio is 4:1 (drug:DNA). This result demonstrates that 13/20 has a strong affinity for the given sequence, and also that the minor groove produced by the DNA decamer accommodates 4 drug-binding molecules in one binding site.

FIG. 4: Binding studies with distamycin

FIG. 4 presents the binding electropherograms of the well-known compound distamycin in the presence of the double-stranded DNA decamer having, on one strand, the nucleotide sequence CGACTAGTCG (SEQ ID NO:3). It can clearly be seen, distamycin has no affinity for the CGACTAGTCG (SEQ ID NO:3) sequence even at a drug to DNA ratio of 4:1 (the trace labelled r4).

FIG. 5: Competitive binding studies with compound 13/20

FIG. 5 presents the binding electropherograms for 13/20 in the presence of a mixture of double-stranded DNA oligonucleotides, one having, on one strand, the dodecameric nucleotide sequence AAATTATATTAT (SEQ ID NO:1) (peak 1) and the other having, on one strand, the decameric nucleotide sequence GGACTAGTCG (SEQ ID NO:4) (peak 2). It can be seen from the results that 13/20 has a greater affinity for the decamer ACTA sequence (as indicated by the earlier disappearance of the peak corresponding to the uncomplexed ACTA sequence).

FIG. 6: Further binding studies with compound 13/20

FIG. 6 presents the binding electropherograms of 13/20 incubated against the double-stranded DNA oligonucleotide having, on one strand, the decameric nucleotide sequence CCACTAGTGG (SEQ ID NO:5) The result obtained for this binding was identical with that achieved with the sequence in FIG. 3, showing that it is the central sequence which dominates binding, as indicated by footprinting.

FIGS. 7 and 8: DNA footprinting studies

DNA footprinting is a well-established technique in which a section of radio-labelled DNA (SEQ ID NO:6) is incubated with a chemical or biological cleaving agent, in the presence and absence of a putative binding ligand. Regions of ligand binding will show as blanks in the 'ladder'. Knowing the DNA sequence, the binding sites can then be deduced, from the location of these blanks.

The sequence shown in FIGS. 7 and 8 is MS1, which contains all possible four-base-pair binding sites. The procedure used in the footprinting experiments was analogous to that described in *J. Med. Chem.* 43, 3257 (2000), the disclosures of which document are hereby incorporated by reference. In an analogous manner to the procedure described in *J. Med. Chem.* 43, 3257 (2000), the MS1 sequence was labelled at the 3'-end with [α-$^{32}$P]dATP using reverse transcriptase. The agent used to cleave the radio-labelled DNA was DNase I.

Bases that fall within the "footprint" of a compound are indicated by XX . . . XX underneath the sequence. The binding domain that has been confirmed by capillary electrophoresis is indicated by XX. XX.

FIG. 7 shows the results for compound 13/20 (at a concentration of 0.03 μM), whereas FIG. 8 shows the results for compound 13/51 (at the concentrations indicated therein). As can be seen, at the concentration used in the experiment, compound 13/20 produces a footprint that is indicative of binding to only one site on the MS1 sequence. This binding site includes GC base pairs. In contrast, compound 13/51, at the concentrations indicated in FIG. 8, produced footprints over several different "AT-only" binding sites on the MS1 sequence.

Figure 9:
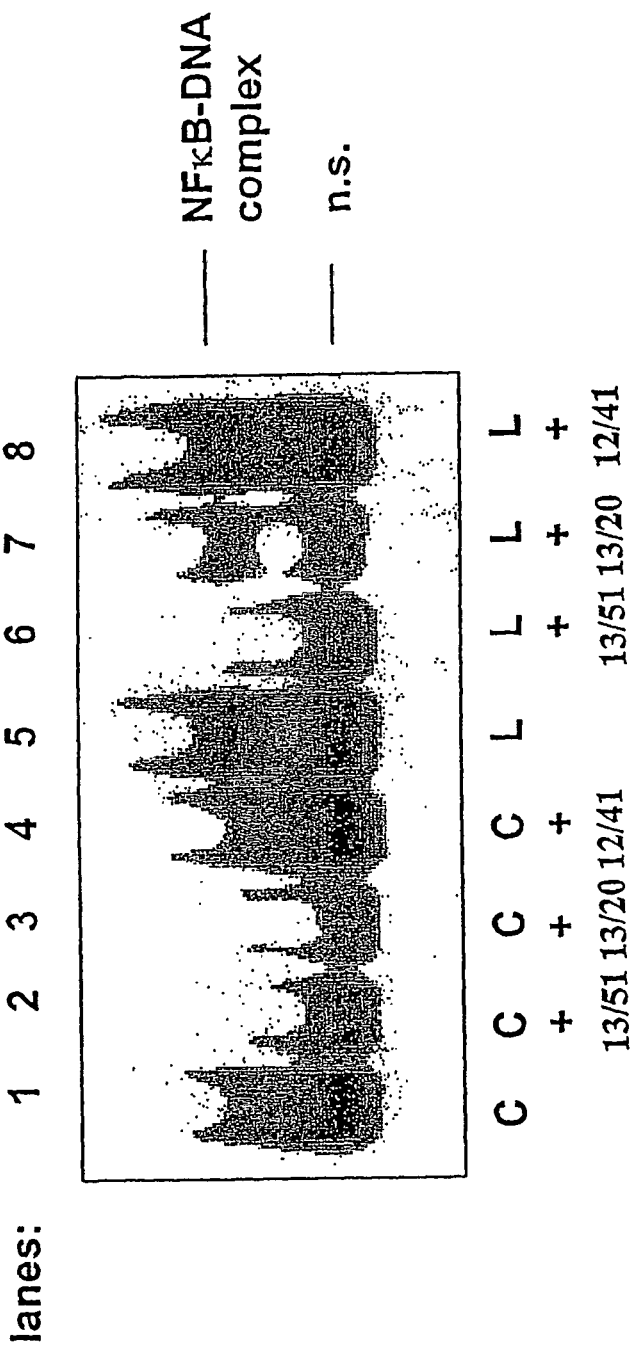

FIG. 9: DNA-Binding Assays with Compounds 12/41 and 13/20.

Murine macrophages (obtained and cultured as described in *Cell. Signal.* 11(7), 491 (1999), hereinafter referred to as "Reference 1", the disclosures of which document are hereby incorporated by reference) were exposed to vehicle (see Reference 1) or 1 μg/mL lipopolysaccharide (LPS; the active component of gram-negative endotoxin and a strong activator of the Nuclear Factor kappa B (NFκB) pathway; the particular LPS being obtained from *Salmonella minnesota*) for 1 hour and nuclear extracts prepared by standard procedures (see *Brit. J. Pharmacol.* 134, 393 (2001), hereinafter referred to as "Reference 2", the disclosures of which document are hereby incorporated by reference).

Aliquots of compounds (1 μL of a 1 mM solution) were incubated with 1 μL (0.035 pmol) of a $^{32}$P-labelled 20 bp double-stranded DNA oligonucleotide (representing the consensus binding sequence for NFκB proteins (see Reference 2 and *Brit. J. Pharmacol.* 134, 1629-1638 (2001), the disclosures of which latter document are hereby incorporated by reference)) for 30 min at room temperature. Following this, 5 μg of nuclear protein and buffer (the "gel-shift binding buffer" of Reference 2) were added (final volume 10 μL) and the samples incubated for a further 30 min at room temperature prior to their electrophoresis on pre-run non-denaturing polyacrylamide gels for 45-60 min (see Reference 2). Gels were then dried and exposed to X-ray film. The formation of NFκB protein-DNA complexes and potential inhibition of complex formation in the presence of the above compounds was detected by autoradiography.

In FIG. 9, lanes 1 to 4 show the results obtained where the nuclear protein was extracted from the macrophages exposed to vehicle, whereas lanes 5 to 8 show the results obtained where the nuclear protein was extracted from the macrophages exposed to LPS.

From the results presented in FIG. 9, it can be determined that exposure to lipopolysaccharide resulted in an increase in NFκB-DNA-binding activity (lane 1 vs. lane 5). Pre-incubation with the synthetic compounds had no effect upon basal DNA-binding activity (lane 1 vs. lanes 2 to 4). However, compounds 13/51 and 13/20 appeared to inhibit LPS-stimulated NFκB-DNA binding activity (lane 5 vs. lanes 6 and 7). In contrast, compound is 12/41 had little effect (lane 5 vs. lane 8).

Although compound 13/51, which does not bear a branched, cyclic or part cyclic $C_{3-5}$ alkyl substituent, appears to inhibit LPS-stimulated NFκB-DNA binding activity more strongly than does compound 13/20 (lane 6 vs. lane 7), this might well be expected from the lower binding specificity of compound 13/51 (compare FIGS. 7 and 8).

Biological Tests

Minimum inhibitory concentrations (MICs) against microorganisms (e.g. *S. Aureus, E. coli, S. faecalis, P. vulgaris,* MRSA, *Aspergillus niger, Candida albicans, Klebs. aerogenes, Ent. cloacae, Mycobacterium fortuitum* or *Aspergillus nidulans*) for compounds of the invention may be measured using procedures such as those described in A. J. Drummond and R. D. Waigh "The development of microbiological methods for phytochemical screening" *Recent Res. Devel. Phytochem.* 4, 143-152 (2000).

EXAMPLES

General Experimental Procedures

Electrospray mass spectra (ES-MS) were obtained on a Fisons® VG Platform Benchtop LC-MS. Electron impact (EI-MS) and fast atom bombardment (FAB-MS) mass spectra were obtained on a Jeol® JMS-AX505HA mass spectrometer.

NMR spectra were obtained on a Bruker® AMX 400 spectrometer operating at 400 MHz for $^1$H. In $^1$H NMR spectra, the abbreviation 'exch.' signifies that the relevant resonance disappeared on treatment of the solution with $D_2O$.

HPLC purification of the final products was carried out using a Vydac protein and peptide C18 column on a gradient eluting system. The solvents were A: water+0.1% trifluoroacetic acid (TFA), and B: acetonitrile+0.1% TFA.

IR spectra: solids were run as KBr discs and liquids as films, using a Nicolet® Impact 400D.

Column chromatography was performed with silica gel Prolabo® (200-400 mash).

Example 1

N-[5-({[5-({[3-(Dimethylamino)propyl]amino}carbonyl)-1-methyl-1H-pyrrol-3-yl]amino}carbonyl)-1-isopropyl-1-H-pyrrol-3-yl]-4-[(3,3-dimethylbutanoyl)amino]-1-methyl-1H-pyrrole-2-carboxamide (i) Ethyl 4-nitro-1H-pyrrole-2-carboxylate The sub-title compound was prepared according to a standard literature procedure (see: Ref. 1: W. J. Hale and W. V.

Hoyr, *J. Amer. Chem. Soc.* 37, 2538-2552 (1915); and Ref. 2: K. J. Morgan and D. P. Morrey, *Tetrahedron* 22, 57-62 (1966)).

(ii) Ethyl 1-isopropyl-4-nitro-1H-pyrrole-2-carboxylate

Ethyl 4-nitro-1H-pyrrole-2-carboxylate (1.039 g, 5.645 mmol; see step (i) above) was dissolved in DMF (40 mL, dry) to which was added potassium metal (384 mg, 9.831 mmol). The reaction mixture was heated to 100° C. and left at that temperature for 1 h with stirring. The reaction mixture was cooled to 50-60° C. then isopropyl bromide (1.224 g, 9.953 mmol) and potassium iodide (1.714 g, 10.327 mmol) were added and the reaction mixture was again heated with stirring to 100° C. for 5 h, and was then left stirring at room temperature overnight. The solvent was removed under reduced pressure and the residue was diluted with DCM and then extracted with water. The organic extract was dried over $MgSO_4$, filtered and the solvent removed under reduced pressure. The crude product obtained was chromatographed over silica gel eluted with 1/2 pet.ether/DCM. The material ($R_F$=0.26) was collected and the solvent removed under reduced pressure to give white crystalline solid (686 mg, 54% yield), m.p. 60-63° C.

Elemental Analysis:

Found: % C=53.19; % H=6.31; % N=12.30; Calculated for $C_{10}H_{14}N_2O_4$: % C=53.10; % H=6.24; % N=12.38. NMR (DMSO-$d_6$): 7.80(1H, d); 7.45(1H, d); 5.55-5.44(1H, qt); 4.36-4.27(2H, q); 1.51(6H, d); 1.40-1.34(3H, t). IR $v_{max}$ [KBr]: 1714, 1536, 1504, 1440, 1325, 1287, 1223, 1178, 1063 $cm^{-1}$.

(iii) 1-Isopropyl-4-nitro-1H-pyrrole-2-carboxylic acid

Ethyl 1-isopropyl-4-nitro-1H-pyrrole-2-carboxylate (656 mg, 2.900 mmol; see step (ii) above) was dissolved in ethanol (4 mL) to which was added a solution of NaOH (490 mg, 12.250 mmol in water (10 mL)). The reaction mixture was heated under reflux for 1.5 h and then the ethanol was removed under reduced pressure at 40° C. The reaction mixture was extracted with DCM (10 mL), and the water layer was collected, cooled to 0° C. with ice-water then acidified with $HCl_{conc}$ with stirring. The white solid material precipitated was filtered off, washed with water and dried under reduced pressure at 50° C. to give the required product (548 g, 95% yield), m.p. 194-195° C.

Elemental Analysis:

Found: % C=48.40; % H=4.85; % N=14.03; Calculated for $C_8H_{10}N_2O_4$: % C=48.48; % H=5.09; % N=14.13. NMR (DMSO-$d_6$): 8.37(1H, d); 7.27(1H, d); 5.47-5.36(1H, q); 1.44 (6H, d). IR $v_{max}$ [KBr]: 1676, 1541, 1517, 1483, 1411, 1370, 1250, 1188, 1077 $cm^{-1}$.

(iv) N-[5-({[3-(Dimethylamino)propyl]amino}carbonyl)-1-methyl-1H-pyrrol-3-yl]-1-isopropyl-4-nitro-1H-pyrrole-2-carboxamide N-[3-(Dimethylamino)propyl]-1-methyl-4-nitro-1H-pyrrole-2-carboxamide (816 mg, 3.209 mmol; see *Tetrahedron* 56, 5225-5239 (2000)) was suspended in a mixture of ethanol (30 mL) and HCl (7 mL, dil) to which was added Pd/C (517 mg, 10%) at room temperature. The reaction mixture was hydrogenated at room temperature and atmospheric pressure for 3.5 h. The catalyst was removed by filtration over Kieselguhr and then the solvent was removed under reduced pressure at 50° C. to give the amine as pale yellow solid. The product so formed was dissolved in water (10 mL) to which $NaHCO_3$ (2 g) was added. 1-Isopropyl-4-nitro-1H-pyrrole-2-carboxylic acid (548 mg, 2.631 mmol; see step (iii) above) was dissolved in DME (6 mL, dry) and thionyl chloride (3 mL), then heated under reflux for 2 h. The solvent was removed at room temperature to give the acid chloride which was dissolved in benzene (10 mL) and was added dropwise to the reaction mixture at room temperature with stirring. After addition of the acid chloride solution was finished the reaction mixture was heated under reflux for 30 min. then left to cool to room temperature overnight with continuous stirring. The reaction mixture was extracted with DCM (300 mL), dried and the solvent removed under reduced pressure to give yellow solid material. This material was triturated with a small amount of methanol and filtered to give pale yellow solid (318 mg). The filtrate was concentrated and chromatographed over silica gel using ethyl acetate/methanol/ammonia (49/49/2). Fractions with $R_f$ value of 0.3 were collected. The product was obtained as yellow solid (640 mg, 49% yield in total). M.p. 205-207° C.

Found: C, 56.25; H, 6.78; N, 20.59 Calculated for $C_{19}H_{28}N_6O_4$ C, 56.42; H, 6.98; N, 20.78%. $^1$H-NMR (DMSO-$d_6$) δ 1.42-1.57 (6H, d); 1.60-1.65 (2H, m); 2.12 (6H, s); 2.20-2.25 (2H, t); 3.17-3.22 (2H, q); 3.81 (3H, s); 5.40-5.51 (1H, m); 6.83 (1H, s); 7.22 (1H, s); 7.48 (1H, s); 8.11-8.15 (1H, t, CONH); 8.34 (1H, s); 10.29 (1H, s). IR $v_{max}$ [KBr]: 1640, 1555, 1506, 1480, 1322, 1279, 1240, 1203 $cm^{-1}$. ESMS: Found: 405.2 Calculated 405.5.

(v) N-[5-({[3-(Dimethylamino)propyl]amino}carbonyl)-1-methyl-1H-pyrrol-3-yl]-1-isopropyl-4-{[(1-methyl-4-nitro-1H-pyrrol-2-yl)carbonyl]-amino)}-1H-pyrrole-2-carboxamide N-[5-({[3-(Dimethylamino)propyl]amino}carbonyl)-1-methyl-1H-pyrrol-3-yl]-1-isopropyl-4-nitro-1H-pyrrole-2-carboxamide (272 mg, 0.672 mmol; see step (iv) above) and Pd/C (325 mg, 10%) were suspended in isopropanol (30 mL) and hydrogenated at room temperature and atmospheric pressure for 5 h. The catalyst was removed over Kieselguhr and the solvent removed under reduced pressure to give the amine as pale yellow solid, which was used without further purification. The amine was dissolved in THF (5 mL, dry) then 2,2,2-trichloro-1-(1-methyl-4-nitro-1H-pyrrol-2-yl)ethanone (183 mg, 0.674 mmol; see *Tetrahedron* 56, 5225-5239 (2000)) dissolved in THF (5 mL, dry) was added dropwise with stirring at room temperature. The stirring was continued overnight at room temperature. The solvent was removed under reduced pressure at room temperature to give the crude product, which was purified by silica gel column chromatography ethyl acetate/methanol/ammonia (49/49/2). Fractions containing the product at $R_f$ value of 0.3 were collected. The product was obtained as yellow solid material (221 mg, 63% yield) with no distinct melting point.

$^1$H-NMR(DMSO-$d_6$) δ 1.36-1.38 (6H, d); 1.64-1.71 (2H, m); 2.31 (6H, s); 3.16-3.22 (2H, q); 3.81 (3H, s); 3.96 (3H, s); 5.40-5.50 (1H, m); 6.85 (1H, d J 1.6 Hz); 6.93 (1H, d J 1.6 Hz); 7.18 (1H, d J 1.6 Hz); 7.43 (1H, d J 1.6 Hz); 7.58 (1H, d J 1.6 Hz); 8.07-8.10 (1H, t, CONH); 8.18 (1H, d J 1.6 Hz); 9.96 (1H, s); 10.29 (1H, s). IR $v_{max}$ [KBr]:1643, 1579, 1534, 1507, 1464, 1407, 1310, 1247 $cm^{-1}$. HRFABMS: Found: 527.27341 Calculated for $C_{25}H_{35}N_8O_5$ 527.27304.

(vi) N-[5-({[5-({[3-(Dimethylamino)propyl]amino}carbonyl)-1-methyl-1H-pyrrol-3-yl]amino}carbonyl)-1-isopropyl-1-H-pyrrol-3-yl]-4-[(3,3-dimethylbutanoyl)amino]-1-methyl-1H-pyrrole-2-carboxamide N-[5-({[3-(Dimethylamino)propyl]amino}carbonyl)-1-methyl-1H-pyrrol-3-yl]-1-isopropyl-4-{[(1-methyl-4-nitro-1H-pyrrol-2-yl)carbonyl]-amino)}-1H-pyrrole-2-carboxamide (100 mg, 0.189 mmol; see step (v) above) was dissolved in methanol (20 mL) to which was added Pd/C (114 mg, 10%). The reaction mixture was hydrogenated at room temperature and atmospheric pressure for 6.5 h. The catalyst was removed over Kieselguhr and the solvent removed under reduced pressure. The amine so formed was dissolved in DCM (10 mL, dry) to which was added a solution of 3,3-dimethylbutanoyl chloride (35 µL, 0.260 mmol), which was dissolved in DCM (5 mL, dry). The addition was dropwise with stirring at room temperature. Di-isopropylamine was then added in one portion to the reaction mixture. Stirring was continued at room temperature overnight. The solvent was removed under reduced pressure and the crude product obtained was purified by column chromatography using silica gel and ethyl acetate/methanol/ammonia (49/49/2). The solvent was removed under reduced pressure and the solid material was dissolved in chloroform (100 mL) and extracted with (5%, 50 mL) $NaHCO_3$. The organic layer was dried over $Na_2SO_4$, filtered and the solvent removed to give the required product (84 mg, 75% yield) as yellow glassy material with no distinct melting point.

$^1$H-NMR(CDCl$_3$): δ 1.03 (9H, s); 1.29-1.32 (6H, d); 1.68-1.83 (2H, m); 2.15 (2H, s); 2.19 (6H, s); 2.26-2.39 (2H, t); 3.39-3.46 (2H, q); 3.83 (3H, s); 3.84 (3H, s); 5.42-5.51 (1H, m); 6.47 (1H, d J 1.4 Hz); 6.58 (1H, d J 1.4 Hz); 6.67 (1H, d J 1.4 Hz); 7.05 (1H, d J 1.4 Hz); 7.22 (1H, d J 1.4 Hz); 7.37 (1H, d J 1.4 Hz); 7.78 (1H, t CONH); 7.82 (1H, s); 8.18 (1H, s); 8.32 (1H, s). IR $ν_{max}$ [KBr]: 3298, 2960, 1644, 1582, 1538, 1405, 1250 cm$^{-1}$. ES-MS: Found: M$^+$ 595.1 Calculated for $C_{31}H_{46}N_8O_4$ M$^+$ 595.4.

Example 2

N-[5-({[5-({[3-(Dimethylamino)propyl]amino}carbonyl)-1-methyl-1H-pyrrol-3-yl]amino}carbonyl)-1-isopropyl-1H-pyrrol-3-yl]-4-(formylamino)-1-methyl-1H-pyrrole-2-carboxamide N-[5-({[3-(Dimethylamino)propyl]amino}carbonyl)-1-methyl-1H-pyrrol-3-yl]-1-isopropyl-4-{[(1-methyl-4-nitro-1H-pyrrol-2-yl)carbonyl]-amino}-1H-pyrrole-2-carboxamide (102 mg, 0.194 mmol; see Example 1, step (v) above) was dissolved in methanol (20 mL), to which was added Pd/C (106 mg, 10%). The reaction mixture was hydrogenated for 5 h at room temperature and atmospheric pressure. The catalyst was removed over Kieselguhr and then ethyl formate (10 mL) was added to the filtrate. The reaction mixture was then heated until reflux for 72 h. The solvent was removed under reduced pressure and the crude product obtained was purified by HPLC. The product was obtained as white solid material after freeze-drying (64 mg, 51% yield as TFA salt).

$^1$H-NMR(DMSO-d$_6$) δ1.35-1.37(6H, d); 1.81-1.85(2H, m); 2.78-2.79(6H, d); 3.05(2H, m); 3.23-3.25(2H, q); 3.81 (3H, s); 3.84(3H, s); 5.40-5.46(1H, m); 6.92(1H, s); 6.94(1H, s); 6.96(1H, s); 7.17(1H, s); 7.19(1H, s); 7.38(1H, s); 8.12 (1H, s); 8.15(1H, t, CONH); 9.3(1H, broad, TFA); 9.85(1H, s); 9.91(1H, s); 10.05(1H, s). IR $ν_{max}$ [KBr]: 1673, 1644, 1582, 1540, 1470, 1441, 1402, 1204, 1139 cm$^{-1}$. ES-MS: Found: M$^+$ 524.9 Calculated 525.6.

Example 3

N-[3-(Dimethylamino)propyl]-2-({[4-({[4-(formylamino)-1-methyl-1H-pyrrol-2-yl]carbonyl}amino)-1-methyl-1H-pyrrol-2-yl]carbonyl}amino)-5-isopropyl-1,3-thiazole-4-carboxamide (i) Methyl 2-amino-5-isopropyl-1,3-thiazole-4-carboxylate
The sub-title compound was prepared in 41% yield according to the procedure described in *J. Chem. Soc., Perkin Trans. I* 159 (1982).
m.p. 151-152° C. (Lit. 150-151° C.).

(ii) Methyl 5-isopropyl-2-{[(1-methyl-4-nitro-1H-pyrrol-2-yl)carbonyl]-amino}-1,3-thiazole-4-carboxylate
1-Methyl-4-nitro-1H-pyrrole-2-carboxylic acid (520 mg, 3.057 mmol; see *Tetrahedron* 56, 5225-5239 (2000)) was dissolved in thionyl chloride (10 mL). The reaction mixture was heated under reflux overnight. Excess thionyl chloride was removed under reduced pressure to give the acid chloride, which was used without further purification. The acid chloride was dissolved in DCM (20 mL, dry), to which NMM (1.214 g, 12.000 mmol). The reaction mixture was cooled to 0° C. and kept under N$_2$. A solution of methyl 2-amino-5-isopropyl-1,3-thiazole-4-carboxylate (0.612 g, 3.057 mmol; see step (i) above) in DCM (20 mL, dry) was then added dropwise with stirring over a period of 10 min. The temperature was left to rise to room temperature overnight. DCM (10 mL) was added to the reaction mixture then HCl (50 mL, dil.) was added and the reaction mixture was extracted. The organic layer was washed with brine (50 mL), dried over MgSO$_4$ and the solvent removed under reduced pressure to give the crude product. Column chromatography over flash silica gel [1/1 ethyl acetate/pet.ether] gave the required product as white crystalline solid (460 mg, 43% yield), m.p. 118-120° C. (softening).

NMR(CDCl$_3$): 1.33-1.35(6H, CH—(CH$_3$)$_2$, d, J=6.4 Hz); 3.89(3H, s, CO$_2$Me); 4.09(3H, s, NMe); 4.11-4.18(1H, m); 7.24(1H, pyrrole, d, J=1.4 Hz); 7.67(1H, pyrrole, d, J=1.4 Hz); 9.85(1H, broad, CONH, exch.). IR $ν_{max}$ [KBr]: 3557, 3119, 2975, 1712, 1646, 1574, 1509, 1319, 1208 cm$^{-1}$. HREIMS: Found: 352.08579 calculated for $C_{14}H_{16}N_4O_5S$ 352.08414.

(iii) 5-Isopropyl-2-{[(1-methyl-4-nitro-1H-pyrrol-2-yl)carbonyl]amino}-1,3-thiazole-4-carboxylic acid
Methyl 5-isopropyl-2-{[(1-methyl-4-nitro-1H-pyrrol-2-yl)carbonyl]amino}-1,3-thiazole-4-carboxylate (480 mg, 1.363 mmol; see step (ii) above) was suspended in ethanolic KOH (0.5 M, 25 mL). The reaction mixture was heated under reflux for 4 h, then cooled to 0° C. HCl (conc.) was added dropwise with stirring until pH 2. The pale yellow solid obtained was filtered off, washed with de-ionised water and dried under reduced pressure at 45° C. overnight to give the required material (440 mg, 96% yield), m.p. 315-319° C.[decomp.].

NMR(DMSO-d$_6$) 1.23-1.25(6H, CH—(CH$_3$)$_2$, d, J=6.4 Hz); 3.98(3H, s, NMe); 4.01-4.08(1H, m); 7.99(1H, pyrrole, d, J=1.4 Hz); 8.29(1H, pyrrole, d, J=1.4 Hz); 12.5-13.2(1H, broad, CO$_2$H, exch.). IR $ν_{max}$ [KBr]: 3189, 3132, 2972, 1668, 1566, 1537, 1512, 1497, 1319, 1231 cm$^{-1}$. HRFABMS: Found: 337.06396 calculated for $C_{13}H_{13}O_5N_4S$ 337.06067

(iv) N-[3-(Dimethylamino)propyl]-5-isopropyl-2-{[(1-methyl-4-nitro-1H-pyrrol-2-yl)carbonyl]amino}-1,3-thiazole-4-carboxamide
5-Isopropyl-2-{[(1-methyl-4-nitro-1H-pyrrol-2-ylcarbonyl]amino}-1,3-thiazole-4-carboxylic acid (440 mg, 1.301 mmol; see step (iii) above) was suspended in thionyl chloride (6 mL) and heated until reflux for 3 h. Solvent (excess thionyl chloride) was removed under reduced pressure and the acid chloride so formed was dissolved in THF (20 mL, dry) then NMM (330 µL) was added. A solution of 3-(dimethylamino)propylamine (270 mg, 2.602 mmol) in THF (5 mL, dry) was added dropwise with stirring at room temperature under nitrogen. The stirring was continued at room temperature overnight. The solvent was removed under reduced pressure and the residue was purified by column chromatography using (1:1 methanol/ethyl acetate containing 1% TEA). The product was obtained as yellow glassy material (159 mg, 29% yield), m.p. 85-90° C. [softening].

NMR(CDCl$_3$): 1.27-1.29(6H, CH—(CH$_3$)$_2$, d, J=6.4 Hz); 1.79-1.86(2H, CH$_2$, qt, J=6.9 Hz); 2.31(6H, s, NMe$_2$); 2.45-2.49(2H, CH$_2$, t, J=6.9 Hz); 3.44-3.50(2H, CH$_2$, q, J=6.9 Hz); 4.10(3H, s, NMe); 4.38-4.45(1H, CH(CH$_3$)$_2$), m); 7.56(1H, pyrrole, d, J=1.4 Hz); 7.62(1H, s, CONH, exch.); 7.69(1H, pyrrole, d, J=1.4 Hz). IR $v_{max}$[KBr]: 3131, 2959, 1668, 1551, 1500, 1418, 1310, 1286 cm$^4$. HREIMS: Found: 422.17695 calculated for C$_{18}$H$_{26}$O$_4$N$_6$S 422.17363.

(v) N-[3-(Dimethylamino)propyl]-5-isopropyl-2-{[(1-methyl-4-{[(1-methyl-4-nitro-1H-pyrrol-2-yl)carbonyl]amino}-1H-pyrrol-2-yl)carbonyl]-amino}-1,3-thiazole-4-carboxamide N-[3-(Dimethylamino)propyl]-5-isopropyl-2-{[(1-methyl-4-nitro-1H-pyrrol-2-yl)carbonyl]amino}-1,3-thiazole-4-carboxamide (159 mg, 0.376 mmol; see step (iv) above) was dissolved in methanol (25 mL), cooled with ice, and then Pd/C (158 mg, 10%) was added under nitrogen. The reaction mixture was hydrogenated for 4 h at room temperature and atmospheric pressure. The catalyst was removed over Kieselguhr and the solvent was then removed under reduced pressure to give the amine. This amine was dissolved in THF (25 mL, dry) to which was added 2,2,2-trichloro-1-(1-methyl-4-nitro-1H-pyrrol-2-yl)ethanone (134 mg, 0.494 mmol; see *Tetrahedron* 56, 5225-5239 (2000)) dissolved in THF (5 mL, dry), dropwise with stirring, at room temperature. Stirring was continued at room temperature overnight. The solvent was removed under reduced pressure and the residue was chromatographed using 49/49/2 methanol/ethyl acetate/TEA. The product obtained was dissolved in DCM and extracted with a solution of sodium carbonate (10 mL, 5%), then dried and the solvent removed under reduced pressure. The product was obtained as yellow solid (90 mg, 44% yield). M.p. 138-141° C.

$^1$H-NMR(DMSO-d$_6$) δ 1.26 & 1.28(6H, d, 2xMe); 1.65 (2H, m, CH$_2$); 2.19(6H, s, NMe$_2$); 2.32(2H, t, CH$_2$); 3.26(2H, q, CH$_2$); 3.90(3H, s, NMe); 3.97(3H, s, NMe); 4.19(1H, m, CH); 7.36(1H, d, PyrH); 7.47(1H, d, pyrH); 7.62(1H, d, PyrH); 7.81(1H, t, CONH exch.); 8.19(1H, d, PyrH); 10.35 (1H, s, CONH exch.); 12.10(1H, broad exch.). IR $v_{max}$[KBr]: 1651, 1552, 1506, 1464, 1421, 1398, 1311, 1288, 1202 cm$^{-1}$. HRFABMS: Found: 545.22931 Calculated for C$_{24}$H$_{33}$N$_8$O$_5$S 545.22946.

(vi) N-[3-(Dimethylamino)propyl]-2-({[4-({[4-(formylamino)-1-methyl-1H-pyrrol-2-yl]carbonyl}amino)-1-methyl-1H-pyrrol-2-yl]carbonyl}amino)-5-isopropyl-1,3-thiazole-4-carboxamide N-[3-(Dimethylamino)propyl]-5-isopropyl-2-{[(1-methyl-4-{[(1-methyl-4-nitro-1H-pyrrol-2-yl)carbonyl]amino}-1H-pyrrol-2-yl)carbonyl]amino}-1,3-thiazole-4-carboxamide (90 mg, 0.165 mmol; see step (v) above) was suspended in ethanol (20 mL) then Pd/C (97 mg, 10%) was added at 0° C. under nitrogen. The reaction mixture was hydrogenated at room temperature and atmospheric pressure for 5 h. The catalyst was removed under reduced pressure then ethyl formate (20 mL) was added to the ethanolic solution of the amine. The reaction mixture was heated under reflux for 3 days, then the solvent was removed under reduced pressure. The crude product was dissolved in water (2 mL) containing 0.1% TFA, then purified by HPLC. The fractions collected were freeze-dried to give the desired product as pale yellow solid (55 mg, 51%) with no distinct m.p.

$^1$H-NMR(DMSO-d$_6$) δ 1.27-1.29(6H, d, J=6.9 Hz), 1.86 (2H, m), 2.78-2.79(6H, d, J=4.0 Hz), 3.07(2H, m), 3.37(2H, m), 3.84(3H, s), 3.88(3H, s), 4.19(1H, m), 6.94(1H, d, J=1.6 Hz), 7.19(1H, s), 7.38(1H, s), 7.40(1H, s), 7.96(1H, t), 8.13 (1H, d, J=1.6 Hz), 9.30(1H, broad, TFA), 9.99(1H, s), 10.04 (1H, s), 12.02(1H, s). IR $v_{max}$[KBr]: 1664, 1555, 1465, 1399, 1294, 1209, 1130 cm$^{-1}$. HRFABMS: Found: 544.25962 Calculated for C$_{25}$H$_{36}$N$_8$O$_4$S 544.25802

Example 4

N-[5-({[3-(Dimethylamino)propyl]amino}carbonyl)-1-isopropyl-1H-pyrrol-3-yl]-4-({[4-(formylamino-1-isopropyl-1H-pyrrol-2-yl]carbonyl}amino)-1-isopropyl-1H-pyrrole-2-carboxamide (i) N-[3-(Dimethylamino)propyl]-1-isopropyl-4-nitro-1H-pyrrole-2-carboxamide 1-Isopropyl-4-nitro-1H-pyrrole-2-carboxylic acid (312 mg, 1.574 mmol; see Example 1, step (iii) above) was dissolved in thionyl chloride (5 mL) and heated until reflux for 4 h. The excess thionyl chloride was removed under reduced pressure at 50° C. to give the acid chloride as white solid material that was used without further purification. 3-(Dimethylamino)propylamine (250 µL) was dissolved in THF (250 mL, dry) to which NMM (250 µL) was added at room temperature with stirring. The acid chloride was dissolved in THF (5 mL, dry) and added dropwise to the amine solution at room temperature with stirring. The reaction mixture was then left stirring at room temperature overnight. Following this the solvent was removed under reduced pressure at 50° C. and then the crude product was extracted with K$_2$CO$_3$ (25 mL, 10%) and DCM (2×50 mL). The organic layer was collected, dried over Na$_2$SO$_4$, filtered and the solvent removed under reduced pressure. The crude product was purified by chromatography over silica gel using 49.5:49.5:1 methanol/ethyl acetate/TEA to give the product as pale yellow oil, R$_f$=0.25, (400 mg, 90% yield).

NMR(CDCl$_3$): 1.46&1.48(6H, d, J=6.7 Hz), 1.71-1.77 (2H, qt, J=6.0 Hz), 2.32(6H, s), 2.51(2H, t, J=5.7 Hz), 3.49 (2H, qt, J=5.0 Hz), 5.62(1H, qt, J=6.7 Hz), 6.92(1H, d, J=1.6 Hz), 7.73(1H, d, J=1.6 Hz), 8.58(1H, s). IR $v_{max}$[KBr]: 3330, 3136, 2979, 1650, 1535, 1430, 1279, 1258 cm$^{-1}$. HREIMS: Found: 282.16908 Calculated for C$_{13}$H$_{22}$N$_4$O$_3$ 282.16919

(ii) N-[5-({[3-Dimethylamino)propyl]amino}carbonyl)-1-isopropyl-1H-pyrrol-3-yl]-1-isopropyl-4-nitro-1H-pyrrole-2-carboxamide N-[3-(Dimethylamino)propyl]-1-isopropyl-4-nitro-1H-pyrrole-2-carboxamide (400 mg, 1.417 mmol; see step (i) above) was dissolved in ethanol (20 mL) then cooled to 0° C. Pd/C-10% (343 mg) was added portion-wise under N$_2$ with stirring. The reaction mixture was hydrogenated at room temperature and atmospheric pressure for 4 h. The catalyst was removed over Kieselguhr, and the solvent removed under reduced pressure at 50° C. to give an oil which was used in the next step without further purification. 1-Isopropyl-4-nitro-1H-pyrrole-2-carboxylic acid (281 mg, 1.417 mmol; see Example 1, step (iii) above) was suspended in thionyl chloride (5 mL) then heated under reflux for 4 h. The excess thionyl chloride was removed under reduced pressure at 50° C. and then it was dissolved in THF (5 mL, dry). The amine was dissolved in TH (20 mL, dry) to which was added NMM (250 µL) followed by the acid chloride solution. The addition was dropwise at room temperature with stirring. The reaction mixture was left stirring at room temperature overnight. The solvent was removed under reduced pressure and the crude product dissolved in DCM (50 mL) and extracted with Na$_2$CO$_3$ (5%, 25 mL). The organic layer was dried over Na$_2$SO$_4$, filtered and the solvent removed under reduced pressure. The crude product was chromatographed over silica gel using 50:50:0.5 methanol/ethyl acetate/TEA. Fractions with $R_f$ value of 0.1 were collected. The solvent was removed at 50° C. under reduced pressure to give the product as yellow glassy material (471 mg, 77% yield), m.p. 86-90° C. (softening).

NMR(CDCl$_3$):1.42(6H, d, 6.7 Hz), 1.75(6H, d, J=6.7 Hz), 1.72-1.77(2H, m), 2.31(6H, s), 2.46(2H, t, J=6.1 Hz), 3.44-3.49(2H, q, J=6.0 Hz), 5.51-5.64(2H, m), 6.45(1H, d, 1.6 Hz), 7.17(1H, d, J=1.6 Hz), 7.40(1H, d, J=1.6 Hz), 7.69(1H, s, broad, CONH), 7.79(1H, d, J=1.6 Hz). IR $v_{max}$ [KBr]: 2974, 2927, 1636, 1574, 1531, 1507, 1407, 1282, 1237, 1170 cm$^{-1}$. HREIMS: Found: 432.24833 Calculated for $C_{21}H_{32}N_6O_4$ 432.24850

(iii) N-[5-({[3-(Dimethylamino)propyl]amino}carbonyl)-1-isopropyl-1H-pyrrol-3-yl]-1-isopropyl-4-{[(1-isopropyl-4-nitro-1H-pyrrol-2-yl)carbonyl]-amino}-1H-pyrrole-2-carboxamide N-[5-({[3-(Dimethylamino)propyl]amino}carbonyl)-1-isopropyl-1H-pyrrol-3-yl]-1-isopropyl-4-nitro-1H-pyrrole-2-carboxamide (209 mg, 0.483 mmol; see step (ii) above) was dissolved in ethanol (20 mL) at 0° C. with stirring. Pd/C-10% (180 mg) was added to the solution at 0° C. and under N$_2$ with stirring. The reaction mixture was hydrogenated for 4 h then the catalyst was removed by filtration over Kieselguhr and the solvent removed under reduced pressure at 50° C. to give the amine. 1-Isopropyl-4-nitro-1H-pyrrole-2-carboxylic acid (92 mg, 0.462 mmol; see Example 1, step (iii) above) was dissolved in thionyl chloride (3 mL) and heated under reflux for 3 h. Excess thionyl chloride was removed under reduced pressure at 50° C. to give the acid chloride. The amine was dissolved in THF (20 mL, dry) to which the acid chloride [dissolved in THF (20 mL, dry)] was added dropwise with stirring at room temperature. The reaction mixture was left stirring at room temperature overnight. The solvent was removed under reduced pressure and the crude product dissolved in DCM (2×50 mL) after which it was extracted with Na$_2$CO$_3$ (50 mL, 5%). The organic layer was dried and then the solvent removed. The crude product was chromatographed over silica gel using 49.5:49.5:1 ethyl acetate/methanol/TEA as eluant. The product was obtained as yellow glassy material $R_f$=0.15, (230 mg, 82% yield), m.p. 130-133° C. (softening).

NMR(CDCl$_3$): 1.43(6H, d, J=6.7 Hz), 1.47(6H, d, J=6.7 Hz), 1.52(6H, d, J=6.7 Hz), 1.73-1.79(2H, m), 2.32(6H, s), 2.47-2.50(2H, t, 6.1 Hz), 3.46-3.50(2H, q, 6.0 Hz), 5.53-5.61 (3H, m), 6.42(1H, d, J=1.6 Hz), 6.60(1H, d, J=1.6 Hz), 7.28 (1H, d, J=1.6 Hz), 7.40(1H, d, J=1.6 Hz), 7.41(1H, s), 7.44 (1H, s), 7.63(1H, s, broad, CONH), 7.81(1H, d, J=1.6 Hz), 8.02(1H, s). IR $v_{max}$ [KBr]: 2979, 2937, 1645, 1593, 1525, 1504, 1410, 1279, 1237, 1190 cm$^{-1}$. HRFABMS: Found: 583.33440 Calculated for $C_{29}H_{43}N_8O_5$ 583.33564

(iv) N-[5-({[3-(Dimethylamino)propyl]amino}carbonyl)-1-isopropyl-1H-pyrrol-3-yl]-4-({[4-(formylamino)-1-isopropyl-1H-pyrrol-2-yl]carbonyl}-amino)-1-isopropyl-1H-pyrrole-2-carboxamide N-[5-({[3-(Dimethylamino)propyl]amino}carbonyl)-1-isopropyl-1H-pyrrol-3-yl]-1-isopropyl-4-{[(1-isopropyl-4-nitro-1H-pyrrol-2-yl)carbonyl]amino}-1H-pyrrole-2-carboxamide (105 mg, 0.180 mmol; see step (iii) above) was suspended in ethanol (20 mL) to which Pd/C-10% (80 mg) was added under nitrogen at 0° C. The reaction mixture was hydrogenated at room temperature and atmospheric pressure for 4 h. The catalyst was removed over Kieselguhr and the ethanolic solution was then used in the second part of the experiment. Ethyl formate (20 mL) was added to the ethanolic solution of the amine. The reaction mixture was heated under reflux for 4 days. The solvents were removed under reduced pressure at 40° C. and then the crude product was purified by reverse phase HPLC. The fractions obtained were freeze-dried to give the required material as white solid (71 mg, 57% yield) as TFA salt with no distinct m.p.

NMR(DMSO-d$_6$): 1.14-1.36(18H, m), 1.82-1.91(2H, m), 2.78(6H, d, J=4.62 Hz), 3.04-3.09(2H, m), 3.22-3.26(2H, m), 5.42-5.51(3H, m), 6.82(1H, d, J=1.6 Hz), 5.89(1H, d, J=1.6 Hz), 6.97(1H, d, J=1.6 Hz), 7.35(1H, d, J=1.6 Hz), 7.34(1H, s), 8.12-8.14(2H, s&t), 9.25(1H, s, broad, TFA), 9.91(1H, s), 9.93(1H, s), 10.03(1H, s). IR $v_{max}$ [KBr]: 3285, 2953, 1650, 1580, 1525, 1460, 1402, 1260 cm$^-$. HREIMS: Found: 580.35047 Calculated for $C_{30}H_{44}O_4N_8$ 580.34855.

Example 5

N-[5-({[5-({[3-(Dimethylamino)propyl]amino}carbonyl)-1-isopentyl-1H-pyrrol-3-yl]amino}carbonyl)-1-isopentyl-1H-pyrrol-3-yl]-4-(formylamino-1-isopentyl-1H-pyrrole-2-carboxamide (i) Ethyl 1-isopentyl-4-nitro-1H-pyrrole-2-carboxylate Ethyl 4-nitro-1H-pyrrole-2-carboxylate (2.022 g, 10.983 mmol; see Example 1, step (i) above) was dissolved in DMF (30 mL, dry) to which potassium (0.569 g, 14.552 mmol) was added with stirring under nitrogen. The reaction mixture was heated at 100° C. for 1 h and then the temperature was allowed to reach 50° C. Isoamyl bromide (2.498 g, 16.538 mmol) was then added, followed by KI (2.197 g, 14.552 mmol). The temperature was raised to 100° C. and stirring continued for 5 h, after which time the temperature was allowed to return to room temperature. The reaction mixture was then stirred overnight, following which the solvent was removed under reduced pressure at 50° C. The crude product was dissolved in DCM and the salt extracted with water. The organic extract was dried over MgSO$_4$, filtered and the solvent removed under reduced pressure at 30° C. The crude product obtained was chromatographed over silica gel using 1/2 n-hexane/DCM as eluant. Material with $R_f$=0.3 was collected and the solvent was removed under reduced pressure to give white crystalline material (2.377 g, 85% yield). M.p. 46-47° C. (Lit. m.p. 46-47° C.).

Reference: Turchin, K. F.; Grokhovskii, S. L.; Zhuze, A. L.; Gottikh, B. P., *Soviet Journal of Bioorganic Chemistry (English Translation)* 1978, 4, 780-790.

NMR(CDCl$_3$): 0.97(6H, d, J=6.45 Hz), 1.38(3H, t, J=7.2 Hz), 1.61-1.73(3H, m), 4.30-4.39(4H, m), 7.43(1H, d, J=1.6 Hz), 7.63(1H, d, J=1.6 Hz). IR $v_{max}$ [KBr]: 3138, 2970, 1707, 1539, 1510, 1487, 1426, 1389, 1321, 1259, 1204, 1130, 1097 cm$^{-1}$.

(ii) 1-Isopentyl-4-nitro-1H-pyrrole-2carboxylic acid

Ethyl 1-isopentyl-4-nitro-1H-pyrrole-2-carboxylate (2.377 g, 9.329 mmol; see step (i) above) was suspended in ethanol (5 mL), then a solution of NaOH (955 mg dissolved in 20 mL of water) was added. The reaction mixture was reduced by half under reduced pressure at 50° C., and then the cooled solution was extracted with ether. The water layer was cooled to 0° C. then conc. HCl was added dropwise with vigorous stirring until pH 2. The white solid material was filtered off, washed with water, dried at 60° C. under reduced pressure for 2 h then left at room temperature overnight. The product was obtained as white solid (2.008 g, 95% yield), m.p. 154-157° C. [Lit.m.p. 154-156° C.].

Reference: Turchin, K. F.; Grokhovskii, S. L.; Zhuze, A. L.; Gottikh, B. P., *Soviet Journal of Bioorganic Chemistry (English Translation)* 1978, 4, 780-790.

NMR(CDCl$_3$): 0.98(6H, d, J=6.46 Hz), 1.62-1.75(3H, m), 4.38(2H, t, J=7.5 Hz), 7.58(1H, d, J=1.98 Hz), 7.69(1H, d, J=1.97 Hz). IR $\nu_{max}$ [KBr]: 3120, 1677, 1540, 1517, 1480, 1315, 1250 cm$^{-1}$.

(iii) N-[3-(Dimethylamino)propyl]-1-isopentyl-4-nitro-1H-pyrrole-2-carboxamide

1-Isopentyl-4-nitro-1H-pyrrole-2-carboxylic acid (315 mg, 1.388 mmol; see step (ii) above) was dissolved in thionyl chloride (5 mL) and the reaction mixture heated under reflux for 4 h. Excess thionyl chloride was removed under reduced pressure and the acid chloride so formed was used without further purification. 3-(Dimethylamino)propyl-amine (250 µL, 2.471 mmol) was dissolved in THF (20 mL, dry) to which NMM (250 µL, 2.472 mmol) was added. The acid chloride was dissolved in THF (5 mL, dry) then it was added dropwise to the amine solution at room temperature with stirring, which was continued at room temperature overnight. The solvent was removed under reduced pressure and the crude product dissolved in DCM (50 mL) then extracted with aqueous sodium carbonate (540 mg of Na$_2$CO$_3$ in 25 mL of water). The organic layer was dried over silica gel using 100:100:1 ethyl acetate/methanol/TFA to give the required product as pale yellow solid (R$_f$=0.15), (410 mg, 95% yield), m.p. 72-73° C.

NMR(CDCl$_3$): 0.95(6H, d, J=6.5 Hz), 1.57-1.76(5H, m), 2.32(6H, s), 2.51(2H. t, J=10.3 Hz), 3.47-3.51(2H, qt, J=4.8 Hz), 4.40-4.44(2H, q, J=7.5 Hz), 6.92(1H, d, J=1.88 Hz), 7.56(1H, d, J=1.90 Hz), 8.61(1H, s, broad, CONH). IR $\nu_{max}$ [KBr]: 1656, 1637, 1565, 1534, 1498, 1417, 1333 cm$^{-1}$. HREIMS: Found: 310.20031 Calculated for C$_{15}$H$_{26}$O$_4$N$_3$ 310.20049.

(iv) N-[3-(Dimethylamino)propyl]-1-isopentyl-4-{[(1-isopentyl-4-nitro-1H-pyrrol-2-yl)carbonyl]amino}-1H-pyrrole-2-carboxamide N-[3-(Dimethylamino)propyl]-1-isopentyl-4-nitro-1H-pyrrole-2-carboxamide (151 mg, 0.486 mmol; see step (iii) above) was dissolved in ethanol (20 mL). The reaction mixture was cooled to 0° C. then Pd/C-10% (98 mg) was added to the reaction mixture under N$_2$. The reaction mixture was then hydrogenated at room temperature and atmospheric pressure for 4 h. The catalyst was removed over Kieselguhr and the solvent removed under reduced pressure at 50° C. to give the amine as pale yellow oil that was used in the next step without further purification. 1-Isopentyl-4-nitro-1H-pyrrole-2-carboxylic acid (100 mg, 0.441 mmol; see step (ii) above) was dissolved in thionyl chloride (3 mL) and the reaction mixture heated under reflux for 4 h. Excess thionyl chloride was removed under reduced pressure at 50° C. and the acid chloride so formed was used without further purification. The amine was dissolved in THF (20 mL, dry) to which NMM (200 µL) was added at room temperature with stirring. The acid chloride was dissolved in THF (15 mL, dry) then added to the amine solution dropwise with stirring at room temperature. The stirring was continued at room temperature overnight. The solvent was removed under reduced pressure at 50° C., then the crude product was dissolved in DCM (50 mL) and extracted with sodium carbonate solution (612 mg in 20 mL of water). The organic layer was collected, dried and the solvent removed under reduced pressure. The crude product was purified by column chromatography using ethyl acetate/methanol/TEA 100:100:1 ratio. Fractions containing the required material were collected and the solvent was then removed under reduced pressure and co-evaporated with n-hexane to give the pure product as glassy yellow material R$_f$=0.34, (223 mg, 94% yield), m.p. 57-60° C. [Transparent].

NMR[CDCl$_3$]: 0.93(6H, d, J=4.5 Hz), 0.95(6H, d, J=4.5 Hz), 1.57-1.83(4H, m), 2.35(6H, s), 2.52(2H, t, J=6.1 Hz), 3.45-3.49(2H, q, J=5.6 Hz), 4.36(2H, t, J=7.4 Hz), 4.43(2H, t, J=7.4 Hz), 6.51(1H, d, J=1.9 Hz), 7.20(1H, d, J=1.9 Hz), 7.22(1H, d, J=1.9 Hz), 7.64(1H, d, J=1.9 Hz), 7.77(2H, s &t). IR $\nu_{max}$ [KBr]: 2953, 1633, 1592, 1573, 1539, 1525, 1503, 1312 cm$^{-1}$. HREIMS: Found: 488.31163 Calculated for C$_{25}$H$_{40}$O$_4$N$_6$ 488.31110.

(v) N-[5-({[5-({[3-(Dimethylamino)propyl]amino}carbonyl)-1-isopentyl-1H-pyrrol-3-yl]amino}carbonyl)-1-isopentyl-1H-pyrrol-3-yl]-1-isopentyl-4-nitro-1H-pyrrole-2-carboxamide N-[3-(Dimethylamino)propyl]-1-isopentyl-4-{[(1-isopentyl-4-nitro-1H-pyrrol-2-yl)carbonyl]amino}-1H-pyrrole-2-carboxamide (200 mg, 0.410 mmol; see step (iv) above) was dissolved in ethanol (20 mL) at 0° C. Pd/C-10° C. (164 mg) was added to the reaction mixture at 0° C. and under N$_2$. The reaction mixture was hydrogenated at room temperature and atmospheric pressure for 4 h. The catalyst was removed over Kieselguhr and the solvent removed under reduced pressure to give the amine, which was used in the next step without further purification. 1-Isopentyl-4-nitro-1H-pyrrole-2-carboxylic acid (110 mg, 0.485 mmol; see step (ii) above) was dissolved in thionyl chloride (3 mL) and heated under reflux for 3 h. Excess thionyl chloride was removed under reduced pressure to give the acid chloride that was used without further purification. The acid chloride was dissolved in THF (20 mL, dry) and added dropwise at room temperature to the amine which was dissolved in THF (20 mL, dry) containing NMM (200 µL). Stirring was continued overnight at room temperature and then the solvent was removed under reduced pressure at 50° C. The residue was dissolved in DCM (50 mL) and extracted with K$_2$CO$_3$ (270 mg, in water 20 mL). The organic layer was dried over MgSO$_4$, filtered and the solvent removed under reduced pressure. The crude product was purified by column chromatography using methanol/ethyl acetate/TEA (100:100:1) to give the product as yellow glassy material (R$_f$=0.20), 223 mg, 82% yield. M.p. 110-115° C. [Transparent].

NMR[CDCl$_3$]: 0.93(6H, d, J=1.6 Hz), 0.95(6H, d, J=5.6 Hz), 0.98(6H, d, J=3.7 Hz), 1.57-1.78(5H, m), 2.47(6H, s), 2.70(2H, m), 3.49(2H, m), 4.31-4.49(6H, m), 6.57(1H, s), 7.28(1H, s), 7.33(1H, s), 7.41(1H, s), 7.44(1H, s), 7.61(1H, s), 7.64(1H, d, J=1.8 Hz), 7.75(1H, s), 8.22(1H, s). IR $\nu_{max}$ [KBr]: 2953, 1646, 1583, 1534, 1505, 1464, 1422, 1311 cm$^{-1}$. HRPABMS: Found: 667.42932 Calculated for C$_{35}$H$_{55}$O$_5$N$_8$ 667.42954.

(vi) N-[5-({[5-({[3-(Dimethylamino)propyl]amino}carbonyl)-1-isopentyl-1H-pyrrol-3-yl]amino}carbonyl)-1-isopentyl-1H-pyrrol-3-yl]-4-(formylamino)-1-isopentyl-1H-pyrrole-2-carboxamide N-[5-({[5-({[3-(Dimethylamino)propyl]amino}carbonyl)-1-isopentyl-1H-pyrrol-3-yl]amino}carbonyl)-1-isopentyl-1H-pyrrol-3-yl]-1-isopentyl-4-nitro-1H-pyrrole-2-carboxamide (119 mg, 0.178 mmol; see step (v) above) was dissolved in ethanol (20 mL) and Pd/C-10% (104 mg) was added at 0° C. under N$_2$ with stirring. The reaction mixture was hydrogenated at room temperature and atmospheric pressure for 3 h. The catalyst was removed over Kieselguhr, then ethyl formate (15 mL) was added to the ethanolic solution of the amine. The reaction mixture was heated under reflux for 4 days. The solvent was removed under reduced pressure and the crude product was chromatographed over silica gel using ethyl acetate/methanol/TEA (100:100:1). The product was obtained as light brown solid with no distinct m.p., $R_f$=0.15, (84 mg, 71%). Some of this material was purified further by HPLC.

NMR[DMSO-$d_6$]: 0.87-0.90(18H, m), 1.47-1.53(9H, m), 1.75(2H, m), 2.78(6H, d, J=4.8 Hz), 3.06(2H, m), 3.25(2H, m), 4.31(6H, qt, J=7.2 Hz), 6.88(1H, d, J=1.8 Hz), 6.92(1H, d, J=1.8 Hz), 7.02(1H, d, J=1.8 Hz), 7.19(1H, d, J=1.8 Hz), 7.23(2H, s&d), 8.13(2H, s&t), 9.21(1H, s, broad, TFA), 9.88 (1H, s), 9.89(1H, s), 10.05(1H, s). IR $v_{max}$ [KBr]: 2953, 1650, 1580, 1525, 1461, 1402, 1260, 1221 cm$^{-1}$. HRFABMS: Found: 665.44877 Calculated for $C_{36}H_{57}O_4N_8$ 665.45028.

Example 6

N-[5-({[5-({[3-(Dimethylamino)propyl] amino}carbonyl)-1-isopropyl-1H-pyrrol-3-yl] amino}carbonyl)-1-methyl-1H-pyrrol-3-yl]-4-(formylamino)-1-isopropyl-1H-pyrrole-2-carboxamide (i) N-[3-(Dimethylamino)propyl]-1-isopropyl-4-nitro-1H-pyrrole-2-carboxamide 1-Isopropyl-4-nitro-1H-pyrrole-2-carboxylic acid (312 mg, 1.574 mmol; see Example 1, step (iii) above) was dissolved in thionyl chloride (5 mL) and heated until reflux for 4 h. The excess thionyl chloride was removed under reduced pressure at 50° C. to give the acid chloride as white solid material, which was used without further purification. 3-(Dimethylamino)propyl-amine (250 μL) was dissolved in THF (20 mL, dry) to which was added NMM (250 μL, dry) at room temperature with stirring. The acid chloride was dissolved in THF (5 mL, dry) and added dropwise to the amine solution at room temperature with stirring. The stirring was continued at room temperature overnight and then the solvent was removed under reduced pressure at 50° C. The crude product was extracted with $K_2CO_3$ (25 mL, 10%) and DCM (2×50 mL). The organic layer was collected, dried over $Na_2SO_4$, filtered and the solvent removed under reduced pressure. The crude product obtained as pale yellow oil was purified over silica gel using 49.5/49.5/1% methanol/ethyl acetate/TEA to give the pure product as pale yellow oil, $R_F$=0.25, (400 mg, 90% yield).

NMR[CDCl$_3$]: 8.59(1H, broad); 7.74(1H, d); 6.92(1H, d); 5.65-5.59(1H, qt); 3.51-3.46(2H, q); 2.51(2H, t); 2.32(6H, s); 1.77-1.71(2H, qt); 1.48(6H, d). IR $v_{max}$ [NaCl]: 3330, 3136, 2979, 1650, 1535, 1430, 1341, 1279 cm$^{-1}$. HREIMS: Found: 282.16908 calculated for $C_{13}H_{22}N_4O_3$ 282.16919.

(ii) N-[5-({[3-(Dimethylamino)propylamino}carbonyl)-1-isopropyl-1H-pyrrol-3-yl]-1-methyl-4-nitro-1H-pyrrole-2-carboxamide N-[3-(Dimethylamino)propyl]-1-isopropyl-4-nitro-1H-pyrrole-2-carboxamide (120 mg, 0.425 mmol; see step (i) above) was dissolved in methanol (25 mL) to which Pd/C-10% (52 mg) was added at 0° C. under nitrogen. The reaction mixture was hydrogenated at room temperature and atmospheric pressure. The catalyst was removed over Kieselguhr and the solvent was then removed under reduced pressure at 40° C. This gave the amine (as pale yellow oil), which was then dissolved in DCM (25 mL, dry). 1-Methyl-4-nitro-1H-pyrrole-2-carboxylic acid (90 mg, 0.529 mmol; see *Tetrahedron* 56, 5225-5239 (2000)) was suspended in thionyl chloride (4 mL) then heated until reflux for 4 h. The excess thionyl chloride was removed under reduced pressure at 40° C. The acid chloride so obtained was dissolved in DCM (25 mL, dry) then added dropwise with stirring at room temperature to the amine solution. The reaction mixture was left stirring at room temperature overnight. $K_2CO_3$ solution (232 mg, in water 10 mL) was added and the mixture was extracted with DCM (3×25 mL). The organic layers were combined, dried over MgSO$_4$, filtered and the solvent removed under reduced pressure. The crude product was purified by flash chromatography using silica gel, methanol/ethyl acetate/TEA [1/3 containing 1% TEA]. The product was obtained as microcrystalline yellow solid (165 mg, 96%), m.p. 161-163° C.

NMR(CDCl$_3$): 1.43-1.44(6H, d, J=6.4 Hz, 2xMe); 1.72-1.79(2H, quintet, J=6.2 Hz, CH$_2$); 2.33(6H, s, NMe$_2$); 2.47-2.50(2H, t, J=6.2 Hz, CH$_2$); 3.45-3.49(2H, q, J=5.7 Hz, CH$_2$); 4.04(3H, s, NMe); 5.57-5.62(1H, m); 6.46(1H, d, 1.8J=Hz); 7.22(1H, d, J=1.7 Hz); 7.39(1H, d, J=1.7 Hz); 7.60(1H, d, J=1.7 Hz); 7.73(1H, t, J=5.6 Hz, CONH, exch.); 7.77(1H, s, CONH, exch.). IR $v_{max}$ [KBr]: 3281, 3110, 2967, 1640, 1557, 1532, 1503, 1468, 1409, 1310 cm$^{-1}$. HRFABMS: Found: 405.22501 Calculated for $C_{19}H_{29}N_6O_4$ 405.22503.

(iii) N-[5-({[5-({[3-(Dimethylamino)propyl] amino}carbonyl)-1-isopropyl-1H-pyrrol-3-yl] amino}carbonyl)-1-methyl-1H-pyrrol-3-yl]-1-isopropyl-4-nitro-1H-pyrrole-2-carboxamide N-[5-({[3-(Dimethylamino)propyl]amino}carbonyl)-1-isopropyl-1H-pyrrol-3-yl]-1-methyl-4-nitro-1H-pyrrole-2-carboxamide (160 mg, 0.395 mmol; see step (ii) above) was suspended in methanol (25 mL) to which was added Pd/C-10% (112 mg) at 0° C. under nitrogen with stirring. The reaction mixture was hydrogenated at room temperature and atmospheric pressure for 4 h. The catalyst was removed over Kieselguhr and the solvent removed under reduced pressure at 40° C. to give the amine. 1-Isopropyl-4-nitro-1H-pyrrole-2-carboxylic acid (94 mg, 0.552 mmol; see Example 1, step (iii) above) was suspended in thionyl chloride (4 mL) and heated until reflux for 2 h. Excess thionyl chloride was removed under reduced pressure at 40° C., and the acid chloride so formed was used without further purification. The amine was dissolved in DCM (25 mL, dry) to which TEA (40 μL, dry) was added at room temperature with stirring. The acid chloride was dissolved in DCM (15 mL, dry) after which it was added to the amine solution dropwise with stirring at room temperature. The stirring was continued overnight. Na$_2$CO$_3$ solution (280 mg, in water 5 mL) was added to the reaction mixture. The organic layers obtained from the extraction were combined and dried over MgSO$_4$, filtered and the solvent removed under reduced pressure. The crude product was purified using flash chromatography. Silica gel and methanol/ethyl acetate/TEA [1/3 containing 1% TEA, $R_f$=0.1] were used to give the product as yellow solid (152 mg, 69%), m.p. 145-148° C.

NMR(DMSO-$d_6$): 1.32-1.34(6H, d, J=6.4 Hz, 2xMe); 1.45-1.46(6H, d, J=6.4 Hz, 2xMe); 1.69-1.73(2H, quintet, J=6.2 Hz, CH$_2$); 2.38(6H, s, NMe$_2$); 2.47-2.50(2H, t, J=6.2 Hz, CH$_2$); 3.19-3.24(2H, m, CH$_2$); 3.86(3H, s, NMe); 5.42-5.50(1H, m); 6.80(1H, s); 7.05(1H, d, J=1.6 Hz); 7.26(1H, d, J=1.6 Hz); 7.36(1H, d, J=1.6 Hz); 7.50(1H, d, J=1.6 Hz); 8.08-8.11(1H, t, J=5.6 Hz, CONH, exch.); 8.33(1H, d, J=1.6 Hz); 9.92(1H, s, CONH, exch.); 10.33(1H, s, CONH, exch.). IR $v_{max}$ [KBr]: 2943, 2860, 1638, 1593, 1524, 1456, 1403, 1316, 1251, 1187, 1170 cm$^{-1}$. HRFABMS: Found: 555.30593 Calculated for $C_{27}H_{39}N_8O_5$ 555.30434.

(iv) N-[5-({[5-({[3-(Dimethylamino)propyl] amino}carbonyl)-1-isopropyl-1H-pyrrol-3-yl] amino}carbonyl)-1-methyl-1H-pyrrol-3-yl]-4-(formylamino)-1-isopropyl-1H-pyrrole-2-carboxamide N-[5-({[5-({[3-(Dimethylamino)propyl] amino}carbonyl)-1-isopropyl-1H-pyrrol-3-yl] amino}carbonyl)-1-methyl-1H-pyrrol-3-yl]-1-isopropyl-4-nitro-1H-pyrrole-2-carboxamide (150 mg, 0.291 mmol; see step (iii) above) was dissolved in ethanol (15 mL). The solution was cooled to 0° C. under $N_2$ then Pd/C-10% (120 mg) was added. The reaction mixture was hydrogenated at room temperature and atmospheric pressure for 4 h. The catalyst was removed over Kieselguhr and then ethyl formate (20 mL) was added to the ethanolic solution. The reaction mixture was heated under reflux overnight and then the solvent was removed under reduced pressure at 40° C. The product was purified by HPLC to give the product as white solid material (71 mg, 40% yield) with no distinct melting point.

NMR[DMSO-$d_6$]: 10.0564(1H, s); 9.96(1H, s); 9.90(1H, s); 9.24(1H, s, broad, TFA); 8.16-8.14(2H, m); 7.34(2H, s); 7.22(1H, s); 7.06(1H, s); 6.89(1H, s); 6.68(1H, s); 5.49-5.42 (1H, m); 3.84(3H, s); 3.25(2H, m); 3.06(2H, m); 2.79(6H, d, J=4.76 Hz); 1.84(2H, m); 1.36-1.33(12H, m). IR $\nu_{max}$ [KBr]: 3425, 3285, 2972, 1676, 1639, 1579, 1533, 1465, 1439, 1404, 1257, 1200, 1180, cm$^{-1}$. HRFABMS: Found 554.33484 calculated for $C_{28}H_{42}N_8O_4$ 554.33290

Example 7

N-[5-({[3-(Dimethylamino)propyl]amino}carbonyl)-1-methyl-1H-pyrrol-3-yl]-2-({[4-(formylamino)-1-methyl-1H-pyrrol-2-yl]carbonyl}amino)-5-isopropyl-1,3-thiazole-4-carboxamide (i) N-[5-({[3-(Dimethylamino)propyl]amino}carbonyl)-1-methyl-1H-pyrrol-3-yl]-5-isopropyl-2-{[(1-methyl-4-nitro-1H-pyrrol-2-yl)carbonyl]amino}-1,3-thiazole-4-carboxamide N-[3-(Dimethylamino)propyl]-1-methyl-4-nitro-1H-pyrrole-2-carboxamide (270 mg, 1.062 mmol; see *Tetrahedron* 56, 5225-5239 (2000)) was dissolved in methanol (25 mL), to which Pd/C-10% (236 mg) was added at 0° C. under $N_2$ with stirring. The reaction mixture was hydrogenated at room temperature and atmospheric pressure for 4 h after which the catalyst was removed over Kieselguhr and the solvent was then removed under reduced pressure to give the amine. 5-Isopropyl-2-{[(1-methyl-4-nitro-1H-pyrrol-2-yl)carbonyl]amino}-1,3-thiazole-4-carboxylic acid (359 mg, 1.062 mmol; see Example 3, step (iii) above was dissolved in DMF (4 mL, dry) to which NMM (0.5 mL, dry) was added followed by HBTU (721 mg, 1.901 mmol). The amine was dissolved in DMF (2 mL, dry) and then added to the reaction mixture at room temperature with stirring. The stirring was continued at room temperature overnight. NMM was removed under reduced pressure. The reaction mixture was diluted with ethyl acetate then NaHCO$_3$ saturated was added with stirring. The organic layer was separated, dried over MgSO$_4$ and the solvent was removed under reduced pressure. The crude product obtained was chromatographed over silica gel using 1:1:0.2 methanol/ethyl acetate/TEA. The product was obtained as yellow glassy material (415 mg, 72% yield) with no distinct melting point.

NMR[DMSO-$d_6$]: 9.60(1H, s); 8.23(1H, s); 8.09-8.036 (1H, t); 7.83(1H, s); 7.25(1H, d); 6.91(1H, d); 4.22-4.16(1H, qt); 4.00(3H, s); 3.82(3H, s); 3.25-3.18(2H, q); 2.38-2.34(2H, t); 2.23(6H, s); 1.68-1.61(2H, qt); 1.30-1.28(6H, d). IR $\nu_{max}$ [KBr]: 1644, 1551, 1500, 1465, 1402, 1309, 1283, 1194, 1100 cm$^{-1}$. HRFABMS: Found: 545.22962 calculated for $C_{24}H_{33}N_8O_5S$ 545.22946.

(ii) N-[5-({[3-(Dimethylamino)propyl]amino}carbonyl)-1-methyl-1H-pyrrol-3-yl]-2-({[4-(formylamino)-1-methyl-1H-pyrrol-2-yl]carbonyl}-amino)-5-isopropyl-1,3-thiazole-4-carboxamide N-[5-({[3-(Dimethylamino)propyl]amino}carbonyl)-1-methyl-1H-pyrrol-3-yl]-5-isopropyl-2-{[(1-methyl-4-nitro-1H-pyrrol-2-yl)carbonyl]amino}-1,3-thiazole-4-carboxamide (137 mg, 0.252 mmol; see step (i) above) was dissolved in ethanol (15 mL), to which Pd/C-10% (121 mg) was added under $N_2$ at 0° C. The reaction mixture was hydrogenated at room temperature and atmospheric pressure for 2.5 h. The catalyst was removed over Kieselguhr and then ethyl formate (25 mL) was added to the ethanolic solution. The reaction mixture was heated under reflux overnight, following which the solvent was removed under reduced pressure and the product was then purified by HPLC. The product was obtained after freeze-drying as white solid material (41 mg, 25% yield) [TFA salt] with no distinct melting point.

NMR[DMSO-$d_6$]: 12.0971(1H, s); 10.1404(1H, s); 9.5957 (1H, s); 9.2310(1H, broad, TFA); 8.3533-8.3249(1H, d and 1H, t); 7.3982(1H, s); 7.2894(1H, d); 7.2046(1H, d); 7.0146 (1H, d); 4.1717-4.1200(1H, m); 3.8841(3H, s); 3.8274(3H, s); 3.2577(2H, m); 3.0646(2H, m); 2.7987(6H, d, NMe$_2$); 1.8612-1.8231(2H, m); 1.3135(6H, d). IR $\nu_{max}$ [KBr]: 3428, 1662, 1545, 1467, 1401, 1284, 1201, 1134 cm$^{-1}$. HRFABMS: Found: 543.24988 calculated for $C_{25}H_{35}N_8O_4S$ 543.25020.

Example 8

4-({[4-(Formylamino)-1-methyl-1H-pyrrol-2-yl]carbonyl}amino)-1-iso-propyl-N-[1-methyl-5-({[3-(4-morpholinyl)propyl]amino}carbonyl)-1H-pyrrol-3-yl]-1H-pyrrole-2-carboxamide (i) 1-Isopropyl-N-[1-methyl-5-({[3-(4-morpholinyl)propyl]amino}-carbonyl)-1H-pyrrol-3-yl]-4-nitro-1H-pyrrole-2-carboxamide 1-Methyl-N-[3-(4-morpholinyl)propyl]-4-nitro-1H-pyrrole-2-carboxamide (214 mg, 0.805 mmol; see *Tetrahedron* 56, 5225-5239 (2000)) was dissolved in methanol (25 mL). The solution was cooled to 0° C. under $N_2$ then Pd/C-10% (192 mg) was added. The reaction mixture was hydrogenated at room temperature and atmospheric pressure for 3 h. The catalyst was removed over Kieselguhr and the solvent was removed under reduced pressure at 50° C. The amine so formed was dissolved in DMF (2 mL, dry), to which 1-isopropyl-4-nitro-1H-pyrrole-2-carboxylic acid (160 mg, 0.805 mmol; see Example 1, step (iii) above) was added followed HBTU (610 mg, 1.608 mmol) and NMM (100 μL, dry). Additional amount of DMF (2 mL, dry) was added with stirring at room temperature and was continued for 72 h. The reaction mixture was diluted with ethyl acetate and NaHCO$_3$ solution with stirring. The organic layer was separated, dried MgSO$_4$, filtered and the solvent removed under reduced pressure. The crude product was chromatographed over flash silica gel using 1/3 methanol/ethyl acetate. Fractions containing the product [R$_F$=0.30] were collected and the solvents were removed under reduced pressure at 50° C. The product was obtained as glassy yellow material [hygroscopic] (260 mg, 73% yield) with no distinct melting point.

NMR[DMSO-$d_6$]: 10.28(1H, s); 8.33(1H, d); 8.08-8.05 (1H, t); 7.48(1H, d); 7.20(1H, d); 6.85(1H, d); 5.89-5.42(1H, qt); 3.80(3H, s); 3.58-3.56(4H, t); 3.22-3.17(2H, q); 2.32-2.28(6H, m); 1.67-1.62(2H, qt); 1.45-1.43(6H, d). IR $\nu_{max}$ [KBr]: 1661, 1582, 1540, 1441, 1389, 2326, 1284, 1242, 1116, 850, 755 cm$^{-1}$. HREIMS: found 446.22568 calculated for $C_{21}H_{30}N_6O_5$ 446.22777.

(ii) 1-Isopropyl-N-[1-methyl-5-({[3-(4-morpholinyl)propyl]amino}-carbonyl)-1H-pyrrol-3-yl]-4-{[(1-methyl-4-nitro-1H-pyrrol-2-yl)carbonyl]-amino}-1H-pyrrole-2-carboxamide 1-Isopropyl-N-[1-methyl-5-({[3-(4-morpholinyl)propyl]amino}carbonyl)-1H-pyrrol-3-yl]-4-nitro-1H-pyrrole-2-carboxamide (250 mg, 0.560 mmol; see step (i) above) was dissolved at 0° C. under $N_2$. Pd/C-10% (220 mg) was added and the reaction mixture was hydrogenated for 3.5 h. The catalyst was removed over Kieselguhr and the solvent was removed under reduced pressure. The amine so formed was dissolved in DMF (2 mL, dry), to which was NMM (100 μL, dry) was added followed by HBTU (425 mg, 1.069 mmol) and 1-methyl-4-nitro-1H-pyrrole-2-carboxylic acid (95 mg, 0.560 mmol; see *Tetrahedron* 56, 5225-5239 (2000)) with stirring at room temperature. The stirring was continued overnight. The reaction mixture was diluted with ethyl acetate and a saturated solution of sodium hydrogen carbonate. The organic layer was separated, dried over $MgSO_4$ and filtered. The solvent was removed under reduced pressure and the crude product was chromatographed using flash silica gel and 1:3:0.1 methanol/ethyl acetate/TEA. Fractions containing the pure material were collected [$R_F$=0.3] solvents were removed under reduced pressure at 40° C. to give semi-solid glassy yellow material (170 mg, 53%) with no distinct melting point.

NMR[DMSO-$d_6$]: 10.31(1H, s); 9.98(1H, s); 8.20(1H, s); 8.04-8.01(1H, t); 7.59(1H, s); 7.44(1H, s); 7.18(1H, s); 6.92 (1H, s); 6.86(1H, s); 5.49-5.42(1H, qt); 3.97(3H, s); 3.80(3H, s); 3.58-3.57(4H, t); 3.22-3.17(2H, q); 2.33-2.29(2H, d); 1.68-1.61(2H, qt); 1.38-1.36(6H, d); 1.05-1.01(2H, m). IR $v_{max}$[KBr]:3425, 2927, 1662, 1653, 1582, 1543, 1502, 1410, 1307, 1251, 1203, 1115, 848 cm$^{-1}$. HRFABMS: found 569.28147 calculated for $C_{27}H_{37}N_8O_6$ 569.28361.

(iii) 4-({[4-(Formylamino)-1-methyl-1H-pyrrol-2-yl]carbonyl}amino)-1-isopropyl-N-[1-methyl-5-({[3-(4-morpholinyl)propyl]amino}carbonyl)-1H-pyrrol-3-yl]-1H-pyrrole-2-carboxamide 1-Isopropyl-N-[1-methyl-5-({[3-(4-morpholinyl)propyl]amino}carbonyl)-1H-pyrrol-3-yl]-4-{[(1-methyl-4-nitro-1H-pyrrol-2-yl)carbonyl]amino}-1H-pyrrole-2-carboxamide (160 mg, 0.282 mmol; see step (ii) above) was dissolved in ethanol (25 mL) to which Pd/C-10% (150 mg) was added at 0° C. under nitrogen with stirring. The reaction mixture was hydrogenated for 2 h at room temperature and atmospheric pressure. The catalyst was removed over Kieselguhr. Ethyl formate (25 mL) was added to the ethanolic solution, then the reaction mixture was heated under reflux overnight. Ethanol and excess ethyl formate were removed under reduced pressure and the crude product was purified by HPLC to give the required material as white solid (40.1 mg, 21% yield) with no distinct melting point.

NMR[DMSO-$d_6$]: 10.05(1H, s); 9.93(1H, s); 9.92(1H, s); 9.58(1H, broad, TFA); 8.17(1H, t); 8.13(1H, s); 7.39(1H, s); 7.19(1H, s); 7.17(1H, s); 6.97(1H, s); 6.95(1H, s); 6.92(1H, s); 3.84(3H, s); 3.81(3H, s); 3.56-3.60(4H, t); 3.49-3.43(4H, t); 3.26-3.24(2H, q); 3.12-3.06(4H, m); 1.87(2H, qt); 1.37-1.36(6H, d). IR $v_{max}$ [KBr]: 3423, 1672, 1644, 1581, 1536, 1462, 1440, 1407, 1254, 1200, 1134 cm$^{-1}$. HRFABMS: found: 567.30312 calculated for $C_{28}H_{39}N_8O_5$ 567.30434.

Example 9

4-(Formylamino)-N-[1-isopropyl-5-({[1-methyl-5-({[3-(1-pyrrolidinyl)-propyl]amino}carbonyl)-1H-pyrrol-3-yl]amino}carbonyl)-1H-pyrrol-3-yl]-1-methyl-1H-pyrrole-2-carboxamide (i) 1-Methyl-4-nitro-N-[3-(1-pyrrolidinyl)propyl]-H-pyrrole-2-carboxamide 3-(1-Pyrrolidino)propylamine (236 mg, 1.842 mmol (Lancaster Synthesis Ltd.)) was dissolved in THF (25 mL, dry) to which a solution of 2,2,2-trichloro-1-(1-methyl-4-nitro-1H-pyrrol-2-yl)ethanone (508 mg, 1.842 mmol; see *Tetrahedron* 56, 5225-5239 (2000)) was added in THF (2 mL, dry) at room temperature with stirring. The reaction mixture was left stirring at room temperature overnight. The solvent was removed under reduced pressure and the crude product was purified by column chromatography using 49.5:49.5:1 ethyl acetate/methanol/TEA. The product was obtained as glassy yellow solid, $R_f$=0.1 (503 mg, 98% yield), m.p. 113-115° C.

$^1$H-NMR(DMSO-$d_6$) δ 1.70-1.79(6H, m), 2.48-2.51(6H, m), 3.28-3.51(2H, q, J=6.85 Hz), 3.89(3H, s), 7.45(1H, d, J=1.6 Hz), 8.18(1H, d, J=1.6 Hz), 8.51(1H, t, J=5.37 Hz). IR $v_{max}$[KBr]: 3131, 2966, 2794, 1654, 1545, 1525, 1492, 1305 cm$^{-1}$. HRFABMS: Found: 281.16249 Calculated for $C_{13}H_{21}N_4O_3$ 281.16137.

(ii) 1-Isopropyl-N-[1-methyl-5-({[3-(1-pyrrolidinyl)propyl]amino}-carbonyl)-1H-pyrrol-3-yl]-4-nitro-1H-pyrrole-2-carboxamide 1-Methyl-4-nitro-N-[3-(1-pyrrolidinyl)propyl]-1H-pyrrole-2-carboxamide (227 mg, 0.811 mmol; see step (i) above) was dissolved in methanol (25 mL) to which Pd/C-10% (160 mg) was added at 0° C. under nitrogen with stirring. The reaction mixture was hydrogenated for 2 h at room temperature and atmospheric pressure. The catalyst was removed over Kieselguhr and the solvent was removed under reduced pressure at 40° C. to give the amine. 1-Isopropyl-4-nitro-1H-pyrrole-2-carboxylic acid (161 mg, 0.811 mmol; see Example 1, step (iii)) was dissolved in DMF (1 mL, dry) to which HBTU (615 mg, 1.622 mmol) and NMM (100 μL, dry) were added. The amine was dissolved in DMF (2 mL, dry) and added to the reaction mixture at room temperature with stirring. The stirring was continued at room temperature overnight. The reaction mixture was diluted with ethyl acetate and a saturated solution of sodium hydrogen carbonate. The organic layer was separated, dried over magnesium sulphate, filtered and the solvent removed under reduced. The product was purified by column chromatography using 1/2/0.1 methanol/ethyl acetate/TEA. The product was obtained as yellow material (300 mg, 86% yield) with no distinct melting point. Some of this material was further purified by HPLC.

NMR[DMSO-$d_6$]: 10.31(1H, s); 9.48(1H, broad, TFA); 8.34(1H, d); 8.21-8.18(1H, t); 7.48(1H, d); 7.28(1H, d); 6.92 (1H, d); 5.48-5.42(1H, qt); 3.82(3H, s); 3.56-3.55(2H, m); 3.27-3.23(2H, q); 3.17-3.12(2H, m); 2.99-2.97(2H, m); 2.01 (2H, m); 1.86-1.83(4H, m); 1.45-1.44(6H, d). IR $v_{max}$[KBr]: 3433, 1672, 1650, 1535, 1462, 1426, 1371, 1321, 1283, 1237, 1200, 1178, 1131 cm$^{-1}$. HRFABMS: found: 430.23179 calculated for $C_{21}H_{30}N_6O_4$ 430.23285.

(iii) N-[1-Isopropyl-5-({[1-methyl-5-({[3-(1-pyrrolidinyl)propyl]amino}-carbonyl)-1H-pyrrol-3-yl]amino}carbonyl)-1H-pyrrol-3-yl]-1-methyl-4-nitro-1H-pyrrole-2-carboxamide 1-Isopropyl-N-[1-methyl-5-({[3-(1-pyrrolidinyl)propyl]amino}carbonyl)-1H-pyrrol-3-yl]-4-nitro-1H-pyrrole-2-carboxamide (300 mg, 0.697 mmol; see step (ii) above) was dissolved in methanol (25 mL) to which Pd/C-10% (235 mg) was added at 0° C. under nitrogen with stirring. The reaction mixture was hydrogenated for 3 h at room temperature and atmospheric pressure. The catalyst was removed over Kieselguhr and the solvent was removed under reduced pressure at 40° C. to give the amine. 1-Methyl-4-nitro-1H-pyrrole-2-carboxylic acid (119 mg, 0.699 mmol; see *Tetrahedron* 56, 5225-5239 (2000)) was dissolved in DMF (2 mL, dry) to which HBTU (529 mg, 1.394 mmol) and NMM (100 μL, dry) were added. The amine was dissolved in DMF (2 mL, dry) and added to the reaction mixture at room temperature with stirring. The stirring was continued at room temperature overnight. The reaction mixture was diluted with ethyl acetate and a saturated solution of sodium hydrogen carbonate. The organic layer was separated, dried over magnesium sulphate, filtered and the solvent removed under reduced pressure. The product was purified by column chromatography using 1/2/0.1 methanol/ethyl acetate/TEA. The product was obtained as yellow material (239 mg, 62% yield) with no distinct melting point. Some of this material was further purified by HPLC.

NMR[DMSO-$d_6$]: 10.28(1H, s); 9.98(1H, s); 9.46(1H, broad, TFA); 8.19(1H, s); 8.14(1H, t); 7.58(1H, s); 7.43(1H, s); 7.18(1H, s); 6.94(2H, s); 5.46-5.43(1H, m); 3.97(3H, s); 3.82(3H, s); 3.55(2H, m); 3.27(2H, m); 3.14(2H, m); 3.00 (2H, m); 2.02(2H, m); 1.86(4H, m); 1.38-1.37(6H, d). IR $\nu_{max}$ [KBr]: 3419, 3136, 1673, 1645, 1586, 1531, 1463, 1409, 1311, 1247, 1199, 1130 cm$^{-1}$. HRFABMS: found: 553.29109 calculated for $C_{27}H_{37}N_8O_5$ 553.28869.

(iv) 4-(Formylamino)-N-[1-isopropyl-5-({[1-methyl-5-({[3-(1-pyrrolidinyl)-propyl]amino}carbonyl)-1H-pyrrol-3-yl]amino}carbonyl)-1H-pyrrol-3-yl]-1-methyl-1H-pyrrole-2-carboxamide N-[1-Isopropyl-5-({[1-methyl-5-({[3-(1-pyrrolidinyl)propyl]amino}-carbonyl)-1H-pyrrol-3-yl]amino}carbonyl)-1H-pyrrol-3-yl]-1-methyl-4-nitro-1H-pyrrole-2-carboxamide (224 mg, 0.406 mmol; see step (iii) above) was dissolved in ethanol (25 mL) to which Pd/C-10% (224 mg) was added at 0° C. under nitrogen with stirring. The reaction mixture was hydrogenated for 2.5 h at room temperature and atmospheric pressure. The catalyst was removed over Kieselguhr. Ethyl formate (15 mL) was added to the ethanolic solution, then the reaction mixture was heated under reflux overnight. Ethanol and excess ethyl formate were removed under reduced pressure and the crude product was purified by HPLC to give the required material as white solid (42.7 mg, 16% yield) with no distinct melting point.

NMR[DMSO-$d_6$]: 10.07(1H, s); 9.94(1H, s); 9.92(1H, s); 9.42(1H, broad, TFA); 8.17-8.13(1H, 2H, m); 7.39(1H, d); 7.19(1H, d); 7.17(1H, d); 6.97(1H, d); 6.95(1H, d); 6.92(1H, d); 3.84(3H, s); 3.61(3H, s); 3.55(2H, m); 3.26-3.24(2H, m); 3.17-3.12(2H, m); 3.00(2H, m); 2.01(2H, m); 1.86(4H, m); 1.37-1.36(6H, d). IR $\nu_{max}$ [KBr]: 3429, 1675, 1645, 1582, 1534, 1462, 1440, 1407, 1252, 1200, 1132 cm$^{-1}$. HRFABMS: found: 551.31199 calculated for $C_{28}H_{39}N_8O_4$ 551.30943.

Example 10

N-[5-({[5-({[3-(Dimethylamino)propyl]amino}carbonyl)-1-methyl-1H-pyrrol-3-yl]amino}carbonyl)-1-isopentyl-1H-pyrrol-3-yl]-4-(formylamino)-1-methyl-1H-pyrrole-2-carboxamide (i) N-[5-({[3-(Dimethylamino)propyl]amino}carbonyl)-1-methyl-1H-pyrrol-3-yl]-1-isopentyl-4-nitro-1H-pyrrole-2-carboxamide N-[3-(Dimethylamino)propyl]-1-methyl-4-nitro-1H-pyrrole-2-carboxamide (253 mg, 0.995 mmol; see *Tetrahedron* 56, 5225-5239 (2000)) was dissolved in methanol (25 mL) to which Pd/C-10% (162 mg) was added at 0° C. under nitrogen. The reaction mixture was hydrogenated for 4 h. The catalyst was removed over Kieselguhr and the solvent was removed under reduced pressure at 50° C. to give the amine. 1-Isopentyl-4-nitro-1H-pyrrole-2-carboxylic acid (228 mg, 1.005 mmol; prepared according to the procedure described in *Soviet Journal of Bioorganic Chemistry* (English Translation) 4, 780-790 (1978)) was dissolved in thionyl chloride (4 mL) and the reaction mixture was heated under reflux for 4 h. Excess thionyl chloride was removed under reduced pressure and the acid chloride so formed was dissolved in DCM (10 mL, dry). The amine was dissolved in DCM (10 mL, dry) to which NMM (200 µL, dry) was added at room temperature with stirring. The acid chloride solution was added dropwise to the amine solution at room temperature with stirring. The stirring was continued overnight at room temperature. The reaction mixture was diluted with DCM (25 mL) and saturated solution of sodium hydrogen carbonate (25 mL). After the extraction, the organic layer was collected, dried over magnesium sulphate, filtered and the solvent removed under reduced pressure. The product was purified by column chromatography using 1/3/0.030 methanol/ethyl acetate/TEA. Fractions containing the product ($R_F$=0.20) were collected and the solvents were removed under reduced pressure at 50° C. to give the product as yellow powder (347 mg, 81% yield), m.p. 148-151° C.

NMR[DMSO-$d_6$]: 10.23(1H, s); 8.23(1H, d); 8.14-8.11 (1H, t); 7.55(1H, d); 7.19(1H, d); 6.82(1H, d); 4.45-4.41(2H, t); 3.81(3H, s); 3.22-3.17(2H, q); 2.35-2.31(2H, t); 2.20(6H, s); 1.67-1.58(4H, m); 1.56-1.46(1H, m); 0.89-0.87(6H, d). IR $\nu_{max}$ [KBr]: 1665, 1642, 1599, 1528, 1499, 1425, 1312 cm$^{-1}$. HRFABMS: found 433.25630 calculated for $C_{21}H_{33}N_6O_4$ 433.25633.

(ii) N-[5-({[5-({[3-(Dimethylamino)propyl]amino}carbonyl)-1-methyl-1H-pyrrol-3-yl]amino}carbonyl)-1-isopentyl-1H-pyrrol-3-yl]-1-methyl-4-nitro-1H-pyrrole-2-carboxamide N-[5-({[3-(Dimethylamino)propyl]amino}carbonyl)-1-methyl-1H-pyrrol-3-yl]-1-isopentyl-4-nitro-1H-pyrrole-2-carboxamide (335 mg, 0.775 mmol; see step (i) above) was dissolved in methanol (25 mL) to which Pd/C-10% (213 mg) was added at 0° C. under nitrogen. The reaction mixture was hydrogenated for 5 h. The catalyst was removed over Kieselguhr and the solvent was removed under reduced pressure at 50° C. to give the amine. 1-Methyl-4-nitro-1H-pyrrole-2-carboxylic acid (210 mg, 1.234 mmol; see *Tetrahedron* 56, 5225-5239 (2000)) was dissolved in thionyl chloride (3 mL) and the reaction mixture was heated under reflux for 5 h. Excess thionyl chloride was removed under reduced pressure and the acid chloride so formed was dissolved in DCM (10 mL, dry). The amine was dissolved in DCM (10 mL, dry) to which NMM (200 µL, dry) was added at room temperature with stirring. The acid chloride solution was added dropwise to the amine solution at room temperature with stirring. The stirring was continued overnight at room temperature. The reaction mixture was diluted with DCM (25 mL) and saturated solution of sodium hydrogen carbonate (25 mL). After the extraction, the organic layer was collected, dried over magnesium sulphate, filtered and the solvent removed under reduced pressure. The product was purified by column chromatography using 1/3/0.030 methanol/ethyl acetate/TEA. Fractions containing the product ($R_F$=0.20) were collected and the solvents were removed under reduced pressure at 50° C. to give the product as yellow solid material (335 mg, 78% yield), m.p. 110-115° C.[transparent].

NMR[DMSO-$d_6$]: 10.28(1H, s); 9.92(1H, s); 8.18(1H, d); 8.10-8.07(1H, t); 7.59(1H, d); 7.32(1H, d); 7.18(1H, d); 6.98 (1H, d); 6.91(1H, d); 6.83(1H, d); 4.35-4.32(2H, t); 3.97(3H, s); 3.80(3H, s); 3.22-3.17(2H, q); 2.36-2.32(2H, t); 2.21(6H, s); 1.68-1.62(2H, q); 1.61-1.45(3H, m); 1.05-0.99(2H, m); 0.90-0.88(6H, d). IR $\nu_{max}$ [KBr]: 3401, 3289, 1643, 1582, 1533, 1594, 1463, 1400, 1309, 1253 cm$^{-1}$. HRFABMS: found 555.30169 calculated for $C_{27}H_{39}N_8O_5$ 555.30434.

(iii) N-[5-({[5-({[3-(Dimethylamino)propyl]amino}carbonyl)-1-methyl-1H-pyrrol-3-yl]amino}carbonyl)-1-isopentyl-1H-pyrrol-3-yl]-4-(formylamino)-1-methyl-1H-pyrrole-2-carboxamide N-[5-({[5-({[3-(Dimethylamino)propyl]amino}carbonyl)-1-methyl-1H-pyrrol-3-yl]

amino}carbonyl)-1-isopentyl-1H-pyrrol-3-yl]-1-methyl-4-nitro-1H-pyrrole-2-carboxamide (89 mg, 0.160 mmol; see step (ii) above) was dissolved in ethanol (25 mL) to which Pd/C-10% (95 mg) was added at 0° C. under nitrogen with stirring. The reaction mixture was hydrogenated for 2 h at room temperature and atmospheric pressure. The catalyst was removed over Kieselguhr. Ethyl formate (25 mL) was added to the ethanolic solution, then the reaction mixture was heated under reflux overnight. Ethanol and excess ethyl formate were removed under reduced pressure and the crude product was purified by HPLC to give the required material as pale yellow solid (37.4 mg, 35% yield) with no distinct melting point.

NMR[DMSO-$d_6$]: 10.04(1H, s); 9.90(1H, s); 9.88(1H, s); 9.63(1H, broad, TFA); 8.15-8.13(2H, s & t); 7.26(1H, s); 7.18(1H, s); 7.16(1H, s); 7.01(1H, s); 6.92(1H, s); 6.92(1H, s); 4.31-4.30(2H, t); 3.84(3H, s); 3.82(3H, s); 3.25-3.24(2H, m); 3.07(2H, m); 2.79(6H, d); 1.84-1.82(2H, m); 1.57-1.48 (3H, m); 0.90(6H, d). IR $\nu_{max}$ [KBr]: 3428, 3315, 1676, 1644, 1582, 1538, 1464, 1438, 1403, 1262, 1201, 1132 cm$^{-1}$. HRFABMS: found 553.32520 calculated for $C_{28}H_{41}N_8O_4$ 553.32508.

Example 11

2-(Acetylamino)-N-[5-({[5-({[3-(dimethylamino)propyl]amino}carbonyl)-1-methyl-1H-pyrrol-3-yl]amino}carbonyl)-1-methyl-1H-pyrrol-3-yl]-5-isopropyl-1,3-thiazole-4-carboxamide (i) Methyl 2-(acetylamino)-5-isopropyl-1,3-thiazole-4-carboxylate Methyl 2-amino-5-isopropyl-1,3-thiazole-4-carboxylate (500 mg, 2.497 mmol; see Example 3, step (i) above) was dissolved in DCM (10 mL, dry) to which NMM (300 µL, dry) was added at room temperature with stirring. Acetyl chloride (300 µL, 330 mg, 4.204 mmol) was added dropwise to the reaction mixture with stirring. The stirring was continued at room temperature overnight. Brine (25 mL) was added to the reaction mixture and the product was then extracted with DCM (2×50 mL). The organic layers were combined and dried over MgSO$_4$, filtered and the solvent removed under reduced pressure to give the crude product which was purified by column chromatography over silica gel using 1/1 ethyl acetate/n-hexane [$R_F$=0.22]. The product was obtained as white fine needles (432 mg, 72% yield), m.p. 170-172° C.

NMR(DMSO-$d_6$): 12.31(1H, s); 4.01-3.94(1H, quintet); 3.78(3H, s); 2.11(3H, s); 1.27(6H, d). IR $\nu_{max}$ [KBr]: 3277, 2971, 1752, 1694, 1543, 1202 cm$^{-1}$. HRFABMS: Found 243.08074 calculated for $C_{10}H_{15}N_2O_3S$ 243.08034.

(ii) 2-(Acetylamino)-5-isopropyl-1,3-thiazole-4-carboxylic acid

Methyl 2-(acetylamino)-5-isopropyl-1,3-thiazole-4-carboxylate (242 mg, 1.00 mmol; see step (i) above) was dissolved in ethanol (10 mL) to which ethanolic sodium hydroxide [0.5 M, 10 mL] was added. The reaction mixture was heated under reflux for 30 min following which it was cooled to 0° C. and then dilute HCl was added with stirring until pH 2. Water (50 mL) was added and the white precipitate was filtered off and dried under reduced pressure at 45° C. overnight. The product was obtained as micro-crystalline white solid (166 mg, 73% yield), m.p.>230° C.

NMR(DMSO-$d_6$): 12.65(1H, br); 12.23(1H, s); 4.04-3.97 (1H, quintet); 2.11(3H, s); 1.26(6H, d). IR $\nu_{max}$ [KBr]: 3076, 2971, 2868, 1699, 1671, 1568, 1543, 1301, 1221 cm$^{-1}$. HRFABMS: Found 229.06408 calculated for $C_9H_{13}N_2O_3S$ 229.06469.

(iii) 2-(Acetylamino)-N-[5-({[5-({[3-(dimethylamino)propyl]amino}-carbonyl)-1-methyl-1H-pyrrol-3-yl]amino}carbonyl)-1-methyl-1H-pyrrol-3-yl]-5-isopropyl-1,3-thiazole-4-carboxamide N-[5-({[3-Dimethylamino)propyl]amino}carbonyl)-1-methyl-1H-pyrrol-3-yl]-1-methyl-4-nitro-1H-pyrrole-2-carboxamide (105 mg, 0.279 mmol; see Tetrahedron 56, 5225-5239, (2000)) was dissolved in methanol (25 mL). The solution was cooled to 0° C. under $N_2$ then Pd/C-10% (82 mg) was added. The reaction mixture was hydrogenated at room temperature and atmospheric pressure for 3 h. The catalyst was removed over Kieselguhr and then the solvent was removed under reduced pressure at 50° C. The amine thus formed was dissolved in DMF (2 mL, dry), to which 2-(acetylamino)-5-isopropyl-1,3-thiazole-4-carboxylic acid (96 mg, 0.418 mmol; see step (ii) above) was added, followed by HBTU (211 mg, 0.556 mmol) and NMM (300 µL, dry). The reaction mixture was left stirring at room temperature overnight after which it was diluted with ethyl acetate and NaHCO$_3$ solution with stirring. The organic layer was separated, dried MgSO$_4$, filtered and the solvent removed under reduced pressure. The product was purified by HPLC to give the pure material as white solid (71.3 mg, 38% yield) with no distinct melting point.

NMR[DMSO-$d_6$]: 12.31(1H, s); 8.87(1H, s); 9.57(1H, s); 9.24(1H, broad); 8.14(1H, t); 7.26(1H, d); 7.17(1H, d); 7.12 (1H, d); 6.94(1H, d); 4.19-4.12(1H, m); 3.85(3H, s); 3.81(3H, s); 3.25(2H, m); 3.07(2H, m); 2.79(6H, d); 2.16(3H, s); 1.83 (2H, qt); 1.29(6H, d). IR $\nu_{max}$ [KBr]: 1676, 1644, 1550, 1465, 1435, 1404, 1202, 1136 cm$^{-1}$. HRFABMS: found 557.26442 calculated for $C_{26}H_{37}N_8O_4S$ 557.26585.

Example 12

2-(Acetylamino)-N-[5-({[4-({[3-(dimethylamino)propyl]amino}carbonyl)-5-isopropyl-1,3-thiazol-2-yl]amino}carbonyl)-1-methyl-1H-pyrrol-3-yl]-5-isopropyl-1,3-thiazole-4-carboxamide N-[3-(Dimethylamino)propyl]-5-isopropyl-2-{[(1-methyl-4-nitro-1H-pyrrol-2-yl)carbonyl]amino}-1,3-thiazole-4-carboxamide (100 mg, 0.236 mmol; see Example 3, step (iv) above) was dissolved in methanol (25 mL). The solution was cooled to 0° C. under $N_2$ then Pd/C-10% (82 mg) was added. The reaction mixture was hydrogenated at room temperature and atmospheric pressure for 3 h. The catalyst was removed over Kieselguhr and the solvent was then removed under reduced pressure at 50° C. The amine so formed was dissolved in DMF (2 mL, dry), to which 2-(acetylamino)-5-isopropyl-1,3-thiazole-4-carboxylic acid (64 mg, 0.356 mmol; see Example 11, step (ii) above) was added, followed by HBTU (135 mg, 0.356 mmol) and NMM (200 µL, dry). The reaction mixture was left stirring at room temperature overnight, after which it was diluted with ethyl acetate and NaHCO$_3$ solution with stirring. The organic layer was separated, dried MgSO$_4$, filtered and the solvent removed under reduced pressure. The product was purified by HPLC to give the pure material as white solid (78.8 mg, 47% yield) with no distinct melting point.

NMR[DMSO-$d_6$]: 12.11(1H, s); 12.01(1H, s); 9.64(1H, s); 9.27(1H, broad); 7.96(1H, t); 7.51(1H, d); 7.42(1H, d); 4.22-4.11(2H, m); 3.90(3H, s); 3.34(2H, m); 3.08(2H, m); 2.79 (6H, d); 2.16(3H, s); 1.91-1.85(2H, qt); 1.30-1.27(12H, 2xd).

IR $\nu_{max}$ [KBr]: 1666, 1549, 1508, 1466, 1398, 1286, 1201, 1134 cm$^{-1}$. HRFABMS: found 603.25162 calculated for $C_{27}H_{39}N_8O_4S_2$ 603.25357.

Example 13

2-(Acetylamino)-N-(5-{[(3-{[3-(dimethylamino)propyl]amino}-3-oxopropyl)amino]carbonyl}-1-methyl-1H-pyrrol-3-yl-5-isopropyl-1,3-thiazole-4-carboxamide Samples of Boc-BALa-PAM resin (100 mg of 100-200 mesh (Novabiochem)) were placed in 10 separate vials to each of which was added DCM (0.5 mL, dry). TFA (80%) in DCM (3 mL, dry) was then added to each vial. The reactions were carried out under nitrogen and the reaction mixture agitated for 15 min. Following this, the solvents were drained and the resin washed with DMF (2×2 mL, dry) and they were then agitated for 5 min and then drained. 4-[(tert-Butoxycarbonyl)amino]-1-methyl-1H-pyrrole-2-carboxylic acid (180 mg, 0.750 mmol; see J. Med. Chem. 46(17), 3492-3497 (1981)) was dissolved in DMF (15 mL, dry) and then (1.5 mL) of this solution was added to each vial. HBTU (284 mg, 0.748 mmol) was dissolved in DMF (15 mL, dry) then (1.5 mL) of this solution was added to each vial followed by diisopropylethylamine (0.5 mL, dry). The agitation was continued for 30 min after which the solvents and reagents were drained. TFA (80%) in DCM (3 mL, dry) were added to each vial. The reaction mixture was agitated for a further 15 min. The solvents were drained and the resin was then washed with DMF (2×2 mL, dry) and agitated for 5 min and then drained. 2-(Acetylamino)-5-isopropyl-1,3-thiazole-4-carboxylic acid (171 mg, 0.750 mmol; see Example 11, step (ii) above) was dissolved in DMF (15 mL, dry) then (1.5 mL) of this solution was added to each vial. HBTU (284 mg, 0.748 mmol) was dissolved in DMF (15 mL, dry) then 1.5 mL of this solution, followed by diisopropylethylamine (0.5 mL, dry), was added to each vial. Agitation was continued for 30 min after which the solvents and reagents were drained. The resin in each vial was washed successively with DMF (3 mL, dry) for min with agitation, drained and then followed by DCM (3 mL, dry), drained again and finally washed with THF (3 mL, dry) and drained again. To each vial THF (3 mL, dry) was added followed by 3-(dimethylamino)-propylamine (0.5 mL, dry). Agitation was continued overnight at 55° C., then the solvent was filtered. The combined filtrate was collected and the solvent and reagent were removed under reduced pressure to give the crude product as brown oil. This material was further purified by HPLC and the fractions containing the required material were freeze-dried. The pure product was obtained as white solid (92 mg, 20% yield) with no distinct melting point.

NMR[DMSO-d$_6$]: 12.07(1H, s); 9.51(1H, s); 9.24(1H, broad); 8.03(2H, t); 7.21(1H, d); 6.91(1H, d); 4.17-4.11(1H, m); 3.81(3H, s); 3.41-3.38(2H, m); 3.13-3.09(2H, m); 3.01(2H, m); 2.74(2H, t); 2.35(2H, t); 2.15(3H, s); 1.77-1.71(2H, qt); 1.28(6H, d). IR $\nu_{max}$ [KBr]: 1673, 1548, 1465, 1438, 1404, 1286, 1201, 1180, 1131 cm$^{-1}$. HRFABMS: Found 506.25688 calculated for $C_{23}H_{36}N_7O_4S$ 506.25495.

Example 14

N$^1$,N$^3$-Bis(2-{[5-({[4-({[3-(dimethylamino)propyl]amino}carbonyl)-5-isopropyl-1,3-thiazol-2-yl]amino}carbonyl)-1-methyl-1H-pyrrol-3-yl]amino}-2-oxoethyl)isophthalamide N-[3-(Dimethylamino)propyl]-5-isopropyl-2-{[(1-methyl-4-nitro-1H-pyrrol-2-yl)carbonyl]amino}-1,3-thiazole-4-carboxamide (100 mg, 0.236 mmol; see Example 3, step (iv) above) was dissolved in methanol (25 mL). The solution was cooled to 0° C. under N$_2$ then Pd/C-10% (86 mg) was added. The reaction mixture was hydrogenated at room temperature and atmospheric pressure for 5 h. The catalyst was removed over Kieselguhr and the solvent was then removed under reduced pressure at 50° C. The amine so formed was dissolved in DMF (2 mL, dry), to which [(3-{[(carboxymethyl)amino]carbonyl}benzoyl)amino]acetic acid (33 mg, 0.118 mmol; see J. Med. Chem. 43, 3257-3266 (2000)) was added followed by HBTU (270 mg, 0.710 mmol) and NMM (300 µL, dry). An additional amount of DMF (2 mL, dry) was added with stirring at room temperature and the stirring was continued for 72 h. The reaction mixture was diluted with ethyl acetate/methanol (40 mL/10 mL) and brine with stirring. After extraction the organic layers were collected and the solvents removed under reduced pressure. The product was purified by HPLC and the fractions containing the desired material were freeze-dried. The product was obtained as white solid material (25 mg, 16% yield) with no distinct melting point.

NMR[DMSO-d$_6$]: 12.03(2H, s); 10.08(2H, s); 9.24(2H, broad); 8.93(2H, t); 8.05(2H, d); 7.94(2H, t); 7.61(1H, t); 7.39(2H, d); 7.25(2H, d); 4.21-4.15(2H, m); 4.06(2H, d); 3.87(6H, s); 3.30(4H, m); 3.07(4H, m); 2.79(6H, d); 1.86(4H, qt); 1.28(12H, d). IR $\nu_{max}$ [KBr]: 1655, 1548, 1467, 1403, 1288, 1202, 1132 cm$^{-1}$. LRLCMS: Found 1029.3 calculated for $C_{48}H_{65}N_{14}O_8S_2$ 1029.5.

Example 15

The following compounds were prepared using analogous techniques to those described hereinbefore:

N-[5-({[5-({[3-(Dimethylamino)propyl]amino}carbonyl)-1-methyl-1H-pyrrol-3-yl]amino}carbonyl)-1-isopropyl-1H-pyrrol-3-yl]-4-(acetylamino)-1-methyl-1H-pyrrole-2-carboxamide; and N-[5-({[5-({[3-(Dimethylamino)propyl]amino}carbonyl)-1-methyl-1H-pyrrol-3-yl]amino}carbonyl)-1-isopentyl-1H-pyrrol-3-yl]-4-(acetylamino)-1-methyl-1H-pyrrole-2-carboxamide.

Example 16

N$^2$,N$^5$-Bis[5-({[4-({[3-(dimethylamino)propyl]amino}carbonyl)-5-isopropyl-1,3-thiazol-2-yl]amino}carbonyl)-1-methyl-1H-pyrrol-3-yl]-1H-indole-2,5-dicarboxamide N-[3-(Dimethylamino)propyl]-5-isopropyl-2-{[(1-methyl-4-nitro-1H-pyrrol-2-yl)carbonyl]amino}-1,3-thiazole-4-carboxamide (122 mg, 0.284 mmol; see Example 3, step (iv) above) and Pd/C-10% (110 mg) were suspended in methanol (20 mL) and hydrogenated for 2.5 h at room temperature. Filtration of catalyst over Kieselguhr under N$_2$, followed by removal of the solvent under reduced pressure gave the amine as an off-white solid, which was used without further purification. Indole-2,5-dicarboxylic acid (29 mg, 0.142 mmol; prepared according to a standard literature procedure (see H. G. Lindwall and G. J. Mantell J. Org. Chem. 18, 345-356 (1953))) was dissolved in DMF (0.5 mL, dry), to which was added a solution of HBTU (107 mg, 0.284 mmol) and NMM (0.2 mL, dry) in DMF (1 mL, dry) at room temperature with stirring. The stirring was continued for 30 min. at room temperature. This mixture was added to the amine with stirring at room temperature and stirring was continued at room temperature overnight, followed by purification by HPLC to give the desired material as bis-TFA salt (32 mg, 23% yield) with no distinct melting point.

NMR [DMSO-$d_6$]: 1.3(12H, s, isopropyl$Me_2$); 2.08(1H, m, isopropylCH); 1.85-1.92(4H, m, 2x$CH_2$); 2.80(6H, s, $NMe_2$); 2.81(6H, s, $NMe_2$); 3.07(4H, m, 2x$CH_2$); 3.23(4H, m, 2x$CH_2$); 3.93(6H, s, NMe); 7.46(2H, m); 7.54(2H, m); 7.85(1H, m); 7.99(2H, m); 8.35(1H, s); 9.37(2H, br, 2xTFA, exch); 10.32(1H, s); 10.52(1H, s); 11.95(1H, s); 12.09(1H, s); 12.15(1H, s). IR [KBr]: 3415, 2960, 2362, 1654, 1549, 1467, 1398, 1287, 1200, 1134 $cm^{-1}$. HRFABMS: found 953.42; calculated for $C_{46}H_{59}N_{13}O_6S_2$ 953.42.

Example 17

$N^2$,$N^5$-Bis[1-isopentyl-5-({[1-methyl-5-({[3-(4-morpholinyl)propyl]amino}-carbonyl)-1H-pyrrol-3-yl]amino}carbonyl)-1H-pyrrol-3-yl]-1H-indole-2,5-dicarboxamide 1-Isopentyl-N-[1-methyl-5-({[3-(4-morpholinyl)propyl]amino}carbonyl)-1H-pyrrol-3-yl]-4-nitro-1H-pyrrole-2-carboxamide (120 mg, 0.25 mmol; see Example 30, step (i) below) and Pd/C-10% (110 mg) were suspended in methanol (20 mL) and hydrogenated for 2.5 h at room temperature. Filtration of catalyst over Kieselguhr under $N_2$, followed by removal of the solvent under reduced pressure gave the amine as an off-white solid, which was used without further purification. Indole-2,5-dicarboxylic acid (26 mg, 0.125 mmol; see Example 16 above) was dissolved in DMF (0.5 mL, dry), to which was added a solution of HBTU (137 mg, 0.36 mmol) and NMM (0.2 mL, dry) in DMF (1 mL, dry) at room temperature with stirring. The stirring was continued for 30 min. at room temperature. This mixture was added to amine with stirring at room temperature and stirring was continued at room temperature overnight, followed by purification by HPLC to give the desired material as bis-TFA salt (15 mg, 12% yield) with no distinct melting point.

NMR [DMSO-$d_6$]: 11.95(1H, s); 10.47(1H, s); 10.28(1H, s); 10.02(1H, s); 9.99(1H, s); 9.66(2H, br, TFA); 8.39(1H, s); 8.24(2H, t, unresolved, 2xCONH); 7.88(1H, d, J=8.7 Hz); 7.49(1H, s); 7.43(2H, s); 7.23(2H, s); 7.14(2H, s); 7.02(2H, s); 4.43(4H, m); 4.06(4H, m); 3.89(6H, s); 3.71(4H, t, J=4.6 Hz); 3.49(4H, m); 3.31(4H, m); 3.19(8H, m); 1.94(4H, m); 1.66-1.57(6H, m); 0.98(12H, d, J=6.5 Hz). IR [KBr]: 1677, 1646, 1533, 1443, 1403, 1198, 1134 $cm^{-1}$. LRESMS: Found 1058.6; calculated for $C_{56}H_{76}N_{13}O_8$ 1058.6

Example 18

$N^2$,$N^5$-Bis[5-({[5-({[3-(dimethylamino)propyl]amino}carbonyl)-1-methyl-1H-pyrrol-3-yl]amino}carbonyl)-1-isopentyl-1H-pyrrol-3-yl]-1H-indole-2,5-dicarboxamide N-[5-({[3-(Dimethylamino)propyl]amino}carbonyl)-1-methyl-1H-pyrrol-3-yl]-1-isopentyl-4-nitro-1H-pyrrole-2-carboxamide (110 mg, 0.25 mmol; see Example 10, step (i) above) and Pd/C-10% (110 mg) were suspended in methanol (20 mL) and hydrogenated for 2.5 h at room temperature. Filtration of catalyst over Kieselguhr under $N_2$, followed by removal of the solvent under reduced pressure gave the amine as an off-white solid, which was used without further purification. Indole-2,5-dicarboxylic acid (26 mg, 0.125 mmol) was dissolved in DMF (0.5 mL, dry), to which was added a solution of HBTU (137 mg, 0.36 mmol) and NMM (0.2 mL, dry) in DMF (1 mL, dry) at room temperature with stirring. The stirring was continued for 30 min. at room temperature. This mixture was added to amine with stirring at room temperature and stirring was continued at room temperature overnight, followed by purification by HPLC to give the desired material as bis-TFA salt (36 mg, 30% yield) with no distinct melting point.

NMR [DMSO-$d_6$]: 11.95(1H, s); 10.47(1H, s); 10.28(1H, s); 10.02(1H, s); 9.99(1H, s); 9.39(2H, br, 2xTFA); 8.39(1H, s); 8.22(2H, t, unresolved, 2xCONH); 7.91(1H, d, J=8.7 Hz); 7.61(1H, d, J=8.7 Hz); 7.49(1H, s); 7.43(2H, s); 7.23(2H, s); 7.13(2H, s); 7.01(2H, s); 4.43(4H, m); 3.89(6H, s); 3.31(4H, m); 3.14(4H, m); 2.86(12H, d, J=3.8 Hz); 1.91(4H, m); 1.66-1.55(6H, m); 0.98(12H, d, J=6.5 Hz). IR [KBr]: 1677, 1647, 1583, 1533, 1443, 1404, 1199, 1135 $cm^1$. HRFABMS: Found 974.6; calculated for $C_{52}H_{72}N_{13}O_6$ 974.5

Example 19

$N^2$,$N^5$-Bis[1-isopentyl-5-({[1-methyl-5-({[3-(4-methyl-1-piperazinyl)-propyl]amino}carbonyl)-1H-pyrrol-3-yl]amino}carbonyl)-1H-pyrrol-3-yl]-1H-indole-2,5-dicarboxamide 1-Isopentyl-N-[1-methyl-5-({[3-(4-methyl-1-piperazinyl)propyl]amino]-carbonyl)-1H-pyrrol-3-yl]-4-nitro-1H-pyrrole-2-carboxamide (122 mg, 0.25 mmol; see Example 29, step (i) below) and Pd/C-10% (110 mg) were suspended in methanol (20 mL) and hydrogenated for 2.5 h at room temperature. Filtration of catalyst over Kieselguhr under $N_2$, followed by removal of the solvent under reduced pressure gave the amine as an off-white solid, which was used without further purification. Indole-2,5-dicarboxylic acid (26 mg, 0.125 mmol) was dissolved in DMF (0.5 mL, dry), to which was added a solution of HBTU (137 mg, 0.36 mmol) and NMM (0.2 mL, dry) in DMF (1 mL, dry) at room temperature with stirring. The stirring was continued for 30 min. at room temperature. This mixture was added to amine with stirring at room temperature and stirring was continued at room temperature overnight, followed by purification by HPLC to give the desired material as bis-TFA salt (17 mg, 13% yield) with no distinct melting point.

NMR [DMSO-$d_6$]: 11.95(1H, s); 10.47(1H, s); 10.27(1H, s); 10.01(1H, s); 9.97(1H, s); 9.60(2H, br, TFA); 8.39(1H, s); 8.13(2H, br); 7.91(1H, d, J=8.7 Hz); 7.61(1H, d, J=8.7 Hz); 7.49(1H, s); 7.43(2H, s); 7.21(2H, s); 7.14(2H, s); 6.98(2H, s); 4.43(4H, m); 3.88(6H, s); 3.29(4H, m); 3.20-2.73(20H, m); 1.80(4H, m); 1.66-1.55(6H, m); 0.96(12H, d, J=6.5 Hz). IR [KBr]: 1676, 1647, 1584, 1533, 1443, 1404, 1200, 1136 $cm^{-1}$. HRFABMS: Found 1084.6; calculated for $C_{58}H_{82}N_{15}O_6$ 1084.6

Example 20

2-({[4-({4-(Acetylamino)-1-methyl-1H-imidazol-2-yl]carbonyl}amino)-1-methyl-1H-pyrrol-2-yl]carbonyl}amino)-N-[3-(dimethylamino)propyl]-5-isopropyl-1,3-thiazole-4-carboxamide N-[3-(Dimethylamino)propyl]-5-isopropyl-2-{[(1-methyl-4-nitro-1H-pyrrol-2-yl)carbonyl]amino}-1,3-thiazole-4-carboxamide (105 mg, 0.25 mmol; see Example 3, step (iv) above) and Pd/C-10% (100 mg) were suspended in methanol (20 mL) and hydrogenated for 2.5 h at room temperature. Filtration of catalyst over Kieselguhr under $N_2$, followed by removal of the solvent under reduced pressure gave the amine as an off-white solid, which was used without further purification. 4-Acetamido-1-methyl-2-imidazolecarboxylic acid sodium salt (120 mg, 0.7 mmol; prepared according to a standard literature procedure (see Tao, Z.; Fujiwara, T.; Saito, I.; Sugiyama, H. *Angew. Chem. Int. Ed. EN* 38(5), 650-653 (1999))) was dissolved in DMF (0.5 mL, dry), to which was added a solution of HBTU (137 mg, 0.36 mmol) and NMM (0.2 mL, dry) in DMF (1 mL, dry) at room temperature with stirring. The stirring was continued for 30 min. at room temperature. This mixture was added to the amine with stirring at room temperature and stirring was continued at room temperature overnight, followed by purification by HPLC to give the desired material as bis-TFA salt (30 mg, 22% yield) with no distinct melting point.

NMR [DMSO-$d_6$]: 1.27-1.28(6H, d, J=6.8 Hz, isopropyl); 1.87(2H, m); 2.02(3H, s); 2.78(6H, s, NMe$_2$); 3.07(2H, m); 3.32(2H, m); 3.89(3H, s, NMe); 3.95(3H, s, COMe); 4.19 (1H, m, isopropyl); 7.44(2H, m); 7.48(1H, m); 7.97(1H, m); 9.3(1H, br); 10.00(1H, s); 10.23(1H, s); 12.03(1H, s). IR [KBr]: 1667, 1550, 1470, 1288, 1198, 1133 cm$^{-1}$. HRFABMS: Found 558.26332 calculated for $C_{25}H_{36}N_9O_4S$ 558.26110.

Example 21

4-(Acetylamino)-N-[1-isopentyl-5-({[1-methyl-5-({ [3-(4-methyl-1-piperazinyl)propyl]amino}carbonyl)-1H-pyrrol-3-yl]amino}carbonyl)-1H-pyrrol-3-yl]-1-methyl-1H-pyrrole-2-carboxamide N-[1-Isopentyl-5-({[1-methyl-5-({[3-(4-methyl-1-piperazinyl)propyl]-amino}carbonyl)-1H-pyrrol-3-yl] amino}carbonyl)-1H-pyrrol-3-yl]-1-methyl-4-nitro-1H-pyrrole-2-carboxamide (186 mg, 0.305 mmol; see Example 29, step (ii) below) was dissolved in methanol at 0° C. under N$_2$ with stirring to which Pd/C-10% (136 mg) was added. The reaction mixture was hydrogenated for 3 h at room temperature and atmospheric pressure with stirring. The catalyst was removed over Kieselguhr and the solvent was removed under reduced pressure. The amine so formed was dissolved in dichloromethane (10 mL) and this solution was divided in half. Acetyl chloride (12 mg, 12 µL, 0.153 mmol) was added dropwise with stirring at room temperature to the first half. The stirring was continued at room temperature overnight. The solvent was removed under reduced pressure and the crude product formed was dissolved in small amount of acetonitrile/water containing 0.1% TFA and purified by HPLC. Fractions containing the pure material were combined and freeze-dried to give off-white solid (45.5 mg, 40% yield) with no distinct melting point.

NMR [DMSO-$d_6$]: 9.87(1H, s); 9.86(1H, s); 9.79(1H, s); 8.09(1H, t, unresolved); 7.26(1H, d, J=1.7 Hz); 7.14(1H, d, J=1.7 Hz); 7.13(1H, d, J=1.7 Hz); 7.01(1H, d, J=1.7 Hz); 6.91(1H, d, J=1.7 Hz); 6.86(1H, d, J=1.7 Hz); 4.31(2H, t, J=6.9 Hz); 3.83(3H, s); 3.81(3H, s); 3.24(2H, q, J=6.4 Hz); 3.10-2.60(8H, br, & 3H, s); 1.97(3H, s); 1.77(2H, m); 1.58-1.46(3H, m); 0.90(6H, d, J=6.4 Hz). IR [KBr]: 1675, 1647, 1584, 1535, 1459, 1436, 1402, 1197, 1132 cm$^{-1}$. HRFABMS: Found 622.38301; calculated for $C_{32}H_{48}N_9O_4$ 622.38293.

Example 22

N-[1-Isopentyl-5-({[1-methyl-5-({[3-(4-methyl-1-piperazinyl)propyl]-amino}carbonyl)-1H-pyrrol-3-yl]amino}carbonyl)-1H-pyrrol-3-yl]-4-[(3-methoxybenzoyl)amino]-1-methyl-1H-pyrrole-2-carboxamide To the second half of the amine solution (see Example 21 above) was added m-methoxybenzoyl chloride (26 mg, 26 µL, 0.153 mmol) was added dropwise at room temperature with stirring. The stirring was continued overnight at room temperature. The solvent was removed under reduced pressure and the crude product was purified by HPLC. The product was obtained as light brown solid (60.8 mg, 48% yield).

NMR [DMSO-$d_6$]: 10.28(1H, s); 9.95(1H, s); 9.88(1H, s); 8.09(1H, t, unresolved); 7.53-7.47(2H, m); 7.43(1H, t, J=7.8 Hz); 7.32(1H, d, J=1.7 Hz); 7.29(1H, d, J=1.7 Hz); 7.15-7.11 (3H, m); 7.02(1H, d, J=1.7 Hz); 6.92(1H, d, J=1.7 Hz); 4.32 (2H, t, J=6.6 Hz); 3.88(3H, s); 3.83(3H, s); 3.81(3H, s); 3.24(2H, q, J=6.0 Hz); 3.10-2.40(8H, br, & 3H, s); 1.77(2H, br); 1.59-1.47(3H, m); 0.91(6H, d, J=6.4 Hz). IR [KBr]: 1677, 1645, 1583, 1535, 1462, 1435, 1402, 1263, 1197, 1132 cm$^{-1}$. HRFABMS: Found 714.40764; calculated for $C_{38}H_{52}N_9O_5$ 714.40914.

Example 23

N-[5-({[3-(Dimethylamino)propyl]amino}carbonyl)-1-methyl-1H-pyrrol-3-yl]-4-({[5-(formylamino)-2-methyl-3-thienyl]carbonyl}amino)-1-isopentyl-1H-pyrrole-2-carboxamide (i) Ethyl 2-methyl-4,5-dihydro-3-thiophenecarboxylate A standard procedure was employed (see Pallab Chatterjee, Patrick J. Murphy, Rosanna Pepe and Michael Shaw *J. Chem. Soc., Perkin Trans. 1* 17, 2403-2406 (1994)) to give the product as colorless oil (96% yield).

(ii) Ethyl 2-methyl-3-thiophenecarboxylate

A standard procedure was employed (see Pallab Chatteree, Patrick J. Murphy, Rosanna Pepe and Michael Shaw *J. Chem. Soc., Perkin Trans. 1* 17, 2403-2406 (1994)) to give the product as colorless oil (82% yield).

(iii) 2-Methyl-3-thiophenecarboxylic acid

Ethyl 2-methyl-3-thiophenecarboxylate (3.42 g, 20.09 mmol; see step (ii) above) was dissolved in ethanol (5 mL) to which was added a solution of sodium hydroxide (3.2145 mg, 80.362 mmol) in water (10 mL). The reaction mixture was heated under reflux for 2 h. The volume was reduced to half under reduced pressure at 40° C. and the residue was cooled with ice water. Dilute HCl was added dropwise with stirring until pH 2. The white solid material was filtered off, washed with water and dried under reduced pressure at 50° C. to give the required material (2.1850 mg, 77% yield), m.p. 115-117° C., lit. m.p. 116-117° C. (see D. W. Knight, A. P. Nott *J. Chem. Soc., Perkin Trans. 1* 791-794 (1983)).

(iv) 2-Methyl-5-nitro-3-thiophenecarboxylic acid

A mixture of concentrated nitric acid (10 mL, sp.gr. 1.42) and concentrated sulphuric acid (6 mL) was mechanically stirred in a round-bottomed flask and cooled to (−10° C.) by a dry ice methanol bath. The temperature was kept below (−5° C.) while 2-methyl-3-thiophenecarboxylic acid (996 mg, 7.006 mmol; see step (iii) above) was added in small portions. The reaction mixture was stirred at the same temperature for 15 min. and then was poured over ice water. The solid material that precipitated was filtered off, washed with water and dried to give light brown solid (883 mg; 67% yield), m.p. 177-180° C.

NMR [DMSO-$d_6$]: 13.35(1H, br); 8.11(1H, s); 2.76(3H, s). IR [KBr]: 1706, 1543, 1514, 1457, 1335, 1257 cm$^{-1}$. HRE-IMS: Found 186.99431; calculated for $C_6H_5NO_4S$ 186.99393.

(v) N-[5-({[3-(Dimethylamino)propyl]amino}carbonyl)-1-methyl-1H-pyrrol-3-yl]-1-isopentyl-4-{[(2-methyl-5-nitro-3-thienyl)carbonyl]amino}-1H-pyrrole-2-carboxamide N-[5-({[3-(Dimethylamino)propyl]amino}carbonyl)-1-methyl-1H-pyrrol-3-yl]-1-isopentyl-4-nitro-1H-pyrrole-2-carboxamide (204 mg, 0.463 mmol; see Example 10, step (i) above) was dissolved in methanol (25 mL). The reaction mixture was cooled to 0° C. and then Pd/C-10% (121 mg) was added portion-wise under $N_2$ with stirring. The reaction mixture was hydrogenated for 5 h at room temperature and atmospheric pressure. The catalyst was removed over Kieselguhr and the solvent was then removed under reduced pressure. 2-Methyl-5-nitro-3-thiophenecarboxylic acid (87 mg, 0.463 mmol; see step (iv) above) was dissolved in thionyl chloride (2 mL) then heated until reflux for 5 h. The excess thionyl chloride was is removed under reduced pressure to give the acid chloride, which was dissolved in DCM (5 mL). The amine was dissolved in DCM (5 mL) to which N-methyl morpholine (0.1 mL) was added followed by the acid chloride, which was added dropwise at room temperature with stirring. The stirring was continued at room temperature overnight. The volatile material was removed under reduced pressure and the crude product was then purified by column chromatography using 2.5/2.5/0.6 mL ethyl acetate/methanol/TEA) $R_F$=0.5. The product was obtained as amorphous yellow material (237 mg, 90% yield) with no distinct melting point.

NMR [DMSO-$d_6$]: 10.37(1H, s); 9.94(1H, s); 8.58(1H, s); 8.12(1H, t, J=5.6 Hz); 7.35(1H, d, J=1.7 Hz); 7.18(1H, d, J=1.7 Hz); 7.14(1H, d, J=1.7 Hz); 7.01(1H, d, J=1.7 Hz); 6.86(1H, d, J=1.7 Hz); 4.34(1H, t, J=6.9 Hz); 3.80(3H, s); 3.22(2H, q, J=6.5 Hz); 2.77(3H, s); 2.64(2H, m); 2.44(6H, s); 1.73(2H, quintet, J=6.7 Hz); 1.59-1.45(3H, m); 0.90(6H, d, J=6.4 Hz). IR [KBr]: 1675, 1650, 1583, 1537, 1465, 1437, 1403, 1263, 1202, 1133 $cm^{-1}$. HRFABMS: Found: 572.26551; calculated for $C_{27}H_{37}N_7O_5S$ 572.26580.

(vi) N-[5-({[3-(Dimethylamino)propyl]amino}carbonyl)-1-methyl-1H-pyrrol-3-yl]-4-({[5-(formylamino)-2-methyl-3-thienyl]carbonyl}amino-1-isopentyl-1-pyrrole-2-carboxamide N-[5-({[3-(dimethylamino)propyl]amino}carbonyl)-1-methyl-1H-pyrrol-3-yl]-1-isopentyl-4-{[(2-methyl-5-nitro-3-thienyl)carbonyl]amino}-1H-pyrrole-2-carboxamide (110 mg, 0.193 mmol; see step (v) above) was dissolved in ethanol (20 mL) and cooled to 0° C. Pd/C-10% (120 mg) was added under $N_2$ with stirring and the reaction was hydrogenated at room temperature and atmospheric pressure for 3 h. The catalyst was removed over Kieselguhr then ethyl formate (20 mL) was added to the ethanolic solution. The reaction mixture was heated under reflux for 3 days. The volatile material was then removed under reduced pressure and the crude product was purified by HPLC. The product was obtained as solid material with no distinct melting point (23 mg, 17.4% yield).

NMR [DMSO-$d_6$]: 11.32(1H, s); 9.94(1H, s); 9.88(1H, s); 9.24(1H, br, TFA); 8.29(1H, s); 8.14(1H, t, J=5.9 Hz); 7.29 (1H, d, J=1.7 Hz); 6.95(1H, s); 6.93(1H, d, J=1.7 Hz); 4.32 (1H, t, J=7.0 Hz); 3.81(3H, s); 3.25(2H, q, J=5.1 Hz); 3.06 (2H, m); 2.79(6H, d, J=3.5 Hz); 2.5(3H, s); 1.83(2H, quintet, J=6.7 Hz); 1.57-1.49(3H, m); 0.90(6H, d, J=6.4 Hz). IR [KBr]: 1671, 1651, 1582, 1537, 1464, 1403, 1200, 1179, 1132 $cm^{-1}$. HRFABMS: Found: 570.28565; calculated for $C_{28}H_{40}N_7O_4S$ 570.28625.

Example 24

N-[5-({[5-({[3-(dimethylamino)propyl]amino}carbonyl)-1-methyl-1H-pyrrol-3-yl]amino}carbonyl)-1-methyl-1H-pyrrol-3-yl]-5-isopropyl-2-[(3-methoxybenzoyl)amino]-1,3-thiazole-4-carboxamide (i) Methyl 5-isopropyl-2-[(3-methoxybenzoyl)amino]-1,3-thiazole-4-carboxylate Methyl 2-amino-5-isopropyl-1,3-thiazole-4-carboxylate (383 mg, 1.913 mmol; see Example 3, step (i) above) was dissolved in DCM (10 mL) at room temperature with stirring. N-methyl morpholine (0.3 mL) was added followed by 3-methoxybenzoyl chloride (326 mg, 1.913 mmol) at room temperature with stirring. The reaction mixture was heated until reflux for 10 min. and then was left stirring at room temperature overnight. The solvent was removed under reduced pressure and the crude product was purified by column chromatography using silica gel and 1:2 ethyl acetate/petroleum ether. Fractions containing the required material ($R_F$=0.4) were collected and the solvents were removed under reduced pressure to give the product as white solid material (530 mg, 83% yield), m.p. 60-63° C.

NMR [$CDCl_3$]: 9.89(1H, s); 7.45-7.38(3H, m); 7.16-7.13 (1H, m); 4.16(1H, heptet, J=6.8 Hz); 3.86(3H, s); 3.85(3H, s); 1.40(6H, d, J=6.8 Hz). IR [KBr]: 2958, 1720, 1669, 1547, 1463, 1298, 1208, 1045, 822, 743 $cm^{-1}$. HRFABMS: Found: 335.10620; calculated for $C_{16}H_{19}N_2O_4S$ 335.10655.

(ii) 5-Isopropyl-2-[(3-methoxybenzoyl)amino]-1,3-thiazole-4-carboxylic acid

Methyl 5-isopropyl-2-[(3-methoxybenzoyl)amino]-1,3-thiazole-4-carboxylate (330 mg, 0.998 mmol; see step (i) above) was dissolved in ethanolic KOH (561 mg, in 10 mL ethanol; 10 mmol). The reaction mixture was heated under reflux for 3 h, and then it was cooled to 0° C. $HCl_{(conc.)}$ was added dropwise with stirring at 0° C. and the resulting solid was filtered off, washed with water and dried under reduced pressure at 45° C. overnight. The product was obtained as white solid material (290 mg, 91% yield), m.p.>230° C. [sublimation].

NMR [DMSO-$d_6$]: 7.69(2H, m); 7.44(1H, t, J=3.9 Hz); 7.19(1H, m); 4.06(1H, heptet, J=6.8 Hz); 3.84(3H, s); 1.31 (6H, d, J=6.8 Hz). IR [KBr]: 2963, 1672, 1555, 1463, 1306, 1221, 1043, 936, 820, 736 $cm^{-1}$. HRFABMS: Found: 321.09056; calculated for $C_{15}H_{17}N_2O_4S$ 321.09090.

(iii) N-[5-({[5-({[3-(dimethylamino)propyl]amino}carbonyl)-1-methyl-1H-pyrrol-3-yl]amino}carbonyl)-1-methyl-1H-pyrrol-3-yl]-5-isopropyl-2-[(3-methoxybenzoyl)amino]-1,3-thiazole-4-carboxamide N-[5-({[3-(Dimethylamino)propyl]amino}carbonyl)-1-methyl-1H-pyrrol-3-yl]-1-methyl-4-nitro-1H-pyrrole-2-carboxamide (113 mg, 0.300 mmol; see Tetrahedron 56, 5225-5239, (2000)) was suspended in methanol (25 mL) at 0° C. with stirring under $N_2$. Pd/C-10% (61 mg) was added with stirring under $N_2$ and then the reaction mixture was hydrogenated at room temperature and atmospheric pressure for 3 h. The catalyst was removed over Kieselguhr and the solvent was then removed under reduced pressure to give the amine, which was used in the coupling reaction without further purification. 5-Isopropyl-2-[(3-methoxybenzoyl)amino]-1,3-thiazole-4-carboxylic acid (96 mg, 3.00 mmol; see step (ii) above) was dissolved in thionyl chloride (2 mL) then heated under reflux for 3 h. The excess thionyl chloride was removed under reduced pressure and the acid chloride so formed was dissolved in DCM (5 mL). The amine was dissolved in DCM (5 mL), to which N-methyl morpholine (0.2 mL) was added. The acid chloride solution was added dropwise at room temperature with stirring and then the stirring was continued overnight at room temperature. The volatile material was removed under reduced pressure and the crude product was purified by HPLC. Fractions containing the required material were collected and freeze-dried to give the product as pale yellow solid (73 mg, 32% yield) with no distinct melting point.

NMR [DMSO-$d_6$]: 12.63(1H, s); 9.88(1H, s); 9.55(1H, s); 9.29(1H, br); 8.14(1H, t, 5.8 Hz); 7.69(1H, s); 7.67(1H, s); 7.48(1H, t, J=5.9 Hz); 7.26(1H, d, 1.7 Hz); 7.23(1H, m);

7.18(1H, d, J=1.7 Hz); 7.13(1H, d, J=1.7 Hz); 6.94(1H, d, 1.7 Hz); 4.19(1H, heptet, J=6.8 Hz); 3.86(6H, s); 3.82(3H, s); 3.24(2H, q, J=6.7 Hz); 3.07(2H, m); 2.79(6H, d, J=3.8 Hz); 1.86(2H, quintet, J=6.7 Hz); 1.33(6H, d, J=6.8 Hz). IR [KBr]: 1660, 1547, 1466, 1436, 1403, 1286, 1199, 1137, 1043 cm$^{-1}$. HRFABMS: Found: 649.29379; calculated for $C_{32}H_{41}N_8O_5S$ 649.29206.

Example 25

N-[5-({[3-(Dimethylamino)propyl]amino}carbonyl)-1-methyl-1H-pyrrol-3-yl]-4-{[(5-{[(9,10-dioxo-9,10-dihydro-2-anthracenyl)carbonyl]amino}-2-methyl-3-thienyl)carbonyl]amino}-1-isopentyl-1H-pyrrole-2-carboxamide N-[5-({[3-(Dimethylamino)propyl]amino}carbonyl)-1-methyl-1H-pyrrol-3-yl]-1-isopentyl-4-{[(2-methyl-5-nitro-3-thienyl)carbonyl]amino}-1H-pyrrole-2-carboxamide (127 mg, 0.223 mmol; see Example 23, step (v) above) was dissolved in methanol (25 mL) at 0° C. under $N_2$ with stirring. Pd/C-10% (114 mg) was added and the reaction mixture was hydrogenated at room temperature and atmospheric pressure for 3.5 h. The catalyst was removed over Kieselguhr and the solvent was removed under reduced pressure to give the amine, which was used in the subsequent coupling reaction. 9,10-Dioxo-9,10-dihydro-2-anthracenecarboxylic acid (Aldrich) (56 mg, 0.223 mmol) was dissolved in DMF (1 mL, dry), to which HBTU (127 mg, 0.335 mmol) and N-methyl morpholine (0.2 mL, dry) were added with stirring under $N_2$. The amine was dissolved in DMF (1 mL, dry) and was added dropwise to the reaction mixture. The reaction mixture was left stirring at room temperature overnight. The reaction mixture was then diluted with a mixture made of ethyl acetate/methanol 9:1 (50 mL), after which it was extracted with water. The organic layer was dried over $MgSO_4$, filtered and the solvents removed under reduced pressure. The crude product obtained was purified by HPLC to give the pure material as brown solid with no distinct melting point (33 mg, 19% yield).

NMR [DMSO-d$_6$]: 21.04(1H, s); 10.04(1H, s); 9.91(1H, s); 9.23(1H, br, TFA); 8.83(1H, d, J=1.7 Hz); 8.50(1H, dd, J=1.8 Hz & J=8.1 Hz); 8.42(1H, d, J=8.1 Hz); 8.29-8.25(2H, m); 8.15(1H, t, J=5.9 Hz); 8.00-7.97(2H, m); 7.33(1H, d, J=1.7 Hz); 7.21(1H, s); 7.17(1H, d, J=1.7 Hz); 7.02(1H, d, J=1.7 Hz); 6.94(1H, d, J=1.7 Hz); 4.33(2H, t, J=7.1 Hz); 3.82(3H, s); 3.24(2H, q, J=5.1 Hz); 3.08(2H, m); 2.79(6H, d, J=3.5 Hz); 2.59(3H, s); 1.84(2H, quintet, J=6.7 Hz); 1.60-1.50(3H, m); 0.91(6H, d, J=6.4 Hz). IR [KBr]: 1674, 1653, 1585, 1539, 1464, 1404, 1487, 1200, 1177, 1135 cm$^{-1}$. HRFABMS: Found: 776.32284; calculated for $C_{42}H_{46}N_7O_6S$ 776.32303.

Example 26

N-[1-(Cyclopropylmethyl)-5-({[5-({[3-(dimethylamino)propyl]amino}-carbonyl)-1-methyl-1H-pyrrol-3-yl]amino}carbonyl)-1H-pyrrol-3-yl]-4-(formylamino)-1-methyl-1H-pyrrole-2-carboxamide (i) Ethyl 1-(cyclopropylmethyl)-4-nitro-1H-pyrrole-2-carboxylate Ethyl 4-nitro-1H-pyrrole-2-carboxylate (1.042 g, 5.626 mmol; see Example 1, step (i) above) was dissolved in DMF (20 mL, dry) to which potassium metal (0.435 g, 11.124 mmol) was added. The reaction mixture was heated to 100° C. with stirring and it was left at that temperature for 1 h. The reaction mixture was cooled to 50-60° C. then (chloromethyl)cyclopropane (1.000 g, 11.044 mmol) [purchased from Aldrich] and KI (1.349 g, 8.127 mmol) were added and the reaction mixture was heated again with stirring to 80° C. for 5 h, after which time it was left stirring overnight at room temperature. The reaction mixture was diluted with brine (50 mL) and extracted with ethyl acetate (3×100 mL). The combined organic extracts were collected and the solvent was removed under reduced pressure. The crude product obtained (containing some DMF) was purified by flash chromatography using silica gel and 1/10 ethyl acetate/n-hexane. The product as white microcrystalline solid [$R_F$=0.2] was obtained (1.070 g, 80% yield), m.p. 65-66° C.

NMR [DMSO-d$_6$]: 8.34(1H, d, J=1.3 Hz); 7.35(1H, d, J=1.3 Hz); 4.30-4.24(2H, q, J=7.1 Hz); 4.21(2H, d, J=7.2 Hz); 1.34-1.23(2H; t, J=7.1 Hz & 1H, m); 0.53-0.45(2H, m); 0.42-0.38(2H, m). IR [KBr]: 3142, 2996, 2921, 1704, 1502, 1310, 1270, 1225, 1184, 1091 cm$^{-1}$. HREIMS: Found 238.09585; calculated for $C_{11}H_{14}N_2O_4$ 238.09536.

(ii) 1-(Cyclopropylmethyl-4-nitro-1H-pyrrole-2-carboxylic acid

Ethyl 1-(cyclopropylmethyl)-4-nitro-1H-pyrrole-2-carboxylate (482 mg, 2.023 mmol; see step (i) above) was dissolved in ethanol (4 mL) to which a solution of NaOH (393 mg, 9.825 mmol) in water (10 mL) was added. The reaction mixture was heated under reflux for 2 h then cooled to 0° C. HCl conc. was added dropwise with stirring until the solution reached pH 2. The white solid material, which precipitated was filtered off, washed with water and dried under reduced pressure at 60° C. overnight. The product was obtained as white solid material (382 mg, 90% yield), m.p. 215-217° C.

NMR [DMSO-d$_6$]: 13.14(1H, br); 8.29(1H, d, J=2.4 Hz); 7.29(1H, d, J=2.1 Hz); 4.20(2H, d, J=2.2 Hz); 1.34-1.27(1H, m); 0.52-0.38(4H, m). IR [KBr]: 3115, 3005, 2922, 2854, 1680, 1540, 1517, 1481, 1420, 1314 cm$^{-1}$. HREIMS: Found 210.06469; calculated for $C_9H_{10}N_2O_4$ 210.06406.

(iii) 1-(Cyclopropylmethyl)-N-[5-({[3-(dimethylamino)propyl]amino}-carbonyl)-1-methyl-1H-pyrrol-3-yl]-4-nitro-1H-pyrrole-2-carboxamide N-[3-(Dimethylamino)propyl]-1-methyl-4-nitro-1H-pyrrole-2-carboxamide (100 mg, 0.393 mmol; see *Tetrahedron* 56, 5225-5239 (2000)) was dissolved in methanol (25 mL) to which Pd/C-10% (75 mg) was added at 0° C. under $N_2$ with stirring. The reaction mixture was hydrogenated for 2 h at room temperature and atmospheric pressure. The catalyst was removed over Kieselguhr and the solvent was removed under reduced pressure. The amine so formed was dissolved in DMF (2 mL, dry) to which was added 1-(cyclopropylmethyl)-4-nitro-1H-pyrrole-2-carboxylic acid (83 mg, 0.393 mmol; see step (ii) above), HBTU (298 mg, 0.786 mmol), NMM (200 µL, dry) with stirring at room temperature. The stirring was continued for 48 h. The reaction mixture was diluted with ethyl acetate (50 mL) and extracted with NaHCO$_3$ (25 mL, saturated). The water layer was extracted again with ethyl acetate (50 mL). The combined organic extract was dried over MgSO$_4$, filtered and the solvent removed under reduced pressure to give the crude product as pale yellow oil. Purification by flash column chromatography over silica gel using 1/2/0.1 methanol/ethyl acetate/TEA gave the required product as glassy yellow material [$R_F$=0.5] (130 mg, 80% yield) with no distinct melting point.

NMR [DMSO-d$_6$]: 10.26(1H, s); 8.24(1H, d, J=1.9 Hz); 8.10(1H, t, J=5.6 Hz); 7.57(1H, d, J=1.9 Hz); 7.21(1H, d, J=1.9 Hz); 6.83(1H, d, J=1.9 Hz); 4.27(2H, d, J=7.2 Hz); 3.81(3H, s); 3.21-3.16(2H, q, J=6.9 Hz); 2.28(2H, t, J=7.1

Hz); 2.17(6H, s); 1.65-1.59(2H, quintet, J=7.1 Hz); 1.34-1.29 (1H, m); 0.51-0.38(4H, m). IR [KBr]: 3283, 3126, 2944, 1642, 1573, 1532, 1504, 1463, 1427, 1389, 1309, 1233 cm$^{-1}$. HRFABMS: Found 417.22460; calculated for $C_{20}H_{29}N_6O_4$ 417.22503.

(iv) N-[1-(Cyclopropylmethyl)-5-({[5-({[3-(dimethylamino)propyl]amino}-carbonyl)-1-methyl-1H-pyrrol-3-yl]amino}carbonyl)-1H-pyrrol-3-yl]-1-methyl-4-nitro-1H-pyrrole-2-carboxamide 1-(Cyclopropylmethyl)-N-[5-({[3-(dimethylamino)propyl]amino}carbonyl)-1-methyl-1H-pyrrol-3-yl]-4-nitro-1H-pyrrole-2-carboxamide (120 mg, 0.288 mmol; see step (iii) above) was dissolved in methanol (25 mL) to which Pd/C-10% (97 mg) was added at 0° C. under $N_2$ with stirring. The reaction mixture was hydrogenated for 4 h at room temperature and atmospheric pressure. The catalyst was removed over Kieselguhr and the solvent was removed under reduced pressure to give the amine, which was used in the next step without any purification. The amine so formed was dissolved in DMF (2 mL, dry) to which 1-methyl-4-nitro-1H-pyrrole-2-carboxylic acid (57 mg, 0.288 mmol; see *Tetrahedron* 56, 5225-5239 (2000)), HBTU (218 mg, 0.576 mmol), and NMM (200 µL, dry) were added at room temperature with stirring. The stirring was continued at room temperature overnight. The reaction mixture was diluted with ethyl acetate (50 mL) and extracted with $NaHCO_3$ (25 mL, sat.). The water layer was extracted again with ethyl acetate (50 mL). The combined organic extract was dried over $MgSO_4$, filtered and the solvent was removed under reduced pressure. The crude product obtained was purified by column chromatography using silica gel and 1/2/0.1 methanol/ethyl acetate/TEA. Fractions containing the pure product [$R_F$=0.4] were collected and the solvents were removed under reduced pressure at 50° C. to give the required product as glassy yellow solid (110 mg, 71% yield) with no distinct melting point.

NMR [DMSO-$d_6$]: 10.27(1H, s); 9.94(1H, s); 8.18(1H, d, J=1.7 Hz); 8.06(1H, t, J=5.2 Hz); 7.59(1H, d, J=1.9 Hz); 7.36(1H, d, 1.9 Hz); 7.18(1H, d, J=1.9 Hz); 7.02(1H, d, J=1.9 Hz); 6.83(1H, d, J=1.9 Hz); 4.19(2H, d, J=7.0 Hz); 3.97(3H, s); 3.80(3H, s); 3.21-3.16(2H, q, J=6.9 Hz); 2.26(2H, t, J=7.1 Hz); 2.15(6H, s); 1.65-1.58(2H, quintet, J=7.1 Hz); 1.26-1.13 (1H, m); 0.47-0.42(2H, m); 0.33-0.31(2H, m). IR [KBr]: 3286, 3126, 2938, 1646, 1580, 1531, 1462, 1439, 1400, 1309, 1248 cm$^{-1}$. HRFABMS: Found 539.27295; calculated for $C_{26}H_{35}N_8O_5$ 539.27304.

(v) N-[1-(Cyclopropylmethyl)-5-({[5-({[3-(dimethylamino)propyl]amino}-carbonyl)-1-methyl-1H-pyrrol-3-yl]amino}carbonyl)-1H-pyrrol-3-yl]-4-(formylamino)-1-methyl-1H-pyrrole-2-carboxamide N-[1-(Cyclopropylmethyl)-5-({[5-({[3-(dimethylamino)propyl]amino}-carbonyl)-1-methyl-1H-pyrrol-3-yl]amino}carbonyl)-1H-pyrrol-3-yl]-1-methyl-4-nitro-1H-pyrrole-2-carboxamide (100 mg, 0.186 mmol; see step (iv) above) was dissolved in ethanol (25 mL) to which Pd/C-10% (78 mg) was added at 0° C. under $N_2$ with stirring. The reaction mixture was hydrogenated for 3 h at room temperature and atmospheric pressure. The catalyst was removed over Kieselguhr. Ethyl formate was added to the ethanolic solution of the amine and the reaction mixture was heated under reflux for 48 h. Ethanol and excess ethyl formate were removed under reduced pressure and the crude product was purified by HPLC. The product was obtained as pale yellow solid (52 mg, 42% yield) after freeze drying with no distinct melting point.

NMR [DMSO-$d_6$]: 10.04(1H, s); 9.91(1H, s); 9.90(1H, s); 9.28(1H, br, TFA); 8.16-8.13(2H, t&d); 7.31(1H, d, J=1.7 Hz); 7.19(1H, d, J=1.7 Hz); 7.16(1H, d, J=1.7 Hz); 7.05(1H, d, J=1.7 Hz); 6.95(1H, d, 1.7 Hz); 6.93(1H, d, J=1.7 Hz); 4.18(2H, d, J=7.0 Hz); 3.85(3H, s); 3.81(3H, s); 3.26-3.22 (2H, q, J=6.3 Hz); 3.07(2H, m); 2.79(2H, d, J=4.3 Hz); 1.87-1.82(2H, quintet, J=6.6 Hz); 1.23(1H, m); 0.47-0.42(2H, m); 0.33-0.29(2H, m). IR[KBr]: 3410, 3294, 1674, 1649, 1582, 1533, 1464, 1438, 1403, 1201, 1132 cm$^{-1}$. HRFABMS: Found 537.29360; calculated for $C_{27}H_{37}N_8O_4$ 537.29378.

Example 27

1-Cyclopentyl-N-[5-({[3-(dimethylamino propyl]amino}carbonyl-1-methyl-1H-pyrrol-3-yl]-4-({[4-(formylamino)-1-methyl-1H-pyrrol-2-yl]-carbonyl}amino)-1H-pyrrole-2-carboxamide (i) Ethyl 1-cyclopentyl-4-nitro-1H-pyrrole-2-carboxylate Ethyl 4-nitro-1H-pyrrole-2-carboxylate (1.006 g, 5.432 mmol; see Example 1, step (i) above) was dissolved in DMF (20 mL, dry) to which was added potassium metal (0.492 g, 12.582 mmol) then it was heated to 80° C. and then it was left at that temperature for 1 h with stirring. The reaction mixture was cooled to 50-60° C. after which bromocyclopentane (1 mL, 1.390 g, 9.326 mmol) was added followed by KI (1.548 g, 9.326 mmol). The reaction mixture was heated again for 5 h with stirring at 80° C., after which time it was left stirring at room temperature under $N_2$, overnight. The reaction mixture was diluted with brine under $N_2$, at room temperature, and then it was extracted with ethyl acetate (3×100 mL). The combined organic extract was dried over $MgSO_4$, filtered and the solvent removed under reduced pressure to give the crude product (containing some DME). The product was purified using column chromatography [silica gel, 1/10 ethyl acetate/n-hexane ($R_F$=0.24)]. Fractions containing the pure material were collected and the solvent removed to give pale yellow oil (440 mg, 32% yield).

NMR [CDCl$_3$]: 7.77(1H, d, J=2.0 Hz); 7.45(1H, d, J=2.0 Hz); 5.57-5.50(1H, quintet, J=6.6 Hz); 4.33(2H, q, J=7.1 Hz); 2.30-2.24(2H, m); 1.98-1.75(6H, m); 1.37(3H, t, J=7.1 Hz). IR[KBr]: 2965, 2875, 1717, 1534, 1508, 1426, 1335, 1294, 1222, 1187, 1084 cm$^{-1}$. HRFABMS: Found 253.11824; calculated for $C_{12}H_{17}N_2O_4$ 253.11883.

(ii) 1-Cyclopentyl-4-nitro-1H-pyrrole-2-carboxylic acid

Ethyl 1-cyclopentyl-4-nitro-1H-pyrrole-2-carboxylate (430 mg, 1.706 mmol; see step (i) above) was dissolved in ethanol (4 mL) to which a solution of NaOH (408 mg, 10.20 mmol) in water (10 mL) was added. The reaction mixture was heated under reflux for 2 h, and then it was cooled to 0° C. Hydrochloric acid (conc.) was added dropwise with stirring until pH 2. The solid was filtered off, washed with water and dried at 45° C. for 48 h to give white solid material (340 mg, 89% yield). Mp 195-198° C.

NMR [DMSO-$d_6$]: 13.13(1H, br); 8.27(1H, d, J=2.0 Hz); 7.29(1H, d, J=2.0 Hz); 5.45(1H, quintet, J=7.1 Hz); 2.16-2.07 (2H, m); 1.88-1.78(4H, m); 1.65-1.61(2H, m). IR [KBr]: 3152, 2964, 2880, 1683, 1508, 1430, 1331, 1292, 1078, 911 cm$^{-1}$. HREIMS: Found 224.07926; calculated for $C_{10}H_{12}N_2O_4$ 224.07971.

(iii) 1-Cyclopentyl-N-[5-({[3-(dimethylamino)propyl]amino}carbonyl)-1-methyl-1H-pyrrol-3-yl]-4-nitro-1H-pyrrole-2-carboxamide N-[3-(Dimethylamino)propyl]-1-methyl-4-nitro-1H-pyrrole-2-carboxamide (100 mg, 0.393 mmol; see *Tetrahedron* 56, 5225-5239 (2000)) was dissolved in methanol (25 mL) to which Pd/C-10% (90 mg) was added at 0° C. under $N_2$ with stirring. The reaction mixture was hydrogenated for 3 h at room temperature and atmospheric pressure. The catalyst was removed over Kieselguhr and the solvent was removed under reduced pressure. The amine so formed was dissolved in DMF (2 mL, dry) to which 1-(cyclopentyl-4-nitro-1H-pyrrole-2-carboxylic acid (88 mg, 0.393 mmol; see step (ii) above) was added followed by HBTU (298 mg, 0.786 mmol) and NMM (200 µL, dry) with stirring at room temperature. The reaction mixture was diluted with ethyl acetate (50 mL) and extracted with NaHCO$_{3(sat.)}$ (25 mL). The water layer was extracted again with ethyl acetate (50 mL). The combined organic extract was dried over MgSO$_4$, filtered and the solvent removed under reduced pressure to give the crude product which was purified by column chromatography using silica gel and 1/2/0.1 methanol/ethyl acetate/TEA. The product was obtained as yellow oil R$_F$=0.45 (157 mg, 93% yield).

NMR [DMSO-d$_6$]: 10.27(1H, s); 8.24(1H, d, J=1.7 Hz); 8.11(1H, t, J=5.2 Hz); 7.47(1H, s); 7.20(1H, d, J=1.7 Hz); 6.83(1H, d, J=1.7 Hz); 5.48(1H, quintet, J=7.4 Hz); 3.80(3H, s); 3.18(2H, q, J=6.6 Hz); 2.66(2H, m); 2.30(2H, t, J=7.1 Hz); 2.14(6H, s); 2.12(2H, m); 1.82(4H, m); 1.62(2H, quintet, J=7.1 Hz). IR [KBr]: 1644, 1575, 1534, 1504, 1437, 1401, 1313, 1287, 748 cm$^1$. HRFABMS: Found 431.24204; calculated for C$_{21}$H$_{31}$N$_6$O$_4$ 431.24068.

(iv) 1-Cyclopentyl-N-[5-({[3-(dimethylamino)propyl]amino}carbonyl)-1-methyl-1H-pyrrol-3-yl]-4-{[(1-methyl-4-nitro-1H-pyrrol-2-yl)carbonyl]-amino}-1H-pyrrole-2-carboxamide 1-Cyclopentyl-N-[5-({[3-(dimethylamino)propyl]amino}carbonyl)-1-methyl-1H-pyrrol-3-yl]-4-nitro-1H-pyrrole-2-carboxamide (157 mg, 0.365 mmol; see step (iii) above) was dissolved in methanol (25 mL) at 0° C. under N$_2$ with stirring, to which Pd/C-10% (80 mg) was added. The reaction mixture was hydrogenated for 2 h at room temperature and atmospheric pressure. The catalyst was removed over Kieselguhr and the solvent was removed under reduced pressure. The amine so formed was dissolved in DMF (2 mL, dry) to which 1-methyl-4-nitro-1H-pyrrole-2-carboxylic acid (62 mg, 0.365 mmol; see *Tetrahedron* 56, 5225-5239 (2000)), HBTU (277 mg, 0.730 mmol) and NMM (200 µL, dry) were added with stirring at room temperature. The stirring was continued overnight. The reaction mixture was diluted with ethyl acetate (50 mL) and extracted with NaHCO$_3$(sat) (25 mL). The water layer was extracted again with ethyl acetate (50 mL). The combined organic extract was dried over MgSO$_4$, filtered and the solvent removed under reduced pressure to give the crude product, which was purified by column chromatography using silica gel and 1/2/0.1 methanol/ethyl acetate/TEA, R$_F$=0.40. The product was obtained as glassy solid material with no distinct melting point (110 mg, 55% yield).

NMR [DMSO-d$_6$]: 10.28(1H, s); 9.96(1H, s); 8.18(1H, d, J=1.8 Hz); 8.07(1H, t, J=5.2 Hz); 7.58(1H, d, J=1.8 Hz); 7.41(1H, d, J=1.8 Hz); 7.18(1H, d, J=1.8 Hz); 6.93(1H, d, J=1.8 Hz); 6.85(1H, d, J=1.8 Hz); 5.53(1H, quintet, J=7.3 Hz); 3.97(3H, s); 3.80(3H, s); 3.20(2H, m); 2.83(2H, m); 2.42(2H, t, J=7.2 Hz); 2.27(6H, s); 2.09(2H, m); 1.79-1.64 (6H, m). IR [KBr]: 1642, 1584, 1529, 1505, 1403, 1309 cm$^{-1}$. HRFABMS: Found 553.28890; calculated for C$_{27}$H$_{37}$N$_8$O$_5$ 553.28869.

(v) 1-Cyclopentyl-N-[5-({[3-(dimethylamino)propyl]amino}carbonyl)-1-methyl-1H-pyrrol-3-yl]-4-({[4-(formylamino)-1-methyl-1H-pyrrol-2-yl]-carbonyl}amino)-1H-pyrrole-2-carboxamide 1-Cyclopentyl-N-[5-({[3-(dimethylamino)propyl]amino}carbonyl)-1-methyl-1H-pyrrol-3-yl]-4-{[(1-methyl-4-nitro-1H-pyrrol-2-yl)carbonyl]-amino}-1H-pyrrole-2-carboxamide (100 mg, 0.181 mmol; see step (iv) above) was dissolved in ethanol (20 mL) at 0° C. under N$_2$ with stirring, to which Pd/C-10% (92 mg) was added. The reaction mixture was hydrogenated at room temperature and atmospheric pressure for 3 h. The catalyst was removed over Kieselguhr and ethyl formate (25 mL) was added to the ethanolic solution. The reaction mixture was heated under reflux for 24 h. The solvent was removed under reduced pressure to give the crude product, which was purified by HPLC. Fractions containing the required material were collected and freeze dried to give the product as pale yellow solid (21 mg, 18% yield) with no distinct melting point.

NMR [DMSO-d$_6$]: 10.06(1H, s); 9.95(1H, s); 9.91(1H, s); 9.21(1H, br, TFA); 8.14(1H, t, J=6.0 Hz); 8.13(1H, d, J=1.7 Hz); 7.36(1H, d, J=1.7 Hz); 7.19(1H, d, J=1.7 Hz); 7.17(1H, d, J=1.7 Hz); 6.97(1H, d, J=1.7 Hz); 6.95(1H, d, J=1.7 Hz); 6.92(1H, d, J=1.7 Hz); 5.52(1H, quintet, J=7.5 Hz); 3.84(3H, s); 3.81(3H, s); 3.24(2H, m); 3.06(2H, m); 2.79(6H, d, J=3.3 Hz); 2.08(2H, m); 1.83(4H, m); 1.64(4H, m). IR [KBr]: 1674, 1647, 1582, 1536, 1463, 1440, 1406, 1201, 1131 cm$^{-1}$. HRFABMS: Found 551.30950; calculated for C$_{28}$H$_{39}$N$_8$O$_4$ 551.30943.

Example 28

N$^2$,N$^7$-Bis[5-({[4-({[3-(dimethylamino)propyl]amino}carbonyl)-5-isopropyl-1,3-thiazol-2-yl]amino}carbonyl)-1-methyl-1H-pyrrol-3-yl]-9,10-dihydro-2,7-phenanthrenedicarboxamide N-[3-(Dimethylamino)propyl]-5-isopropyl-2-{[(1-methyl-4-nitro-1H-pyrrol-2-yl)carbonyl]amino}-1,3-thiazole-4-carboxamide (170 mg, 0.402 mmol; see Example 3, step (iv) above) was suspended in methanol (25 mL) at 0° C. under N$_2$ with stirring, to which Pd/C-10% (104 mg) was added. The reaction mixture was hydrogenated for 6 h at room temperature and atmospheric pressure. The catalyst was removed over Kieselguhr and the solvent was removed under reduced pressure. The amine so formed was dissolved in DMF (2 mL, dry), to which 9,10-dihydro-2,7-phenanthrene-dicarboxylic acid (54 mg, 0.201 mmol; see *Tetrahedron* 56, 5225-5239 (2000)), HBTU (610 mg, 1.608 mmol) and NMM (200 mL, dry) were added at room temperature with stirring. The reaction mixture was stirred overnight at room temperature. The reaction mixture was diluted with ethyl acetate containing 5% methanol and NaHCO$_3$(sat). The organic layer was dried over MgSO$_4$, filtered and the solvent removed under reduced pressure to give the crude product, which was purified by HPLC. Fractions containing the required material were collected and freeze dried to give pale yellow solid with distinct melting point (46.3 mg, 19% yield).

NMR [DMSO-d$_6$]: 12.11(2H, s); 10.46(2H, s); 9.26(2H, br, TFA); 8.07-7.91(6H, m); 7.53(2H, s); 7.46(2H, s); 4.20 (2H, quintet, J=6.9 Hz); 3.92(6H, s); 3.33(4H, m); 3.07(4H, m); 2.97(2H, s); 2.96(2H, s); 2.80(12H, d, J=4.1 Hz); 1.87 (4H, quintet, J=7.7 Hz); 1.27(12H, d, J=6.9 Hz). IR [KBr]: 1660, 1548, 1468, 1284, 1199, 1132, 832, 800, 721 cm$^{-1}$. LRESMS: Found M+H=1017.4; [M+2]/2=509.5; calculated for C$_{52}$H$_{66}$N$_{12}$O$_6$S$_2$ M+H=1017.4; [M+2H]/2=509.3.

Example 29

4-(Formylamino)-N-[1-isopentyl-5-({[1-methyl-5-({[3-(4-methyl-1-piperazinyl)propyl]amino}carbonyl)-1H-pyrrol-3-yl]amino}carbonyl)-1H-pyrrol-3-yl]-1-methyl-1H-pyrrole-2-carboxamide (i) 1-Isopentyl-N-[1-methyl-5-({[3-(4-methyl-1-piperazinyl)propyl]amino}-carbonyl)-1H-pyrrol-3-yl]-4-nitro-1H-pyrrole-2-carboxamide 1-Methyl-N-[3-(4-methyl-1-piperazinyl)propyl]-4-nitro-1H-pyrrole-2-carboxamide (209 mg, 0.676 mmol; see *Tetrahedron* 56, 5225-5239 (2000)) was dissolved in methanol (25 mL) to which Pd/C-10% (182 mg) was added at 0° C. under $N_2$ with stirring. The reaction mixture was hydrogenated for 3 h at room temperature and atmospheric pressure. The catalyst was removed over Kieselguhr and the solvent was removed under reduced pressure to give the amine, which was used without further purification. 1-Isopentyl-4-nitro-1H-pyrrole-2-carboxylic acid (153 mg, 0.676 mmol; prepared according to the procedure described in *Soviet Journal of Bioorganic Chemistry (English Translation)* 4, 780-790 (1978)) was dissolved in thionyl chloride 4 mL and heated under reflux for 3 h. Excess thionyl chloride was removed under pressure at 50° C. and the acid chloride was dissolved in DCM (5 mL). The amine was dissolved in DCM (10 mL) to which NMM (200 μL) was added followed by the acid chloride at room temperature with stirring. The stirring was continued at room temperature overnight. KOH 10% (5 mL) was added and the mixture was extracted. The organic layer was collected, dried over $MgSO_4$, filtered and the solvent was removed under reduced pressure to give the crude product, which was purified by column chromatography using silica gel and 1/2/0.1 methanol/ethyl acetate/TEA. The product was obtained as glassy yellow material ($R_F$=0.45), (278 mg, 84% yield) with no distinct melting point.

NMR [DMSO-$d_6$]: 10.21(1H, s); 8.23(1H, d, J=1.8 Hz); 8.05(1H, t, J=5.4 Hz); 7.54(1H, d, J=1.8 Hz); 7.18(1H, d, J=1.8 Hz); 6.82(1H, d, J=1.8 Hz); 4.43(2H, t, J=7.4 Hz); 3.81(3H, s); 3.21-3.16(2H, q, J=6.6 Hz); 2.32-2.28(10H, m); 2.15(3H, s); 1.66-1.59(4H, quintet, J=6.7 Hz); 1.55-1.47(1H, m); 0.90(6H, d, J=6.5 Hz). IR [KBr]: 2951, 2805, 1642, 1575, 1532, 1506, 1437, 1312 cm$^{-1}$. HRFABMS: Found 488.29707; calculated for $C_{24}H_{38}N_7O_4$ 488.29853.

(ii) N-[1-Isopentyl-5-({[1-methyl-5-({[3-(4-methyl-1-piperazinyl)propyl]-amino}carbonyl)-1H-pyrrol-3-yl]amino}carbonyl)-1H-pyrrol-3-yl]-1-methyl-4-nitro-1H-pyrrole-2-carboxamide 1-Isopentyl-N-[1-methyl-5-({[3-(4-methyl-1-piperazinyl)propyl]amino}-carbonyl)-1H-pyrrol-3-yl]-4-nitro-1H-pyrrole-2-carboxamide (140 mg, 0.287 mmol; see step (i) above) was dissolved in methanol (25 mL) to which Pd/C-10% (100 mg) was added at 0° C. under $N_2$ with stirring. The reaction mixture was hydrogenated at room temperature and atmospheric pressure for 3 h. The catalyst was removed over Kieselguhr and the solvent was removed under reduced pressure. 1-Methyl-4-nitro-1H-pyrrole-2-carboxylic acid (49 mg, 0.287 mmol; see *Tetrahedron* 56, 5225-5239 (2000)) was dissolved in thionyl chloride (4 mL) and the reaction mixture was heated under reflux for 3 h. Excess thionyl chloride was removed under reduced pressure to give the acid chloride, which was dissolved in DCM (5 mL). The amine was dissolved in DCM (10 mL) to which NMM (0.1 mL) was added at room temperature with stirring followed by the acid chloride solution. The stirring was continued overnight at room temperature. KOH (5 mL, 10%) was added and the reaction mixture was extracted, and the organic layer collected, dried over $MgSO_4$, filtered and the solvent removed under reduced pressure. Column chromatography (silica gel, 1/2/0.1 methanol/ethyl acetate/TEA) was used to purify the required material, which was obtained as yellow glassy material (131 gm, 75% yield), $R_F$=0.15 with no distinct melting point.

NMR [DMSO-$d_6$]: 10.27(1H, s); 9.90(1H, s); 8.18(1H, d, J=1.8 Hz); 8.01(1H, t, J=5.6 Hz); 7.59(1H, d, J=1.8 Hz); 7.31(1H, d, J=1.8 Hz); 7.16(1H, d, J=1.8 Hz); 6.98(1H, d, J=1.8 Hz); 6.84(1H, d, J=1.8 Hz); 4.33(1H, t, J=6.9 Hz); 3.96(3H, s); 3.79(3H, s); 3.17(2H, q, J=6.5 Hz); 2.32-2.29(10 mH, m); 2.16(3H, s); 1.66-1.46(5H, m); 0.89(6H, d, J=6.4 Hz). IR [KBr]: 2949, 2803, 1650, 1588, 1531, 1506, 1399, 1309 cm$^{-1}$. HRFABMS: Found 610.34797; calculated for $C_{30}H_{44}N_9O_5$ 610.34654.

(iii) 4-(Formylamino)-N-[1-isopentyl-5-({[1-methyl-5-({[3-(4-methyl-1-piperazinyl)propyl]amino}carbonyl)-1H-pyrrol-3-yl]amino}carbonyl)-1H-pyrrol-3-yl]-1-methyl-1H-pyrrole-2-carboxamide N-[1-Isopentyl-5-({[1-methyl-5-({[3-(4-methyl-1-piperazinyl)propyl]-amino}carbonyl)-1H-pyrrol-3-yl]amino}carbonyl)-1H-pyrrol-3-yl]-1-methyl-4-nitro-1H-pyrrole-2-carboxamide (120 mg, 0.197 mmol; see step (ii) above) was dissolved in ethanol (20 mL) to which Pd/C-10% (77 mg) was added at 0° C. under $N_2$ with stirring. The reaction mixture was hydrogenated for 3 h at room temperature and atmospheric pressure. The catalyst was removed over Kieselguhr and ethyl formate (20 mL) was added to the ethanolic solution. The reaction mixture was heated under reflux for 48 h. Ethanol and excess ethyl formate were removed under reduced pressure and the crude product was purified by HPLC. The product was obtained as yellow solid with no distinct melting point (75 mg, 53% yield) after freeze-drying.

NMR [DMSO-$d_6$]: 10.03(1H, s); 9.89(1H, s); 9.87(1H, s); 8.13(1H, d, J=1.6 Hz); 8.09(1H, t, J=5.6 Hz); 7.26(1H, d, J=1.6 Hz); 7.18(1H, d, J=1.6 Hz); 7.14(1H, d, J=1.6 Hz); 7.01(1H, d, J=1.6 Hz); 6.92(1H, d, J=1.6 Hz); 6.91(1H, d, J=1.6 Hz); 4.31(2H, t, J=6.9 Hz); 3.83(3H, s); 3.81(3H, s); 3.23(2H, q, J=6.5 Hz); 3.10-2.72(8H, br & 3H, s); 1.77(2H, s, br); 1.58-1.46(3H, m); 0.90(6H, d, J=6.4 Hz). IR[KBr]: 1675, 1584, 1535, 1403, 1199, 1132 cm$^{-1}$. HRFABMS: Found 608.36634; calculated for $C_{31}H_{46}N_9O_4$ 608.36728.

Example 30

4-(Acetylamino)-N-[1-isopentyl-5-({[1-methyl-5-({[3-(4-morpholinyl)-propyl]amino}carbonyl)-1H-pyrrol-3-yl]amino}carbonyl)-1H-pyrrol-3-yl]-1-methyl-1H-pyrrole-2-carboxamide (i) 1-Isopentyl-N-[1-methyl-5-({[3-(4-morpholinyl)propyl]amino}-carbonyl)-1H-pyrrol-3-yl]-4-nitro-1H-pyrrole-2-carboxamide 1-Methyl-N-[3-(4-morpholinyl)propyl]-4-nitro-1H-pyrrole-2-carboxamide (500 mg, 1.688 mmol; see *Tetrahedron* 56, 5225-5239 (2000)) was dissolved in methanol (25 mL) at 0° C. under $N_2$ with stirring to which was added Pd/C-10% (272 mg). The reaction mixture was hydrogenated for 4 h. The catalyst was removed over Kieselguhr and the solvent was removed under reduced pressure. The amine so formed was dissolved in DCM (10 mL). 1-Isopentyl-4-nitro-1H-pyrrole-2-carboxylic acid (445 mg, 1.966 mmol; prepared according to the procedure described in *Soviet Journal of Bioorganic Chemistry (English Translation)* 4, 780-790 (1978)) was dissolved in thionyl chloride (5 mL) and the reaction mixture was heated under reflux for 4 h. Excess thionyl chloride was removed under reduced pressure and the acid chloride was dissolved in DCM (10 mL). NMM (0.2 mL) was added to the amine solution followed by the acid chloride solution at room temperature with stirring. The stirring was continued at room temperature overnight. DCM was removed under reduced pressure and the crude product was purified by column chromatography using silica gel and 1/2/0.1 methanol/ethyl acetate/TEA. Fractions containing the pure material ($R_F$=0.45) were collected and the solvents removed under reduced pressure to give yellow glassy material, which was dissolved in small amount of ethyl acetate and precipitated with n-hexane to give the required product as yellow powder (670 mg, 79% yield), m.p. 155-158° C.

NMR [CDCl$_3$]: 7.64(1H, d, J=1.7 Hz); 7.60(1H, s); 7.22 (1H, unresolved triplet); 7.18(1H, d, J=1.7 Hz); 7.07(1H, d, J=1.7 Hz); 6.66(1H, d, J=1.6 Hz); 4.43(2H, t, J=7.5 Hz); 3.93(3H, s); 3.77(2H, t, J=4.6 Hz); 3.49(2H, q, J=5.6 Hz); 2.52(6H, m); 1.80-1.58(5H, m); 0.97(6H, d, J=6.5 Hz). IR[KBr]: 1647, 1589, 1513, 1399, 1309, 1252, 1114 cm$^{-1}$. HRFABMS: Found 475.26789; calculated for C$_{23}$H$_{35}$N$_6$O$_5$ 475.26689.

(ii) N-[1-Isopentyl-5-({[1-methyl-5-({[3-(4-morpholinyl) propyl]amino}-carbonyl)-1H-pyrrol-3-yl]amino}carbonyl)-1H-pyrrol-3-yl]-1-methyl-4-nitro-1H-pyrrole-2-carboxamide 1-Isopentyl-N-[1-methyl-5-({[3-(4-morpholinyl)propyl] amino}carbonyl)-1H-pyrrol-3-yl]-4-nitro-1H-pyrrole-2-carboxamide (136 mg, 0.286 mmol; see step (i) above) was dissolved in methanol (25 mL) at 0° C. under N$_2$ with stirring to which was added Pd/C-10% (98 mg). The reaction mixture was hydrogenated at room temperature and atmospheric pressure for 2 h. The catalyst was removed over Kieselguhr and the solvent was removed under reduced pressure. The amine so formed was dissolved in DCM (5 mL). 1-Methyl-4-nitro-1H-pyrrole-2-carboxylic acid (48 mg, 0.282 mmol; see *Tetrahedron* 56, 5225-5239 (2000)) was dissolved in thionyl chloride (3 mL) and heated until reflux for 2 h. Excess thionyl chloride was removed under reduced pressure and the acid chloride so formed was dissolved in DCM (5 mL) and then added dropwise to the amine solution with stirring at room temperature. The stirring was continued overnight. The solvent was removed and the crude product was purified by column chromatography (1/2/0.1 methanol/ethyl acetate/TEA, R$_F$=0.7). Fractions containing the required material were collected and the solvents were removed under reduced pressure. The yellow glassy material was dissolved in DCM (25 mL) and extracted with KOH (10%, 5 mL). The organic layer was collected, dried over MgSO$_4$, filtered and the solvent removed under reduced pressure to give yellow glassy material (115 mg, 67% yield) with no distinct melting point.

NMR [Acetone-d$_6$]: 9.52(1H, s); 9.26(1H, s); 7.95(1H, d, J=1.7 Hz); 7.55(1H, t, unresolved); 7.38(1H, d, J=1.9 Hz); 7.33(1H, d, J=1.9 Hz); 7.20(1H, d, J=1.9 Hz); 6.91(1H, d, J=1.9 Hz); 6.84(1H, d, J=1.9 Hz); 4.44(2H, t, J=7.2 Hz); 4.08(3H, s); 3.89(3H, s); 3.64(4H, m); 3.37(2H, t, J=6.7 Hz); 2.42(6H, m); 1.77-1.56(5H, m); 0.95(6H, d, J=6.5 Hz). IR [KBr]: 1640, 1588, 1524, 1464, 1399, 1310, 1252, 1114 cm$^{-1}$. HRFABMS: 597.31332; calculated for C$_{29}$H$_{41}$N$_8$O$_6$ 597.31491.

(iii) 4-(Acetylamino)-N-[1-isopentyl-5-({[1-methyl-5-({[3-(4-morpholinyl)-propyl]amino}carbonyl)-1H-pyrrol-3-yl] amino}carbonyl)-1H-pyrrol-3-yl]-1-methyl-1H-pyrrole-2-carboxamide N-[1-Isopentyl-5-({[1-methyl-5-({[3-(4-morpholinyl) propyl]amino}-carbonyl)-1H-pyrrol-3-yl]amino}carbonyl)-1H-pyrrol-3-yl]-1-methyl-4-nitro-1H-pyrrole-2-carboxamide (115 mg, 0.193 mmol; see step (ii) above) was dissolved in ethanol (20 mL) to which was added Pd/C-10% (104 mg) at 0° C. under N$_2$ with stirring. The reaction mixture was hydrogenated for 3 h at room temperature and atmospheric pressure. The catalyst was removed over Kieselguhr and the ethanolic solution was divided into two equal volumes (i.e. 10 mL). Ethanol was removed from one of the fractions under reduced pressure and DCM (2 mL) was added to the amine with stirring. NMM (0.1 mL) was added followed by acetyl chloride (0.01 mL) at room temperature with stirring. The stirring was continued overnight. All volatile materials were removed under reduced pressure and the crude product was purified by HPLC. Fractions containing the required material were collected and freeze-dried to give white solid material (25.7 mg, 35% yield) as TFA salt with no distinct melting point.

NMR [DMSO-d$_6$]: 9.87(2H, s); 9.79(1H, s); 9.55(1H, br, TFA); 8.16(1H, t, unresolved); 7.26(1H, d, J=1.8 Hz); 7.15 (1H, d, J=1.8 Hz); 7.13(1H, d, J=1.8 Hz); 7.01(1H, d, J=1.8 Hz); 6.94(1H, d, J=1.8 Hz); 6.87(1H, d, J=1.8 Hz); 4.31(2H, t, J=6.9 Hz, isopentyl); 4.00(2H, d, J=12.4 Hz, morpho); 3.83(3H, s); 3.81(3H, s); 3.64(2H, t, J=12.0 Hz, morpho); 3.45(2H, d, J=12.0 Hz, morpho); 3.24(2H, q, J=6.2 Hz); 3.12-3.06(2H, m, side chain & 2H morpho); 1.97(3H, s); 1.87(2H, m, isopentyl); 1.58-1.48(2H, m, side chain & 1H isopentyl); 0.90(6H, d, J=6.4 Hz, isopentyl). IR [KBr]: 2925, 2858, 1655, 1583, 1526, 1465, 1400, 1260, 1200, 1131 cm$^{-1}$. HRFABMS: Found 609.34957; calculated for C$_{31}$H$_{45}$N$_8$O$_5$ 609.35129.

Example 31

4-(Formylamino)-N-[1-isopentyl-5-({[1-methyl-5-({[3-(4-morpholinyl)-propyl]amino}carbonyl)-1H-pyrrol-3-yl]amino}carbonyl)-1H-pyrrol-3-yl]-1-meth-1H-pyrrole-2-carboxamide To the second half of the amine solution (10 mL) (see Example 30, step (iii) above), ethyl formate was added (10 mL) and the reaction mixture was heated under reflux for 48 h. Volatile solvents were removed under reduced pressure and the crude product was purified by HPLC. Fractions containing the required material were collected and freeze-dried to give white solid material (22.7 mg, 32% yield) as TFA salt with no distinct melting point.

NMR [DMSO-d$_6$]: 10.03(1H, s); 9.89(1H, s); 9.87(1H, s); 9.56(1H, br, TFA); 8.16(1H, t, unresolved); 8.12(1H, d, J=1.7 Hz); 7.26(1H, d, J=1.7 Hz); 7.18(1H, d, J=1.7 Hz); 7.15(1H, d, J=1.7 Hz); 7.02(1H, d, J=1.7 Hz); 6.93(1H, d, J=1.7 Hz); 6.92(1H, d, J=1.7 Hz); 4.31(2H, t, J=7.1 Hz); 4.00(2H, d, J=11.8 Hz); 3.84(3H, s); 3.81(3H, s); 3.64(2H, t, J=11.9 Hz); 3.46(2H, d, J=12.8 Hz); 3.26(2H, q, J=6.1 Hz); 3.12-3.06(4H, m); 1.87(2H, m); 1.58-1.46(3H, m); 0.90(6H, d, J=6.3 Hz). IR [KBr]: 1682, 1640, 1584, 1529, 1403, 1263, 1202, 1132, 803 cm$^{-1}$. HRFABMS: Found 595.33717; calculated for C$_{30}$H$_{43}$N$_8$O$_5$ 595.33564.

Example 32

N-[5-({[5-({[3-(Dimethylamino)propyl] amino}carbonyl)-1-methyl-1H-pyrrol-3-yl] amino}carbonyl)-1-isopentyl-1H-pyrrol-3-yl]-4-[(3-methoxybenzoyl)amino]-1-methyl-1H-pyrrole-2-carboxamide N-[5-({[5-({[3-(Dimethylamino)propyl] amino}carbonyl)-1-methyl-1H-pyrrol-3-yl] amino}carbonyl)-1-isopentyl-1H-pyrrol-3-yl]-1-methyl-4-nitro-1H-pyrrole-2-carboxamide (260 mg, 0.469 mmol; see Example 10, step (ii) above) was dissolved in methanol (25 mL) to which Pd/C-10% (132 mg) was added at 0° C. under N$_2$ with stirring. The reaction mixture was hydrogenated for 3 h. The catalyst was removed over Kieselguhr and the solvent was removed under reduced pressure to give the amine, which was dissolved in DCM (5 mL). This solution was divided to two each (2.5 mL). m-Anisoyl chloride (50 mg, 0.293 mmol) was added dropwise at room temperature with stirring. The stirring was continued overnight. The solvent was removed under reduced pressure and the residue was dissolved in acetonitrile containing (0.1% TFA) and purified by HPLC. Fractions containing the required material were collected and freeze-dried to give the product as light pink solid with no distinct melting point (72.3 mg, 40% yield).

NMR [DMSO-d$_6$]: 10.29(1H, s); 9.96(1H, s); 9.89(1H, s); 9.27(1H, br, TFA); 8.15(1H, t, J=5.6 Hz); 7.53-7.37(3H, m); 7.32(1H, d, J=1.6 Hz); 7.29(1H, d, J=1.6 Hz); 7.16(1H, d, J=1.6 Hz); 7.14-7.10(2H, m); 7.02(1H, d, J=1.6 Hz); 6.93 (1H, d, J=1.6 Hz); 4.32(1H, t, J=6.9 Hz); 3.88(3H, s); 3.83 (3H, s); 3.82(3H, s); 3.25(2H, q, J=6.2 Hz); 3.07(2H, m); 2.79(6H, d, J=4.5 Hz); 1.84(2H, quintet, J=7.3 Hz); 1.59-1.47 (3H, m); 0.90(6H, d, J=6.3 Hz). IR [KBr]: 1644, 1583, 1533, 1464, 1436, 1402, 1260, 1200, 801, 778 cm$^{-1}$. HRFABMS: Found 659.36784; calculated for C$_{35}$H$_{47}$N$_8$O$_5$ 659.36694.

Example 33

N-[5-({[5-({[3-(Dimethylamino)propyl] amino}carbonyl)-1-methyl-1H-pyrrol-3-yl] amino}carbonyl)-1-isopentyl-1H-pyrrol-3-yl]-4-{ [(4-methoxy-phenyl)acetyl]amino}-1-methyl-1H-pyrrole-2-carboxamide The second half of the amine (see Example 32 above) was used in this experiment. To the amine (2.5 mL) in DCM was added (4-methoxy-phenyl)acetyl chloride (50 mg, 0.270 mmol) at room temperature, dropwise with stirring. The stirring was continued overnight. The solvent was removed under reduced pressure and the crude product so formed was purified by HPLC. Fractions containing the required material were collected and freeze-dried to give white solid material (51 mg, 28% yield) with no distinct melting point.

NMR [Acetone-d$_6$]: 12.15(1H, br); 9.18(1H, s); 9.11(1H, s); 9.05(1H, s); 7.67(1H, t, unresolved); 7.29-7.24(4H, m); 7.13(1H, d, J=1.7 Hz); 6.89-6.85(4H, m); 6.78(1H, d, J=1.7 Hz); 4.41(2H, t, J=6.5 Hz); 3.90(6H, s); 3.77(3H, s); 3.58(2H, s); 3.45(2H, q, J=6.1 Hz); 3.26(2H, t, J=6.1 Hz); 2.93(6H, s); 1.69-1.56(3H, m); 0.95(6H, d, J=6.6 Hz). IR [KBr]: 1650, 1588, 1515, 1465, 1402, 1251, 1203, 1133, 826, 779 cm$^{-1}$. HRFABMS: Found 673.38492; calculated for C$_3$H$_{19}$N$_8$O$_5$ 673.38259.

Example 34

Compounds of the examples were found to bind to the minor groove of DNA, as determined by the capillary electrophoresis and/or DNA footprinting methods described hereinbefore.

Example 35

Experiments that probe the binding of compounds to DNA by using n.m.r. methods are well known to those skilled in the art (see, for example: (a) J. Bunkenborg, C. Behrens, J. P. Jacobsen "*NMR characterization of the DNA binding properties of a novel Hoechst 33258 analogue peptide building block*" Bioconjugate Chemistry 13(5), 927-936 (2002); (b) G. A. Morris, K. T. Douglas "*Binding of a porphyrin conjugate of Hoechst 33258 to DNA. II. NMR spectroscopic studies detect multiple binding modes to a 12-mer nonself-complementary duplex DNA*" Nucleosides Nucleotides & Nucleic Acids 20(1-2), 145-156 (2001); and (c) X. G. Han, X. L. Gao "*Sequence specific recognition of ligand-DNA complexes studied by NMR*" Current Medicinal Chemistry 8(5) 551-581 (2001)).

Compounds of the examples were found to bind to the minor groove of DNA, as determined by experiments in which the compounds were mixed under standard conditions with DNA duplexes (e.g. d(CGACTAGTCG)$_2$) and binding was confirmed by changes observed in the n.m.r. spectra of the compound and the DNA duplex, as well as by nOe measurements on the complex formed between the compound and the DNA duplex. Narrow lines and strong cross-peaks were observed for the complex formed between the compound of Example 3 and d(CGACTAGTCG)$_2$, which is consistent with the compound of Example 3 binding with high affinity.

Example 36

Compounds of the examples were found to bind to DNA, as determined by melting temperature (Tm) measurements. Tm measurements are well known in the art as a method for investigating the stability of a DNA duplex (see V. A Bloomfield, D. M. Crothers and I. Tenneco "*Nucleic Acids: Structures, Properties and Functions*" University Science Books, Sausalito, Calif. (2000), and in particular pages 176-180 and 561-564 of that book). If a ligand stabilises the duplex, an increase in Tm is recorded. Compounds of the examples demonstrated large increases in Tm for DNA duplexes. For example, when the DNA used was a duplex of AAATTATAT-TAT, the compounds of Examples 2, 10 and 26 gave an increase in melting point of greater than 10° C.

Example 37

Compounds of the examples were found to inhibit the growth of microorganisms, for example as indicated in Tables A to G below.

TABLE A

| Example No. | MIC (µM) Organism: S. aureus | MIC (µM) Organism: E. coli |
| --- | --- | --- |
| 7 | 4.8 | >152.4 |
| 17 | 19.4 | >77.7 |
| 28 | 80 | >80.3 |
| 3 | 4.7 | >152.3 |
| Antibiotic control Amoxicillin | 0.49 | 2.0 |

TABLE B

| Example No. | MIC (µM) Organism: S. faecalis | MIC (µM) Organism: P. vulgaris |
| --- | --- | --- |
| 7 | 9.5 | 152.4 |
| 17 | 77.7 | 77.7 |
| 28 | 10.0 | >80.3 |
| 3 | 9.5 | 152.2 |
| Antibiotic control Amoxicillin | 0.49 | 8.1 |

TABLE C

| Example No. | MIC (µM) Organism: MRSA |
| --- | --- |
| 7 | 19.1 |
| 17 | >77.7 |
| 28 | 10.0 |

TABLE C-continued

| Example No. | MIC (μM) Organism: MRSA |
|---|---|
| 3 | 38.1 |
| Antibiotic control Amoxicillin | 16.1 |

TABLE D

| Example No. | MIC (μM) Organism: Aspergillus niger | MIC (μM) Organism: Candida albicans |
|---|---|---|
| 7 | 38.1 | 38.1 |
| 17 | >77.7 | >77.7 |
| 28 | >80.3 | >80.3 |
| 3 | 76.1 | 76.1 |
| Anti fungal control Fluconazole | >326.6 | 81.6 |

TABLE E

| Example No. | MIC (μM) Organism: Klebs. aerogenes | MIC (μM) Organism: Ent. cloacae |
|---|---|---|
| 7 | 38.1 | 9.5 |
| 17 | 38.9 | >77.7 |
| 28 | >80.3 | >80.3 |
| 3 | 76.2 | 76.2 |
| Control Amoxicillin | 32.3 | 4.0 |

TABLE F

| Example No. | MIC (μM) Organism: Mycobacterium fortuitum |
|---|---|
| 7 | 19.0 |
| 17 | >77.7 |
| 28 | 40.1 |
| 3 | 19.0 |
| Control Streptomycin | 21.5 |

TABLE G

| Example No. | MIC (μM) Organism: Aspergillus nidulans |
|---|---|
| 7 | 9.5 |
| 17 | 77.7 |
| 28 | 20.1 |
| 3 | 38.1 |
| Control Fluconazole | 40.8 |

Abbreviations
br=broad (in relation to NMR)
CE=capillary electrophoresis
d=doublet (in relation to NMR)
DCM=dichloromethane
DMF=N,N-dimethylformamide
DMSO=dimethylsulfoxide
eq.=equivalents
h=hour(s)
HBTU=O-benzotriazol-1-yl-N,N,N',N'-tetramethyluronium hexafluorophosphate
HCl=hydrochloric acid
HOBT=1-hydroxybenzotriazole
HPLC=high performance liquid chromatography
HREIMS=high resolution electron ionisation mass spectrometry
HRFABMS=high resolution fast atom bombardment mass spectrometry
IR=infra red (in relation to spectroscopy)
LRESMS=low resolution electrospray mass spectrometry
m=multiplet (in relation to NMR)
Me=methyl
mi.=minute(s)
m.p.=melting point
MS=mass spectroscopy
$v_{max}$=wave number (in relation to infra red spectroscopy)
NMM=N-methylmorpholine
Pd/C=palladium on carbon
q=quartet (in relation to NMR)
s=singlet (in relation to NMR)
t=triplet (in relation to NMR)
TEA=triethylamine
THF=tetrahydrofuran
TFA=trifluoroacetic acid Prefixes n-, s-, i-, t- and tert- have their usual meanings: normal, secondary, iso, and tertiary.

The invention claimed is:

1. A compound of formula I,

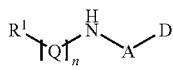

I wherein

R$^1$ represents Het$^1$, R$^{1a}$C(O)— or D-A-N(H)-[Q]$_n$-C(O)-E-C(O)—;

R$^{1a}$ represents:

H, aryl optionally substituted by one or more substituents selected from the group consisting of OH, halo, cyano, nitro, N(R$^{3a}$)R$^{3b}$, C$_{1-4}$ alkyl and C$_{1-4}$ alkoxy), aromatic or part-aromatic C$_{13-14}$ tricyclic carbocyclyl optionally substituted by one or more substituents selected from the group consisting of OH, halo, cyano, nitro, N(R$^{3a}$)R$^{3b}$, C$_{1-4}$ alkyl and C$_{1-4}$ alkoxy, and when the C$_{13-14}$ tricyclic carbocyclyl is part-aromatic, a non-aromatic part of the $C_{13-14}$ tricyclic carbocyclyl is optionally substituted by one or two oxo groups or $C_{1-12}$ alkyl optionally substituted and/or terminated by one or more substituents selected from the group consisting of halo and aryl, wherein the aryl is optionally substituted by one or more substituents selected from the group consisting of OH, halo, cyano, nitro, $N(R^{3a})R^{3b}$, $C_{1-4}$ alkyl and $C_{1-4}$ alkoxy;

A represents $C_{2-6}$ alkylene or $A^1$-C(O)N(H)-$A^2$, wherein $A^2$ is attached to D;

$A^1$ represents $C_{1-4}$ alkylene;

$A^2$ represents $C_{2-5}$ alkylene;

D represents —$N(R^{2a})R^{2b}$, —C(=$NR^{2c}$)$N(R^{2d})R^{2e}$ or —$N(R^{2f})C(=NR^{2g})N(H)R^{2h}$;

$R^{2a}$ and $R^{2b}$ independently represent H, $C_{1-6}$ alkyl, Het² or $R^{2a}$ and $R^{2b}$ together represent $(CH_2)_{3-6}$, wherein the $(CH_2)_{3-6}$ is optionally interrupted by $NR^4$ and/or is optionally substituted by one or more $C_{1-4}$ alkyl groups;

$R^4$ represents H, $C_{1-6}$ alkyl or Het³;

$R^{2c}$ to $R^{2h}$ independently represent H or $C_{1-6}$ alkyl;

E represents -$E^1$-Het⁴-, $E^{2a}$, —$(CH_2)_{0-3}N(H)C(O)$-$E^{2b}$-C(O)N(H)$(CH_2)_{0-3}$— or is represented by the formula

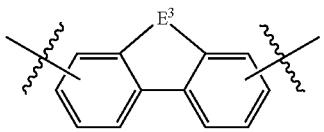

$E^3$ represents $(CH_2)_{1-2}$, CH=CH, CH=N, $CH_2$—$N(R^a)$, $(CH_2)_{0-1}C(O)$, $(CH_2)_{0-1}O$ or $(CH_2)_{0-1}S$;

$R^a$ represents H or $C_{1-6}$ alkyl;

$E^1$ represents $(CH_2)_{0-2}$ or CH=CH;

$E^{2a}$ and $E^{2b}$ independently represent $C_{2-4}$ alkenylene, $C_{3-6}$ cycloalkylene, phenylene or naphthylene;

Het¹ to Het⁴ independently represent four- to twelve-membered heterocyclic groups containing one or more heteroatoms selected from N, O and S, which heterocyclic groups are optionally substituted by one or more substituents selected from the group consisting of =O, OH, halo, cyano, nitro, $N(R^{3a})R^{3b}$, $C_{1-4}$ alkyl and $C_{1-4}$ alkoxy;

$R^{3a}$ and $R^{3b}$ independently represent, H or $C_{1-4}$ alkyl, or $R^{3a}$ represents —C(O)$R^5$;

$R^5$ represents H or $C_{1-4}$ alkyl;

n represents, 2, 3, 4 or 5;

each individual Q independently represents a structure represented by formula Ia, Ib, Ic, Id, Ie or If

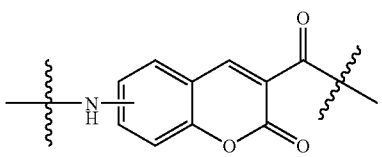

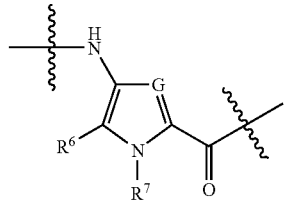

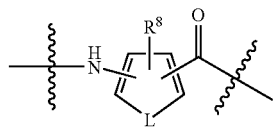

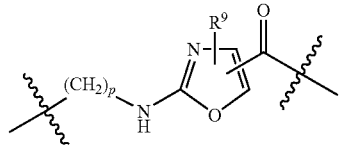

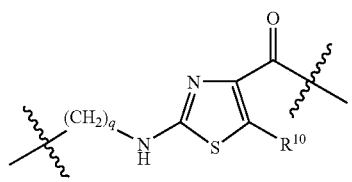

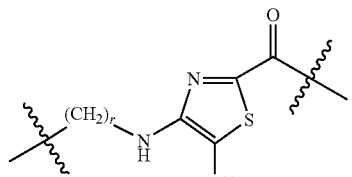

wherein $R^6$ represents H or $C_{1-6}$ alkyl;

$R^7$ represents $C_{1-12}$ alkyl;

$R^8$, $R^9$, $R^{10}$ and $R^{11}$ independently represent H or $C_{1-12}$ alkyl;

G represents CH or N;

L represents O or S; and p, q and r independently represent 0, 1, 2 or 3;

provided that the compound comprises at least one structure represented by formula Ib, Ic, Id, Ie or If in which $R^6$ or $R^7$, $R^8$, $R^9$, $R^{10}$ or $R^{11}$, respectively, represents branched, cyclic or part cyclic $C_{3-5}$ alkyl; or a pharmaceutically acceptable derivative thereof.

2. A compound as claimed in claim 1, wherein:

$R^{1a}$ represents H or $C_{1-12}$ alkyl, optionally substituted and/or terminated by one or more substituents selected from halo and aryl optionally substituted by one or more substituents selected the group consisting of OH, halo, cyano, nitro, $N(R^{3a})R^{3b}$, $C_{1-4}$ alkyl and $C_{1-4}$ alkoxy; and the compound comprises at least one structure represented by formula Ib, Ic, Id, Ie or If in which $R^7$, $R^8$, $R^9$, $R^{10}$ or $R^{11}$, respectively, represents branched, cyclic or part cyclic $C_{3-5}$ alkyl.

3. A compound as claimed in claim 1, wherein aryl is phenyl or naphthyl.

4. A compound as claimed in claim 1, wherein alkyl and alkoxy groups are:

(a) straight-chain;
(b) branched-chain and/or cyclic; or
(c) part cyclic/acyclic.

5. A compound as claimed in claim 1, wherein alkyl and alkoxy groups are:
(a) saturated or unsaturated;
(b) interrupted by one or more oxygen and/or sulfur atoms; and/or
(c) unless otherwise specified, substituted by one or more halo atoms.

6. A compound as claimed in claim 1, which is a compound of formula II, $$R^1-Q^1-Q^2-Q^3-\overset{H}{N}-A-N\overset{R^{2a}}{\underset{R^{2b}}{}}$$   II wherein
R$^1$ represents Het$^1$, R$^{1a}$C(O)— or D-A-N(H)-Q$^3$-Q$^2$-Q$^1$-C(O)-E-C(O)—;
Q$^1$ is absent or represents a structure represented by formula Ia, Ib, Ic, Id, Ie or If;
Q$^2$ represents a structure represented by formula Ib, Ie or If; and
Q$^3$ represents a structure represented by formula Ib, Id, Ie or If; provided that:
(a) at least one of Q$^1$, Q$^2$ and Q$^3$ represents a structure represented by formula Id, Ie or If; and
(b) at least one of R$^6$ or R$^7$, R$^8$, R$^9$, R$^{10}$ and R$^{11}$ represents branched, cyclic or part cyclic C$_{3-5}$ alkyl, or a pharmaceutically acceptable derivative thereof.

7. A compound as claimed in claim 1, wherein the compound comprises:
(a) at least one structure represented by formula Ib in which G represents N and R$^6$ represents branched, cyclic or part cyclic C$_{3-5}$ alkyl;
(b) at least one structure represented by formula Id in which p represents 0 and R$^9$ represents branched, cyclic or part cyclic C$_{3-5}$ alkyl; and/or
(c) at least one structure represented by formula Ie in which q represents 0 and R$^{10}$ represents branched, cyclic or part cyclic C$_{3-5}$ alkyl.

8. A compound as claimed in claim 1, wherein each of the at least one branched, cyclic or part cyclic C$_{3-5}$ alkyl groups independently represents isopropyl, cyclopropylmethyl, isopentyl or cyclopentyl.

9. A compound as claimed in claim 1, wherein the compound comprises at least one structure represented by formula Ib, Ic, Id, Ie or If in which R$^7$, R$^8$, R$^9$, R$^{10}$ or R$^{11}$, respectively, represents isopropyl.

10. A compound as claimed in claim 1, which compound comprises at least one structure represented by the formula 11. A compound of formula IIa, $$R^1-Q^1-Q^2-Q^3-\overset{H}{N}-A-N\overset{R^{2a}}{\underset{R^{2b}}{}}$$   IIa wherein
R$^1$ represents
a nine-membered aromatic heterocycle containing two heteroatoms selected from N, O and S,
R$^{1a}$C(O)— or
D-A-N(H)-Q$^3$-Q$^2$-Q$^1$-C(O)-E-C(O)—;
R$^{1a}$ represents
H,
phenyl optionally substituted by C$_{1-2}$ alkyoxy,
9,10-dioxo-9,10-dihydroanthracenyl optionally substituted by C$_{1-2}$ alkoxy,
saturated, optionally branched C$_{1-6}$ alkyl or
saturated C$_{1-3}$ n-alkyl, terminated by phenyl optionally substituted by C$_{1-2}$ alkyoxy;
A represents saturated C$_{2-4}$ alkylene or (CH$_2$)$_{1-3}$—C(O)N(H)—(CH$_2$)$_{2-4}$;
D represents —N(R$^{2a}$)R$^{2b}$;
R$^{2a}$ and R$^{2b}$ independently represent
C$_{1-3}$ alkyl or a nine- or ten-membered aromatic heterocycle containing one to three heteroatoms selected from N, O and S, or
R$^{2a}$ and R$^{2b}$ together represent (CH$_2$)$_{3-5}$ optionally interrupted by NR$^4$;
R$^4$ represents
C$_{1-3}$ alkyl or a nine- or ten-membered aromatic heterocycle containing one to three heteroatoms selected from N, O and S;
E represents
-(2,5-indolyl-,
—(CH$_2$)$_{0-2}$-(2,6-indolyl)-,
—CH=CH-(2,6-indolyl)-,
trans-ethenylene,
trans-cyclopropylene,
1,3- or 1-4-phenylene,
—CH$_2$N(H)C(O)-(1,3- or 1,4-phenylene)-C(O)N(H)CH$_2$—,
or one of the following structures

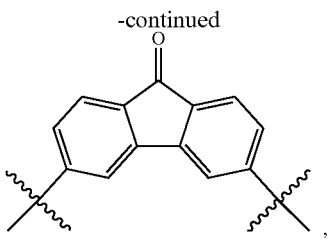

$Q^1$ is absent or represents a structure represented by formula Ia, Ib, Ic, Id, Ie or If;

$Q^2$ represents a structure represented by formula Ib, Ie or If;

$Q^3$ represents a structure represented by formula Ib, Id, Ie or If;

wherein the structures of formulae Ia, Ib, Ic, Id, Ie and If are as follows

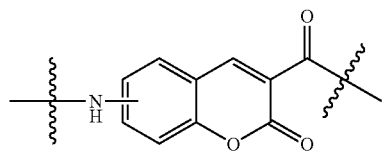
Ia

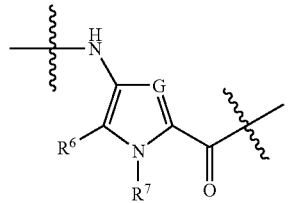
Ib

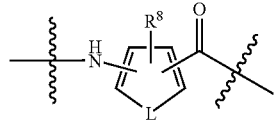
Ic

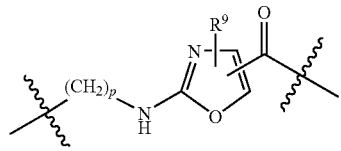
Id

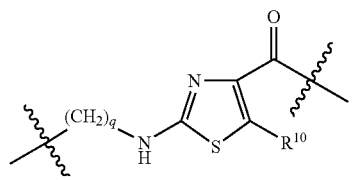
Ie

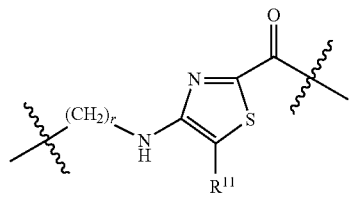
If wherein $R^6$ represents H or, when G represents N, $R^6$ represents H or branched, cyclic or part cyclic $C_{3-5}$ alkyl;

$R^7$, $R^8$, $R^9$, $R^{10}$ and $R^{11}$ independently represent saturated, optionally branched $C_{1-6}$ alkyl or represents H;

provided that the compound comprises at least one structure represented by formula Ie in which $R^{10}$ represents branched, cyclic or part cyclic $C_{3-5}$ alkyl.

12. A compound as claimed in claim 11, wherein the compound comprises at least one structure represented by formula Ie in which $R^{10}$ represents cyclopropylmethyl, isopentyl, cyclopentyl or isopropyl.

13. A compound as claimed in claim 11, wherein the compound comprises at least one structure represented by formula Ie in which $R^{10}$ represents isopropyl.

14. A compound of formula IIb,

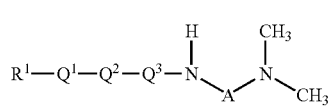
IIb wherein $R^1$ represents a nine-membered aromatic heterocycle containing two heteroatoms selected from N, O and S.

HC(O)—, (methoxyphenyl)C(O)—, (9,10-dioxo-9,10-dihydroanthracenyl)C(O)—, (saturated $C_{1-3}$ alkyl)C(O)—, (methoxyphenylacetyl)C(O)—, or $(CH_3)_2$N-A-N(H)-$Q^3$-$Q^2$-$Q^1$-C(O)-E-C(O)—;

A represents saturated $C_{2-4}$ n-alkylene or $(CH_2)_2$—C(O)N(H)—$(CH_2)_3$;

E represents —$CH_2$N(H)C(O)-(1,3-phenylene)-C(O)N(H)$CH_2$—;

$Q^1$ is absent or represents a structure represented by formula Ia, Ib, Ic, Id, Ie or If;

$Q^2$ represents a structure represented by formula Ib, Ie or If;

$Q^3$ represents a structure represented by formula Ib, Id, Ie or If;

wherein the structures of formulae Ia, Ib, Ic, Id, Ie and If are as follows

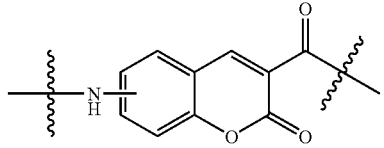
Ia

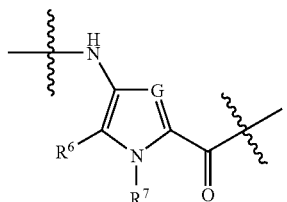
Ib

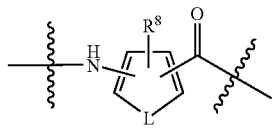
Ic

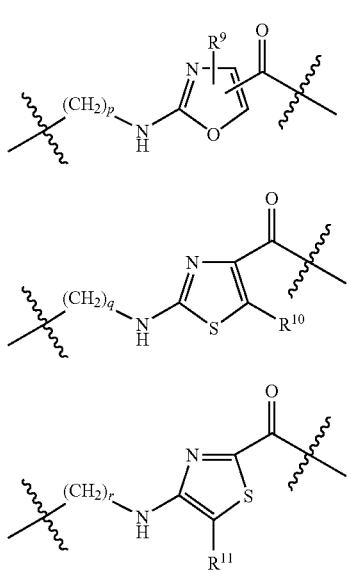

wherein
R[6] represents H or, when G represents N, R[6] represents H or branched, cyclic or part cyclic $C_{3-5}$ alkyl;
R[7], R[9], R[10] and R[11] independently represent saturated, optionally branched $C_{1-3}$ alkyl;
provided that the compound comprises at least one structure represented by formula Ie in which R[10] represents branched, cyclic or part cyclic $C_{3-5}$ alkyl.

15. A compound as claimed in claim 14, wherein the compound comprises at least one structure represented by formula Ie in which R[10] represents cyclopropylmethyl, isopentyl, cyclopentyl or isopropyl.

16. A compound as claimed in claim 14, wherein the compound comprises at least one structure represented by formula Ie in which R[10] represents isopropyl.

17. A compound as claimed in claim 1, which compound is selected from the following:

(i) N-[5-({[5-({[3-(Dimethylamino)propyl]amino}carbonyl)-1-methyl-1H-pyrrol3-yl]amino}carbonyl)-1-isopropyl-1-H-pyrrol-3-yl]-4-[(3,3-dimethylbutanoyl)amino]-1-methyl-1H-pyrrole-2-carboxamide;

(ii) N-[5-({[5-({[3-(Dimethylamino)propyl]amino}carbonyl)-1-methyl-1H-pyrrol-3-yl]amino}carbonyl)-1-isopropyl-1H-pyrrol-3-yl]-4-(formylamino)-1-methyl-1H-pyrrole-2-carboxamide;

(iii) N-[3-(Dimethylamino)propyl]-2-({[4-({[4-(formylamino)-1-methyl-1H-pyrrol-2-yl]carbonyl}amino)-1-methyl-1H-pyrrol-2-yl]carbonyl}-amino)-5-isopropyl-1,3-thiazole-4-carboxamide;

(iv) N-[5-({[3-(Dimethylamino)propyl]amino}carbonyl)-1-isopropyl-1H-pyrrol-3-yl]-4-({[4-(formylamino)-1-isopropyl-1H-pyrrol-2-yl]carbonyl}-amino)-1-isopropyl-1H-pyrrole-2-carboxamide (v) N-[5-({[5-({[3-(Dimethylamino)propyl]amino}carbonyl)-1-isopentyl-1H-pyrrol-3-yl]amino}carbonyl)-1-isopentyl-1H-pyrrol-3-yl]-4-(formyl-amino)-1-methyl-1H-pyrrole-2-carboxamide;

(vi) N-[5-({[5-({[3-(Dimethylamino)propyl]amino}carbonyl)-1-isopropyl-1H-pyrrol-3-yl]amino}carbonyl)-1-methyl-1H-pyrrol-3-yl]-4-(formylamino)-1-isopropyl-1H-pyrrole-2-carboxamide;

(vii) N-[5-({[3-(Dimethylamino)propyl]amino}carbonyl)-1-methyl-1H-pyrrol-3-yl]-2-({[4-(formylamino)-1-methyl-1H-pyrrol-2-yl]carbonyl}-amino)-5-isopropyl-1,3-thiazole-4-carboxamide;

(viii) 4-({[4-(Formylamino)-1-methyl-1H-pyrrol-2-yl]carbonyl}amino)-1-iso-propyl-N-[1-methyl-5-({[3-(4-morpholinyl)propyl]amino}carbonyl)-1H-pyrrol-3-yl]-1H-pyrrole-2-carboxamide;

(ix) 4-(Formylamino)-N-[1-isopropyl-5-({[1-methyl-5-({[3-(1-pyrrolidinyl)-propyl]amino}carbonyl)-1H-pyrrol-3-yl]amino}carbonyl)-1H-pyrrol-3-yl]-1-methyl-1H-pyrrole-2-carboxamide;

(x) N-[5-({[5-({[3-(Dimethylamino)propyl]amino}carbonyl)-1-methyl-1H-pyrrol-3-yl]amino}carbonyl)-1-isopentyl-1H-pyrrol-3-yl]-4-(formylamino)-1-methyl-1H-pyrrole-2-carboxamide;

(xi) 2-(Acetylamino)-N-[5-({[5({[3-(dimethylamino)propyl]amino}-carbonyl)-1-methyl-1H-pyrrol-3-yl]amino}carbonyl)-1-methyl-1H-pyrrol-3-yl]5-isopropyl-1,3-thiazole-4-carboxamide;

(xii) 2-(Acetylamino-)-N-[5-({[4-({[3-(dimethylamino)propyl]amino}-carbonyl)-5-isopropyl-1,3-thiazol-2-yl]amino}carbonyl)-1-methyl-1H-pyrrol-3-yl]-5-isopropyl-1,3-thiazole-4-carboxamide;

(xiii) 2-(Acetylamino)-N-(5-{[(3-{[3-(dimethylamino)propyl]amino}-3-oxo-propyl)amino]carbonyl}-1-methyl-1H-pyrrol-3-yl)-5-isopropyl-1,3-thiazole-4-carboxamide;

(xiv) N[1],N[3]-Bis(2-{[5({[4({[3-(dimethylamino)propyl]aminol}carbonyl)-5-isopropyl-1,3-thiazol-2-yl]amino}carbonyl)-1-methyl-1H-pyrrol-3-yl]-amino}-2-oxoethyl) isophthalamide;

(xv) N-[5-({[5-({[3-(Dimethylamino)propyl]amino}carbonyl)-1-methyl-1H-pyrrol-3-yl]amino}carbonyl)-1-isopropyl-1H-pyrrol-3-yl]-4-(acetylamino)-1-methyl-1H-pyrrole-2-carboxamide;

(xvi) N-[5-({[5-({[3-(Dimethylamino)propyl]amino}carbonyl)-1-methyl-1H-pyrrol-3-yl]amino}carbonyl)-1-isopentyl-1H-pyrrol-3-yl]-4-(acetyl-amino)-1-methyl-1H-pyrrole-2-carboxamide;

(xvii) N[2],N[5]-Bis[5({[4({[3-(dimethylamino)propyl]amino}carbonyl)-5-isopropyl-1,3-thiazol-2-yl]amino}carbonyl)-1-methyl-1H-pyrrol-3-yl]-1H-indole-2,5-dicarboxamide;

(xviii) N[2],N[5]-Bis[1-isopentyl-5-({[1-methyl-5-({[3(4-morpholinyl)propyl]-amino}carbonyl)-1H-pyrrol-3-yl]amino}carbonyl)-1H-pyrrol-3-yl]-1H-indole-2,5-dicarboxamide;

(xix) N[2],N[5]-Bis[5({[5({[3-(dimethylamino)propyl]amino}carbonyl)-1-methyl-1H-pyrrol-3-yl]amino}carbonyl)-1-isopentyl-1H-pyrrol-3-yl]-1H-indole-2,5-dicarboxamide;

(xx) N[2], N[5]Bis[1isopentyl-5({[1methyl5({[3(4methyl-1-piperazinyl)-propyl]amino}carbonyl)-1H-pyrrol-3-yl]amino}carbonyl)-1H-pyrrol-3-yl]-1H-indole-2,5-dicarboxamide;

(xxi) 2-({[4-({[4-(Acetylamino)-1-methyl-1H-imidazol-2-yl]carbonyl}-amino)-1-methyl-1H-pyrrol-2-yl]carbonyl}amino)-N-[3-(dimethylamino)-propyl]-5-isopropyl-1,3-thiazole-4-carboxamide;

(xxii) 4-(Acetylamino)-N-[1-isopentyl-5-({[1-methyl-5-({[3-(4-methyl-1-piperazinyl)propyl]amino}carbonyl)-1H-pyrrol-3-yl]amino}carbonyl)-1H-pyrrol-3-yl]-1-methyl-1H-pyrrole-2-carboxamide;

(xxiii) N-[1-Isopentyl-5-({[1-methyl-5-({[3-(4-methyl-1-piperazinyl)-propyl]amino}carbonyl)-1H-pyrrol-3-yl]amino}carbonyl)-1H-pyrrol-3-yl]-4-[(3-methoxybenzoyl) amino]-1-methyl-1H-pyrrole-2-carboxamide;

(xxiv) N-[5-({[3-(Dimethylamino)propyl]amino}carbonyl)-1-methyl-1H-pyrrol-3-yl]-4-({[5-(formylamino)-2-methyl-3-thienyl]carbonyl}amino)-1-isopentyl-1H-pyrrole-2-carboxamide;

(xxv) N-[5-({[5-({[3-(dimethylamino)propyl]amino}carbonyl)-1-methyl-1H-pyrrol-3-yl]amino}carbonyl)-1-methyl-1H-pyrrol-3-yl]-5-isopropyl-2-[(3-methoxybenzoyl)amino]-1,3-thiazole-4-carboxamide;

(xxvi) N-[5-({[3-(Dimethylamino)propyl]amino}carbonyl)-1-methyl-1H-pyrrol-3-yl]-4-{[(5-{[(9,10-dioxo-9,10-dihydro-2-anthracenyl)carbonyl]amino}-2-methyl-3-thienyl)carbonyl]amino}-1-isopentyl-1H-pyrrole-2-carboxamide;

(xxvii) N-[1-(Cyclopropylmethyl)-5-({[5-({[3-(dimethylamino)propyl]-amino}carbonyl)-1-methyl-1H-pyrrol-3-yl]amino}carbonyl)-1H-pyrrol-3-yl]-4-(formylamino)-1-methyl-1H-pyrrole-2-carboxamide;

(xxviii) 1-Cyclopentyl-N-[5-({[3-(dimethylamino)propyl]amino}carbonyl)-1-methyl-1H-pyrrol-3-yl]-4-({[4-(formylamino)-1-methyl-1H-pyrrol-2-yl]-carbonyl}-amino)-1H-pyrrole-2-carboxamide;

(xxix) $N^2,N^7$-Bis[5-({[4-({[3-(dimethylamino)propyl]amino}carbonyl)-5-isopropyl-1,3-thiazol-2-yl]amino}carbonyl)-1-methyl-1H-pyrrol-3-yl]-9,10-dihydro-2,7-phenanthrenedicarboxamide;

(xxx) 4-(Formylamino)-N-[1-isopentyl-5-({[1-methyl-5-({[3-(4methyl-1-piperazinyl)propyl]amino}carbonyl)-1H-pyrrol-3-yl]amino}carbonyl)-1H-pyrrol-3-yl]-1-methyl-1H-pyrrole-2-carboxamide;

(xxxi) 4-(Acetylamino)-N-[1-isopentyl-5-({[1-methyl5({[3-(4-morpholinyl) propyl]amino}carbonyl)-1H-pyrrol-3-yl]amino}carbonyl)-1H-pyrrol-3-yl]-1-methyl-1H-pyrrole-2-carboxamide;

(xxxii) 4-(Formylamino)-N-[1-isopentyl-5-({[1-methyl-5-({[3-(4-morpholinyl) propyl]amino}carbonyl)-1H-pyrrol-3-yl]amino}carbonyl)-1H-pyrrol-3-yl]-1-methyl-1H-pyrrole-2-carboxamide;

(xxxiii) N[5({[5({[3-(Dimethylamino)propyl]amino}carbonyl)-1-methyl-1H-pyrrol-3-yl]amino}carbonyl)-1-isopentyl-1H-pyrrol-3-yl]-4-[(3-methoxybenzoyl)amino]-1-methyl-1H-pyrrole-2-carboxamide; and (xxxiv) N[5({[5({[3-(Dimethylamino)propyl]amino}carbonyl)-1-methyl-1H-pyrrol-3-yl]amino}carbonyl)-1-isopentyl-1H-pyrrol-3-yl]-4-{[(4-methoxyphenyl)acetyl]amino}-1-methyl-1H-pyrrole-2-carboxamide.

18. A compound as claimed in claim 17 which is:

(a) N-[5-({[5({[3-(Dimethylamino)propyl]amino}carbonyl)-1-methyl-1H-pyrrol-3-yl]amino}carbonyl)-1-isopropyl-1H-pyrrol-3-yl]-4-(formylamino)-1-methyl-1H-pyrrole-2-carboxamide;

(b) N-[3-(Dimethylamino)propyl]-2-({[4-({[4-(formylamino)-1-methyl-1H-pyrrol-2yl]carbonyl}amino)-1-methyl-1H-pyrrol-2-yl]carbonyl}-amino)-5-isopropyl-1,3-thiazole-4-carboxamide;

(c) N-[5-({[3-(Dimethylamino)propyl]amino}carbonyl)-1-methyl-1H-pyrrol-3yl]-2-({[4-(formylamino)-1-methyl-1H-pyrrol-2-yl]carbonyl}-amino)-5-isopropyl-1,3-thiazole-4-carboxamide;

(d) N-[5-({[5-({[3-(Dimethylamino)propyl]amino}carbonyl)-1-methyl-1H-pyrrol-3-yl]amino}carbonyl)-1-isopentyl-1H-pyrrol-3-yl]-4-(formylamino)-1-methyl-1H-pyrrole-2-carboxamide;

(e) $N^2,N^5$-Bis[1-isopentyl-5-({[1-methyl-5-({[3-(4-morpholinyl)propyl]-amino}carbonyl)-1H-pyrrol-3-yl]amino}carbonyl)-1H-pyrrol-3-yl]-1H-indole-2,5-dicarboxamide;

(f) N-[1-(Cyclopropylmethyl)-5-({[5-({[3-(dimethylamino)propyl]-amino}carbonyl)-1-methyl-1H-pyrrol-3-yl]amino}carbonyl)-1H-pyrrol-3-yl]-4-(formylamino)-1-methyl-1H -pyrrole-2-carboxamide; or (g) $N^2$, $N^7$-Bis[5-({[4({[3-(dimethylamino)propyl]amino}carbonyl)-5-isopropyl-1,3-thiazol-2-yl]amino}carbonyl)-1-methyl-1H-pyrrol-3-yl]-9,10-dihydro-2,7-phenanthrenedicarboxamide.

19. A compound as claimed in claim 11 which is N-[3-(dimethylamino)propyl]-2-({[4-({[4-(formylamino)-1-methyl-1H-pyrrol-2-yl]carbonyl}-amino)-1-methyl-1H-pyrrol-2-yl]carbonyl}amino)-5-isopropyl-1,3-thiazole-4-carboxamide.

20. A compound as claimed in claim 1, which binds to and/or has specificity for DNA sequences that contain at least one GC base pairing.

21. A compound as claimed in claim 11 or 14, which binds to and/or has specificity for DNA sequences that contain at least one GC base pairing, provided that the compound comprises at least one structure represented by formula Id, Ie or If.

22. A compound as claimed in claim 1 which has different binding affinities at different minor groove binding sites in double-stranded DNA molecules having more than one minor groove binding site.

23. A compound as claimed in claim 22, wherein the different minor groove binding sites comprise solely AT base pairs.

24. A pharmaceutical formulation including a compound as defined in claim 1 in admixture with a pharmaceutically-acceptable adjuvant, diluent or carrier.

25. A method of stabilising a DNA duplex formed between first and second single strands of DNA, which method comprises contacting that DNA duplex with a compound as defined in claim 1.

26. A method of enhancing the difference in melting temperatures between first and second DNA duplexes, wherein each DNA duplex is formed from a first single strand of DNA that is the same in each duplex and a second single strand of DNA that is different in each duplex, which method comprises contacting each DNA duplex with a compound as defined in claim 1.

27. A process for the preparation of compounds of formula I as defined in claim 1 which comprises:

(a) reaction of a compound of formula III,

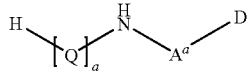

III wherein $A^a$ represents A or, when a represents 0, then $A^a$ represents A or $A^2$, a is as defined below, with a compound of formula IV,

IV wherein $A^b$ represents a direct bond or $-A^1-C(O)-$, $L^1$ represents a leaving group, a and b both represent integers from 0 to 5, the sum of a and b being 2, 3, 4 or 5;

(b) for compounds of formula I in which $R^1$ represents D-A-N(H) $-[Q]_n$-C(O)-E-C(O)—, reaction of two equivalents of a compound of formula V,

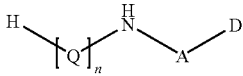

V with a compound of formula VI, $L^2$-C(O)-E-C(O)-$L^2$   VI wherein $L^2$ represents a leaving group, the two $L^2$ groups being the same or different; or (c) deprotection of a protected derivative of a compound of formula I.

28. A compound of formula V, as defined in claim 27, or a protected derivative thereof.

* * * * *

SEQUENCE LISTING

<160> NUMBER OF SEQ ID NOS: 6

<210> SEQ ID NO 1
<211> LENGTH: 12
<212> TYPE: DNA
<213> ORGANISM: Artificial sequence
<220> FEATURE:
<223> OTHER INFORMATION: Synthetically generated oligonucleotide

<400> SEQUENCE: 1
aaattatatt at                                                      12

```
<210> SEQ ID NO 2
<211> LENGTH: 12
<212> TYPE: DNA
<213> ORGANISM: Artificial sequence
<220> FEATURE:
<223> OTHER INFORMATION: Synthetically generated oligonucleotide

<400> SEQUENCE: 2
gggccgcgcc gc                                                          12

<210> SEQ ID NO 3
<211> LENGTH: 10
<212> TYPE: DNA
<213> ORGANISM: Artificial sequence
<220> FEATURE:
<223> OTHER INFORMATION: Synthetically generated oligonucleotide

<400> SEQUENCE: 3
cgactagtcg                                                             10

<210> SEQ ID NO 4
<211> LENGTH: 10
<212> TYPE: DNA
<213> ORGANISM: Artificial sequence
<220> FEATURE:
<223> OTHER INFORMATION: Synthetically generated oligonucleotide

<400> SEQUENCE: 4
ggactagtcg                                                             10

<210> SEQ ID NO 5
<211> LENGTH: 10
<212> TYPE: DNA
<213> ORGANISM: Artificial sequence
<220> FEATURE:
<223> OTHER INFORMATION: Synthetically generated oligonucleotide

<400> SEQUENCE: 5
ccactagtgg                                                             10

<210> SEQ ID NO 6
<211> LENGTH: 166
<212> TYPE: DNA
<213> ORGANISM: Artificial sequence
<220> FEATURE:
<223> OTHER INFORMATION: Synthetically generated oligonucleotide

<400> SEQUENCE: 6
ggatccatat gcggcaatac acatggccga tttccaactg cactagtcgt agcgcgatca      60
aggttaagct cccgttctat cctggtatag caattagggc gtgaagagtt atgtaaagta     120
cgtccggtgg ggtctgtttt gtcatctcag cctcgaatgc ggatcc                    166
```